(12) United States Patent
Fink et al.

(10) Patent No.: US 7,531,539 B2
(45) Date of Patent: *May 12, 2009

(54) PYRROLOTRIAZINE KINASE INHIBITORS

(75) Inventors: Brian E. Fink, Yardley, PA (US); Ping Chen, Belle Mead, NJ (US); Ashok Vinayak Purandare, Pennington, NJ (US); Honghe Wan, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/835,456

(22) Filed: Aug. 8, 2007

(65) Prior Publication Data

US 2008/0045496 A1 Feb. 21, 2008

Related U.S. Application Data

(60) Provisional application No. 60/821,844, filed on Aug. 9, 2006, provisional application No. 60/915,460, filed on May 2, 2007.

(51) Int. Cl.
| C07D 487/04 | (2006.01) |
| C07D 403/12 | (2006.01) |
| C07D 403/14 | (2006.01) |
| A61K 31/53  | (2006.01) |
| A61P 19/02  | (2006.01) |
| A61P 35/00  | (2006.01) |

(52) U.S. Cl. ..................... 514/243; 544/183
(58) Field of Classification Search ............ 544/183; 514/243

See application file for complete search history.

(56) References Cited

U.S. PATENT DOCUMENTS 6,670,357 B2   12/2003  Leftheris et al.
6,869,952 B2   3/2005   Bhide et al.
6,982,265 B1   1/2006   Hunt et al.
2006/0084650 A1  4/2006  Dong et al.

FOREIGN PATENT DOCUMENTS

WO  WO 00/71129   11/2000
WO  WO 03/090912  11/2003

OTHER PUBLICATIONS

Cecil Textbook of Medicine, edited by Bennet, J.C., and Plum F., 20th edition, vol. 1, 1004-1010, 1996.*
Mass, R. D., Int. J. Radiation Oncology Bio. Phys. vol. 58(3): 932-940, 2004.*
Fabbro et al. Pharmacology & therapeutics 93, 79-98, 2002.*

* cited by examiner

*Primary Examiner*—Venkataraman Balasubramanian
(74) *Attorney, Agent, or Firm*—Elliott Korsen

(57) ABSTRACT

The present invention provides compounds of formula I

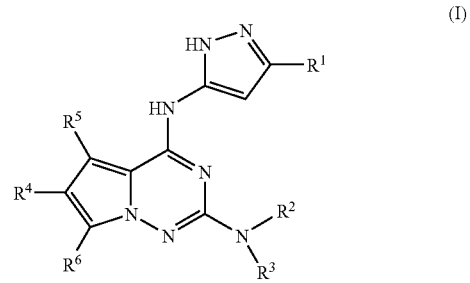

(I)

and pharmaceutically acceptable salts thereof.

The formula I compounds inhibit tyrosine kinase activity of such as TrkA, TrkB, TrkC, Jak2, Jak3 and CK2, thereby making them useful as antiproliferative agents for the treatment of cancer and other diseases.

10 Claims, No Drawings

PYRROLOTRIAZINE KINASE INHIBITORS

RELATED APPLICATION

This application claims the benefit of U.S. Provisional Application No. 60/821,844, filed Aug. 9, 2006 and U.S. Provisional Application No. 60/915,460, filed May 2, 2007, incorporated herein by reference in their entirety.

FIELD OF THE INVENTION

This invention relates to novel compounds that are useful as anti-cancer agents. This invention also relates to a method of using the compounds in the treatment of proliferative diseases, such as cancer, and to pharmaceutical compositions containing the compounds.

BACKGROUND OF THE INVENTION

Tyrosine kinases play a critical role in signal transduction for several cellular functions including cell proliferation, carcinogenesis, apoptosis, and cell differentiation. Inhibitors of these enzymes are useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Tyrosine kinases that have been implicated in these processes include Abl, CDK's, EGF, EMT, FGF, FAK, Flk-1/KDR, Flt-3, GSK-3, GSKbeta-3, HER-2, IGF-1R, IR, Jak2, LCK, MET, PDGF, Src, Tie-2, TrkA, TrkB and VEGF. Hence, there is an ongoing need to investigate novel compounds that can be used to regulate or inhibit tyrosine kinase enzymes. Inhibitors of tyrosine kinase enzymes may be used to treat diseases which are characterized by an overexpression or upregulation of tyrosine kinase activity such as cancer, diabetes, restenosis, arteriosclerosis, psoriasis, angiogenic diseases and immunologic disorders (Powis, G.; Workman P. Signaling Targets For The Development of Cancer Drugs. *Anti-Cancer Drug Design* (1994), 9: 263-277; Merenmies, J.; Parada, L. F.; Henkemeyer, M. Receptor Tyrosine Kinase Signaling in Vascular Development. *Cell Growth Differ* (1997) 8: 3-10; Shawver, L. K.; Lipsosn, K. E.; Fong, T. A. T.; McMahon, G.; Plowman, G. D.; Strawn, L. M. Receptor Tyrosine Kinases As Targets For Inhibition of Angiogenesis. *Drug Discovery Today* (1997) 2: 50-63; all herein incorporated by reference).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. In general, RTKs are activated by ligand-induced oligomerization and tyrosine autophosphorylation of specific intracellular substrates such as PLCγ, PI3 kinase, ras, and raf MEK/Erk1. Tyrosine kinase activity is an absolute requirement for signal transduction through this class of receptor.

Tropomysosin Related Kinases (Trk) are a family of receptor tyrosine kinases composed of three family members, TrkA, TrkB and TrkC. The Trks bind with high affinity to, and mediate the signal transduction induced by the Neurotrophin family of ligands whose prototype members are Nerve Growth Factor (NGF), Brain-Derived Neurotrophic Factor (BDNF) and Neurotrophin-3, -4 and -5 (NT-3, NT-4 and NT-5). In addition, a co-receptor lacking enzymatic activity, p75, has been identified which binds all neurotrophines (NTs) with low affinity and regulates neurotrophin signaling. A critical role of the Trks and their ligands during the development of the central and peripheral nervous systems have been established through gene disruption studies in mice. In particular, TrkA-NGF interaction was shown as a requirement for the survival of certain peripheral neuron populations involved in mediating pain signaling. In addition to these developmental consequences of Trk signaling, the subversion of this receptor and its signaling pathway in certain malignancies has also been documented. Of particular note are reports of aberrant expression of NGF and TrkA receptor kinase are implicated in the development and progression of human prostatic carcinoma and pancreatic ductal adrenocarcinoma and activating chromosomal rearrangements of Trks in acute myelogenous leukemia (AML), thyroid and breast cancers and receptor point mutations predicted to be constitutively activating in colon tumors. In addition to these activation mechanisms, elevated Trk receptor and ligand have also been reported in a variety of tumor types including multiple myeloma, melanoma, neuroblastoma, ovarian and pancreatic carcinoma. The neurotrophins and their corresponding Trk receptor subtypes have been shown to exert a variety of pleiotropic responses on malignant cells, including enhanced tumor invasiveness and chemotaxis, activation of apoptosis, stimulation of clonal growth, and altered cell morphology. These effects have been observed in carcinomas of the prostate, breast, thyroid, colon, malignant melanomas, lung carcinomas, glioblastomas, pancreatic carcinoids and a wide variety of pediatric and neuroectodermal-derived tumors including Wilm's tumor, neuroblastomas and medulloblastomas. Neurotrophins and their receptor subtypes have been implicated in these cancers either through autocrine or paracrine mechanisms involving carcinoma cells and the surrounding parenchymal and stromal tissues. In addition, profound or significantly attenuated reduction of bone pain caused by prostate cancer metastasis has recently been achieved by utilization of anti-NGF antibody. Overall, the oncogenic properties of Trk signaling in multiple tumor types makes the modulation of the Trk receptor signaling a potentially attractive therapeutic intervention point in different malignancies.

The Trk family of RTKs is frequently expressed in lung, breast, pancreatic and prostate cancers as well as in certain type of acute myelogenous leukemia and congenital fibrosarcoma. The tyrosine kinase activity of Trk is believed to promote the unregulated activation of cell proliferation machinery. It is believed that inhibitors of either TrkA, TrkB or TrkC kinases, individually or in combination, have utility against some of the most common cancers such as brain, melanoma, multiple myeloma, squamous cell, bladder, gastric, pancreatic, breast, head, neck, esophageal, prostate, colorectal, lung, renal, ovarian, gynecological, thyroid cancer, and certain type of hematological malignancies.

The Janus kinases (Jaks) modulate proliferation, survival and differentiation of a variety of cell types through integrating the signal transduction mediated by cytokine receptors. The Jak family of tyrosine kinases is comprised of the four family members, Tyk2, Jak1, Jak2 and Jak3. This kinase family shares several structural features including several Jak (JH) homology domains. The carboxy terminal JH1 domain contains the active kinase domain adjacent to a pseudokinase JH2 domain. Amino terminal to these domains are JH3-4 and JH5-7, which encode a domain similar to a SH2 and FERM domains, respectively. The SH2-like domain is not well characterized functionally amongst the Jak family members whereas the FERM domain, comprised of JH5-7, has been shown to mediate binding to cytokine receptors. Cytokine receptors are devoid of an intrinsic kinase activity and upon ligand binding, Jak family members are recruited to these receptors and are activated to phosphorylate tyrosine residues on the receptor complex and to downstream signaling molecules. A key downstream mediator of cytokine receptor signaling is the signal transduction and activator of transcription (STAT) proteins. There are seven mammalian STAT proteins (STAT1, 2, 3, 4, 5a, 5b, 6 and 7) which integrate signaling downstream of cytokine receptor activation. Upon recruitment to the cytokine receptor-Jak complex, STATs are tyrosine phosphorylated at the carboxy terminus by the Jak kinases. This phosphorylation results in the formation of STAT homo- or heterodimers through phosphorylated tyrosine and SH2 domain interactions. After activation through dimerization, the STAT proteins translocate the nucleus where they bind a response element in promoters to activate transcription of key genes involved in proliferation and differentiation. In addition to STAT regulation, Jak activation has also been reported to regulate other key growth/survival pathways including those mediated by IRS-1, Ras-MAPK, PI3K and Src kinase.

Alterations in Jak signal transduction has been reported in a variety of diseases. In leukemias, chromosomal rearrangements (Tel-Jak2) producing a constitutively active Jak kinase have been observed in atypical chronic myeloid leukemia. Activating point mutations have been observed in Jak3 in acute megakaryoblastic leukemia and Jak2 in acute myelogenous leukemia and in myeloproliferative disorders such as polcythaemia vera, essential thrombocythemia and myeloid metaplasia. A role for Jak kinases in solid tumors is also supported by the large number of reports of constitutive Stat3 activation in a wide variety of cancers. Elevated or constitutive STAT3 activity has been observed in breast, prostate, head/neck and melanoma tumor specimens and cell lines with pharmacological or genetic evidence for involvement of Jak activity in the observed STAT3 activation. In addition, Jak signaling has been implicated in malignant transformation through the activation of other key signaling pathways such as PI3K, Src, Bcl2 and Ras-MAPK. The communication of Jak signaling to these key pathways has the potential to broaden the involvement of this kinase family to a wide spectrum of malignancies.

Casein Kinase 2 (CK2) is a serine/threonine kinase that has been implicated in the regulation of stability of a number of oncogenic or tumor suppressor proteins. Proteins such as beta-catenin and c-Myc, that have been established as important components of signaling pathways in cancer cells, have been shown to be phosphorylated by CK2 and these phosphorylation events have been proposed to be required for the stabilization of these proteins. Tumor suppressor proteins, such as PML and PTEN, have also been shown to be phosphorylated by CK2, and these modifications have been suggested to promote degradation of these proteins. Inhibition of CK2 enzymatic activity, such as by small molecules, may lead to the destabilization of oncogene products as well as the stabilization of tumor suppressor proteins, resulting in an anti-proliferative effect on tumor cells.

DETAILED DESCRIPTION OF THE INVENTION

The present invention provides for compounds of formula I, pharmaceutical compositions employing such compounds and for methods of using such compounds.

In accordance with the present invention, there are disclosed compounds of formula I

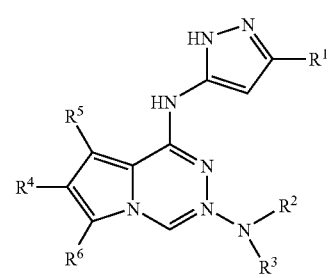

(I)

wherein:
R$^1$ is hydrogen, alkyl, substituted alkyl, cycloalkyl, substituted cycloalkyl, aryl, substituted aryl, —OCH$_2$cycloalkyl, arylalkyl, —COOH or —CONR$^{12}$R$^{13}$;

R$^2$ and R$^3$ are independently hydrogen, alkyl, substituted alkyl, cycloalkyl, substituted cycloalkyl, aryl, substituted aryl, heteroaryl, substituted heteroaryl, heterocyclyl, substituted heterocyclyl, —CO alkyl, —CO substituted alkyl, —COaryl, —CO substituted aryl, —COarylalkyl, —CO substituted heteroaryl, —CO heterocyclyl alkyl, —CO(CH$_2$)$_n$NR$^4$R$^5$, —CONR$^4$R$^5$, —CONHSO$_2$R$^5$, —NHCONHR$^5$, —(CH$_2$)$_n$-aryl, —(CH$_2$)$_n$-substituted aryl, —(CH$_2$)$_n$-substituted heteroaryl, —(CH$_2$)$_2$(CH$_2$)$_n$—OH, —(CH$_2$)$_2$(CH$_2$)$_n$—NH$_2$, —(CH$_2$)$_2$(CH$_2$)$_n$—S-alkyl, —SO$_2$alkyl or —COCF$_3$, two of which may be attached to the same ring carbon atom provided that the resultant compound is chemically stable; or R$^2$ and R$^3$ are taken together with the nitrogen atom to which they are attached to form an optionally substituted 4-8 membered ring, said ring optionally containing one or more additional heteroatoms selected from —N—, —S— and —O—; said substituents on the rings are independently selected from the group consisting of hydrogen, —OH, alkyl, substituted alkyl, cycloalkyl, substituted cycloalkyl, alkoxy, substituted alkoxy, aryl, substituted aryl, arylalkyl, heteroaryl, substituted heteroaryl, heterocyclyl, substituted heterocyclyl, —CONR$^4$R$^5$, —OCONR$^4$R$^5$, —CONHSO$_2$R$^5$, —NHCONR$^4$R$^5$, —NHCOalkyl, —NHCOsubstituted alkyl, —NHCOalkoxyalkyl, —NHCOalkylCOalkoxy, —NHCO(CH$_2$)$_n$NR$^4$R$^5$, NHCO(CH$_2$)$_n$bisphenyl, —NHCOaryl, —NHCOsubstituted aryl, —NHCO arylalkyl, —NHCOsubstituted arylalkyl, —NHCOheteroaryl, —NHCOsubstituted heteroaryl, —NHCOheteroarylalkyl, —NHCOsubstituted heteroarylalkyl, —NHCO(CH$_2$)$_n$CN, —NHCOaminosulfonylalkyl, —NHCO(CH$_2$)$_n$NH$_2$, —NHCOCF$_3$, —NHSO$_2$R$^4$, —CH$_2$OR$^4$, —(CH$_2$)$_n$-aryl, —(CH$_2$)$_n$-substituted aryl, —(CH$_2$)$_n$-substituted heteroaryl, —(CH$_2$)$_n$—OH, —(CH$_2$)$_n$NH$_2$, —(CH$_2$)$_n$S-alkyl;

R$^4$ and R$^5$ are independently hydrogen, alkyl, substituted alkyl, cycloalkyl, substituted cycloalkyl, hydroxyalkyl, dihydroxyalkyl, alkoxy, substituted alkoxy, aryl, substituted aryl, heteroaryl, substituted heteroaryl, halogen, cyano, amino or substituted amino;

R$^6$ is H, C$_1$-C$_6$ alkyl, C$_1$-C$_6$ alkenyl, C$_1$-C$_6$ alkynyl, C$_3$-C$_8$ cycloalkyl, C$_1$-C$_5$ arylalkyl, aryl, substituted aryl, heteroarylalkyl, substituted heteroarylalkyl, heteroaryl, substituted heteroaryl or C$_4$-C$_8$ heterocyclyl with at least one atom on the ring selected from nitrogen or oxygen atom, and each of said $R^6$ groups optionally substituted with 1 to 3 groups selected from the group consisting of —OH, $OR^8$, —$COOR^8$, —$NH_2$, —$NR^8R^9$, —$CONHR^8$, —$OCONHR^8$, —$CONHSO_2R^8$, —$NHCONHR^8$, —$SR^8$, —$S(=O)R^8$, —$SO_2R^8$ and —$SO_2NR^8R^9$;

$R^8$ is $C_1$-$C_6$ alkyl, $C_3$-$C_6$ cycloalkyl, aryl, substituted aryl, heteroaryl or substituted heteroaryl group; said substituents on the substituted aryl or substituted heteroaryl group are one or more hydrogen, halogen, alkyl, substituted alkyl, alkynyl, substituted alkynyl, alkoxy, substituted alkoxy, aryl, substituted aryl, arylalkyl, substituted arylalkyl, aryloxy or substituted aryloxy;

$R^9$ is hydrogen, $C_1$-$C_6$ alkyl or $C_3$-$C_6$ cycloalkyl;

$R^{12}$ and $R^{13}$ are independently hydrogen, alkyl, substituted alkyl, cycloalkyl, substituted cycloalkyl, hydroxyalkyl, dihydroxyalkyl, alkoxy, substituted alkoxy, aryl, substituted aryl, heteroaryl, substituted heteroaryl, halogen, cyano, amino or substituted amino; or $R^{12}$ and $R^{13}$ are taken together with the nitrogen atom to which they are attached to form an optionally substituted 4-8 membered ring, said ring optionally containing one or more additional heteroatoms selected from —N—, —S— and —O—; said substituents on the ring are independently hydrogen, —OH, alkyl, substituted alkyl or hydroxyalkyl;

n is 0, 1, 2, 3 or 4;

or a pharmaceutically acceptable salt or stereoisomer thereof.

In another embodiment, the invention comprises a compound of formula I wherein:

$R^2$ and $R^3$ are taken together with the nitrogen atom to which they are attached to form an optionally substituted piperidinyl or pyrrolidinyl ring.

In another embodiment, the invention comprises a compound of formula II

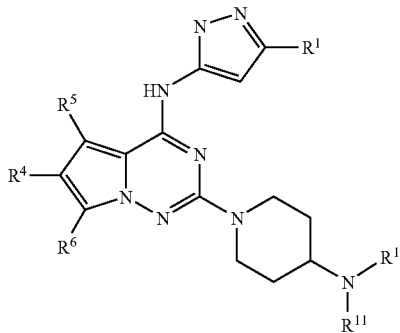

(II)

wherein the symbols have the following meanings and are, for each occurrence, independently selected:

$R^1$ is hydrogen, alkyl, substituted alkyl, cycloalkyl, substituted cycloalkyl, aryl, substituted aryl, —$OCH_2$cycloalkyl, arylalkyl, —COOH or —$CONR^{12}R^{13}$;

$R^{10}$ and $R^{11}$ are independently hydrogen, —OH, alkyl, substituted alkyl, cycloalkyl, substituted cycloalkyl, alkoxy, substituted alkoxy, aryl, substituted aryl, arylalkyl, substituted arylalkyl, heteroaryl, substituted heteroaryl, heterocyclyl, substituted heterocyclyl, —CO alkyl, —CO substituted alkyl, —COaryl, —CO substituted aryl, —COarylalkyl, —CO substituted heteroaryl, —CO heterocyclyl alkyl, —COheteroaryl, —COsubstituted heteroaryl, —COheteroarylalkyl, —COsubstituted heteroarylalkyl, —$CO(CH_2)_nNK^4R^5$, —$CONR^4R^5$, —$CONHSO_2R^5$, —$(CH_2)_n$-aryl, —$(CH_2)_n$-substituted aryl, —$(CH_2)_n$-substituted heteroaryl, —$(CH_2)_2(CH_2)_n$—OH, —$(CH_2)_2(CH_2)_n$—$NH_2$, —$(CH_2)_2(CH_2)_n$—S-alkyl, —$SO_2$alkyl or —$COCF_3$, two of which may be attached to the same ring carbon atom provided that the resultant compound is chemically stable;

$R^4$ and $R^5$ are independently hydrogen, alkyl, substituted alkyl, aryl, substituted aryl, halogen, cyano, amino or substituted amino;

$R^6$ is H, $C_1$-$C_6$ alkyl, $C_1$-$C_6$ alkenyl, $C_1$-$C_6$ alkynyl, $C_3$-$C_8$ cycloalkyl, $C_1$-$C_5$ arylalkyl, aryl, substituted aryl, heteroarylalkyl, substituted heteroarylalkyl, heteroaryl, substituted heteroaryl or $C_4$-$C_8$ heterocyclyl with at least one atom on the ring selected from nitrogen or oxygen atom, and each of said $R^6$ groups optionally substituted with 1 to 3 groups selected from the group consisting of —OH, $OR^8$, —$COOR^8$, —$NH_2$, —$NR^8R^9$, —$CONHR^8$, —$OCONHR^8$, —$CONHSO_2R^8$, —$NHCONHR^8$, —$SR^8$, —$S(=O)R^8$, —$SO_2R^8$ and —$SO_2NR^8R^9$;

$R^8$ is $C_1$-$C_6$ alkyl, $C_3$-$C_6$ cycloalkyl, aryl, substituted aryl, heteroaryl or substituted heteroaryl group; said substituents on the substituted aryl or substituted heteroaryl group are one or more hydrogen, halogen, alkyl, substituted alkyl, alkynyl, substituted alkynyl, alkoxy, substituted alkoxy, aryl, substituted aryl, arylalkyl, substituted arylalkyl, aryloxy or substituted aryloxy;

$R^9$ is hydrogen, $C_1$-$C_6$ alkyl or $C_3$-$C_6$ cycloalkyl;

$R^{12}$ and $R^{13}$ are independently hydrogen, alkyl, substituted alkyl, cycloalkyl, substituted cycloalkyl, hydroxyalkyl, dihydroxyalkyl, aryl, substituted aryl, heteroaryl, substituted heteroaryl, amino or substituted amino; or $R^{12}$ and $R^{13}$ are taken together with the nitrogen atom to which they are attached to form an optionally substituted 4-8 membered ring, said ring optionally containing one or more additional heteroatoms selected from —N—, —S— and —O—; said substituents on the ring are independently hydrogen, —OH, alkyl, substituted alkyl or hydroxyalkyl;

or a pharmaceutically acceptable salt or stereoisomer thereof.

In another embodiment, the invention comprises a compound of formula II wherein:

$R^1$ is hydrogen, alkyl, substituted alkyl, cycloalkyl, substituted cycloalkyl, aryl or substituted aryl.

In another embodiment, the invention comprises a compound of formula III

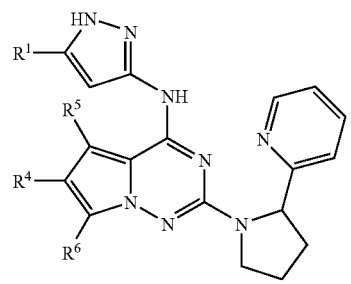

(III)

wherein:
- $R^1$ is hydrogen, alkyl, substituted alkyl, cycloalkyl, substituted cycloalkyl, aryl, substituted aryl, —OCH$_2$cycloalkyl, arylalkyl, —COOH or —CONR$^{12}$R$^{13}$;
- $R^4$ and $R^5$ are independently hydrogen, alkyl, substituted alkyl, aryl, substituted aryl, halogen, cyano, amino or substituted amino;
- $R^6$ is H, $C_1$-$C_6$ alkyl, $C_1$-$C_6$ alkenyl, $C_1$-$C_6$ alkynyl, $C_3$-$C_8$ cycloalkyl, $C_1$-$C_5$ arylalkyl, aryl, substituted aryl, heteroarylalkyl, substituted heteroarylalkyl, heteroaryl, substituted heteroaryl or $C_4$-$C_8$ heterocyclyl with at least one atom on the ring selected from nitrogen or oxygen atom, and each of said $R^6$ groups optionally substituted with 1 to 3 groups selected from the group consisting of —OH, OR$^8$, —COOR$^8$, —NH$_2$, —NR$^8$R$^9$, —CONHR$^8$, —OCONHR$^8$, —CONHSO$_2$R$^8$, —NHCONHR$^8$, —SR$^8$, —S(=O)R$^8$, —SO$_2$R$^8$ and —SO$_2$NR$^8$R$^9$;
- $R^8$ is $C_1$-$C_6$ alkyl, $C_3$-$C_6$ cycloalkyl, aryl, substituted aryl, heteroaryl or substituted heteroaryl group; said substituents on the substituted aryl or substituted heteroaryl group are one or more hydrogen, halogen, alkyl, substituted alkyl, alkynyl, substituted alkynyl, alkoxy, substituted alkoxy, aryl, substituted aryl, arylalkyl, substituted arylalkyl, aryloxy or substituted aryloxy;
- $R^9$ is hydrogen, $C_1$-$C_6$ alkyl or $C_3$-$C_6$ cycloalkyl;
- $R^{12}$ and $R^{13}$ are independently hydrogen, alkyl, substituted alkyl, cycloalkyl, substituted cycloalkyl, hydroxyalkyl, dihydroxyalkyl, aryl, substituted aryl, heteroaryl, substituted heteroaryl, amino and substituted amino; or
- $R^{12}$ and $R^{13}$ are taken together with the nitrogen atom to which they are attached to form an optionally substituted 4-8 membered ring, said ring optionally containing one or more additional heteroatoms selected from —N—, —S— and —O—; said substituents on the ring are independently hydrogen, —OH, alkyl, substituted alkyl or hydroxyalkyl;
- or a pharmaceutically acceptable salt or stereoisomer thereof

DEFINITIONS

The following are definitions of terms that may be used in the present specification. The initial definition provided for a group or term herein applies to that group or term throughout the present specification individually or as part of another group, unless otherwise indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. SO$_2$NH$_2$, substituted sulfonamido, nitro, cyano, carboxy, carbamyl, e.g. CONH$_2$, substituted carbamyl e.g. CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethen-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclyl" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, thienothienyl, and the like.

Exemplary substituents include one or more alkyl or arylalkyl groups as described above or one or more groups described above as alkyl substituents.

Also included are smaller heterocyclyls, such as, epoxides and aziridines.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The term "alkylsulfone" refers to —$R^kS(=O)_2R^k$, wherein $R^k$ is an alkyl or substituted alkyl.

The term "oxo" refers to the divalent radical =O.

The term "carbamate" refers to the group —OC(=O)NH$_2$.

The term "amide" refers to the group —C(=O)NH$_2$.

The term "sulfonamide" refers to the group —SO$_2$NH$_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group —C(=O)NR$'''$R$''$ wherein R$'''$ and R$''$ are independently selected from H, alkyl, substituted alkyl, alkenyl, substituted alkenyl, cycloalkyl, and substituted cycloalkyl, provided at least one of R$'''$ or R$''$ is a substituted moiety.

A substituted sulfonamide, for example, refers to the group —SO$_2$NR$^o$R$^p$ wherein R$^o$ and R$^p$ are independently selected from alkyl, substituted alkyl, alkenyl, substituted alkenyl, cycloalkyl, and substituted cycloalkyl, provided at least one of R$^o$ or R$^p$ is a substituted moiety.

A substituted carbamate, for example, refers to the group —OC(=O)NR$^q$R$^r$ wherein R$^q$ and R$^r$ are independently selected from alkyl, substituted alkyl, alkenyl, substituted alkenyl, cycloalkyl, and substituted cycloalkyl, provided at least one of R$^q$ or R$^r$ is a substituted moiety.

The term "ureido" refers to the group —NHC(=O)NH$_2$.

The term "cyano" refers to the group —CN.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group —N(O)$_2$.

The term "thio" refers to the group —SH.

The term "alkylthio" refers to the group —SK$^s$ where R$^s$ is an alkyl, substituted alkyl, cycloalkyl, or substituted cycloalkyl.

The term "thioalkyl" refers to the group —R$'$S where R$^t$ is an alkyl, substituted alkyl, cycloalkyl, or substituted cycloalkyl.

The term "alkylsulfonyl" refers to the group —S(=O)$_2$R$^u$ where R$^u$ is an alkyl, substituted alkyl, cycloalkyl, or substituted cycloalkyl.

The term "alkylsulfinyl" refers to the group —S(=O)R$^v$ where R$^v$ is an alkyl, substituted alkyl, cycloalkyl, or substituted cycloalkyl.

The term "carboxy" refers to the group —C(=O)OH.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group —C(=O)OR$^w$ where R$^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group —OC(=O)R$^x$, where R$^x$ is an alkyl or substituted alkyl, or an aryl or substituted aryl, respectively.

The term "carbamoyl" refers to the groups —OC(=O)NH$_2$, —OC(=O)NHR$^x$, and/or —OC(=O)NR$^y$R$^z$, wherein R$^y$ and R$^z$ are independently selected from alkyl and substituted alkyl.

The group —NR$^6$(C=O)R$^9$ refers to a group where R$^6$ is selected from hydrogen, lower alkyl and substituted lower alkyl, and R$^9$ is selected from hydrogen, alkyl, substituted alkyl, alkoxy, aminoalkyl, substituted aminoalkyl, alkylamino, substituted alkylamino, aryl and substituted aryl.

The term "carbonyl" refers to a C(=O).

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group S(=O)$_2$.

The term "sulfinyl" refers to an S(=O).

The term "carboxyalkyl" refers to an alkyl or substituted alkyl bonded to a carboxy.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:
 a) *Design of prodrugs*, edited by H. Bundgaard, (Elsevier, 1985) and *Methods in Enzymology*, Vol. 112, pp. 309-396, edited by K. Widder, et al. (Academic Press, 1985);
 b) *A Textbook of Drug Design and Development*, edited by Krosgaard-Larsen and H. Bundgaard, Chapter 5, "Design and Application of Prodrugs," by H. Bundgaard, pp. 113-191 (1991); and
 c) H. Bundgaard, *Advanced Drug Delivery Reviews*, 8, 1-38 (1992).

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination. "Therapeutically effective amount" is also intended to include an amount of the combination of compounds claimed that is effective to inhibit Trk related diseases and/or conditions. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

Utility

The present invention is based on the discovery that certain pyrrolotriazines are inhibitors of protein kinases. More specifically, pyrrolotriazines such as those described in this invention inhibit the protein tyrosine kinase activity of members of the TRK and Jak family of receptors as well as Src. Pyrrolotriazines such as those described in this invention also inhibit the protein serine/threonine kinase activity of members of the CK2 family of receptors. These inhibitors will be useful in the treatment of proliferative diseases that are dependent on signaling by one or more of these receptors. Such diseases include solid tumors of the pancreatic, prostate, lung, head and neck, breast, colon, ovary, as well as other tumor types including multiple myeloma, melanoma, neuroblastoma, gliobalstoma and hematological malignancies such as acute myelogenous leukemia.

The invention also relates to a pharmaceutical composition of compound of formula I, or pharmaceutically acceptable salt thereof, and a pharmaceutically acceptable carrier in the treatment of hyperproliferative disorder in mammal. In particular, said pharmaceutical composition is expected to inhibit the growth and/or metastasis of those primary and recurrent solid tumors which are associated with TrkA, TrkB, TrkC, Flt-3 (Fms-like kinase-3), Jak2, Jak3, Src and Tie-2, especially those tumors which are significantly dependent on TrkA, TrkB, TrkC, Flt-3, Tie-2 for their growth and spread, including for example, cancers of the thyroid, breast, colon, pancreas, or a variety of tumor types including multiple myeloma, melanoma, neuroblastoma, glioblastoma and acute myelogenous leukemia.

Thus according to a further aspect of the invention there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

By virtue of their ability to inhibit TrkA, TrkB, TrkC, Flt-3, Jak2, Jak3, Src, CK2 and Tie-2 kinases, compounds of the present invention can be used for the treatment of proliferative diseases, including cancer. The TrkA, TkB and TrkC receptor kinases have been shown to be expressed and activated in tumors including thyroid, breast, colon, acute myelogenous leukemia and elevated Trk receptors and corresponding ligands have also been reported in a variety of tumor types including multiple myeloma, melanoma, pancreatic acnrcinoma, neuroblastoma and glioblastoma. It is therefore expected that inhibitors of the TrkA, TrkB and TrkC kinases will have efficacy in the treatment of tumors that depend on signaling from either or both of the two receptors. These compounds are expected to have efficacy either as single agent or in combination (simultaneous or sequentially) with other chemotherapeutic agents such as Taxol®, adriamycin, and cisplatin.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecules such as ZD6474 and SU6668; Vatalanib, BAY-43-9006, SU11248, CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g. Gleevec® and dasatinib (Sprycel®); Casodex® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof, CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the present invention are of interest for their antiproliferative effects.

Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medulloblastoma;

hematological malignancies such as acute myelogenous leukemia (AML), and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease.

The compounds of formula I are especially useful in treatment of tumors having a high incidence of tyrosine kinase activity, such as prostate, colon, brain, thyroid and pancreatic tumors. By the administration of a composition (or a combination) of the compounds of this invention, development of tumors in a mammalian host is reduced.

Compounds of formula I may also be useful in the treatment of other cancerous diseases (such as acute myelogenous leukemia) that may be associated with signal transduction pathways operating through kinases such as Flt-3 (Fine-like kinase-3), Tie-2, CDK2, VEGFR, FGFR and IGFR kinases.

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

Biological Assays

TrkA

The ability of compounds of the present invention to inhibit tyrosine kinase activity of TrkA may be measured using a recombinant enzyme in an assay that measures the ability of compounds to inhibit the phosphorylation of the exogenous substrate, polyGluTyr (PGT, 4:1). The kinase domain of the human TrkA receptor is expressed in Sf9 insect cells as a histidine (His)-fusion protein using a baculovirus expression system. The protein is purified from the lysates of these cells using an Ni—NTA affinity column. After the recombinant enzyme is purified, it is activated by incubation with cold ATP. The enzyme assay is performed in a 96-well plate. Test compounds are first dissolved in dimethylsulfoxide (DMSO) and then serially-diluted in a 96-well plate. The serially-diluted compounds are transferred to the 96-well assay plate so that the final concentration of DMSO in the enzyme assay is 1.64%. All assay components are diluted in phosphorylation buffer (20 mm MOPS, 10 mM $MgCl_2$, 1 mM EDTA, 0.015% Brij-35, 01 mg/ml BSA, 0.0025% Beta-Mercaptoethanol). The recombinant enzyme is added to the assay plate containing test compound and the reaction is initiated with a substrate solution containing a final concentration of 0.1 mg/ml PGT, 30 uM ATP, and 0.008 mCi/ml $^{33}$P-gammaATP (3000 Ci/mmol). After a 1 hour incubation at 30° C., the reaction is terminated with 10% TCA and incubated at 4° C. for 1 hour. The reaction is filtered onto a Unifilter® GF/C™ filter plate that has been presoaked with 0.1M NaPyrophosphate. Microscint-20 is then added to the dried filter plate and the captured $^{33}$P-phosphorylated PGT is quantitated on a microscintillation plate counter (TopCount.NXT™). Inhibition of the kinase enzymatic activity by the test compound is detected by a reduction in scintillation, and the concentration of compound that is required to inhibit the signal by 50% is reported as the $IC_{50}$ value for the test compound.

TrkB

The ability of compounds of the present invention to inhibit tyrosine kinase activity of TrkB may be measured using a recombinant enzyme in an assay that measures the ability of compounds to inhibit the phosphorylation of the exogenous substrate, polyGluTyr (PGT, 4:1). The kinase domain of the human TrkB receptor (amino acids 526-838) is expressed in insect cells as a histidine (His)-fusion protein and is commercially available from Invitrogen™. The enzyme assay is performed in a 96-well plate. Test compounds are first dissolved in dimethylsulfoxide (DMSO) and then serially-diluted in a 96-well plate. The serially-diluted compounds are transferred to the 96-well assay plate so that the final concentration of DMSO in the enzyme assay is 1.64%. All assay components are diluted in phosphorylation buffer (20 mm MOPS, 10 mM $MgCl_2$, 1 mM EDTA, 0.015% Brij-35, 0.1 mg/ml BSA, 0.0025% Beta-Mercaptoethanol). The recombinant enzyme is added to the assay plate containing test compound and the reaction is initiated with a substrate solution containing a final concentration of 0.1 mg/ml PGT, 30 uM ATP, and 0.008 mCi/ml $^{33}$P-gammaATP (3000 Ci/mmol). After a 1 hour incubation at 30° C., the reaction is terminated with 10% TCA and incubated at 4° C. for 1 hour. The reaction is filtered onto a Unifilter® GF/C™ filter plate that has been pre-soaked with 0.1M NaPyrophosphate. Microscint-20 is then added to the dried filter plate and the captured $^{33}$P-phosphorylated PGT is quantitated on a microscintillation plate counter (TopCount.NXT™). Inhibition of the kinase enzymatic activity by the test compound is detected by a reduction in scintillation, and the concentration of compound that is required to inhibit the signal by 50% is reported as the $IC_{50}$ value for the test compound.

Compounds described herein were tested in the TrkA and TrkB assays described above. The following results were obtained.

| Compound | Kinase Activity (IC$_{50}$, µM) | |
|---|---|---|
| | TrkA | TrkB |
| 8 | 0.0003 | 0.0003 |
| 43 | 0.0004 | 0.0005 |
| 49 | 0.0009 | 0.0006 |
| 3 | 0.0006 | 0.002 |
| 18 | 0.0008 | 0.001 |
| 39 | 0.001 | 0.0007 |
| 14 | 0.001 | 0.003 |
| 91 | 0.005 | 0.010 |
| 75 | 0.005 | 0.009 |
| 19 | 0.009 | 0.020 |
| 70 | 0.023 | 0.038 |
| 95 | 0.023 | 0.049 |
| 97 | 0.024 | 0.048 |
| 21 | 0.056 | 0.086 |
| 74 | 0.120 | 0.195 |
| 4 | 0.123 | 0.312 |

JAK2 Tyrosine Kinase Assay

The assays were performed in V-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM MgCl$_2$, 25 mM Beta-Glycerolphosphate, 0.015% Brij35 and 4 mM DTT). The reaction was initiated by the combination of JAK2 with substrates and test compounds. The reaction was incubated at room temperature for 60 min. and terminated by adding 45 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; JAK2 fluorescent peptide, 1.5 µM; JAK2, 1 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations, each in duplicate. IC$_{50}$ values were derived by non-linear regression analysis JAK3 Tyrosine Kinase Assay The assays were performed in V-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM MgCl$_2$, 25 mM Beta-Glycerolphosphate, 0.015% Brij35 and 4 mM DTT). The reaction was initiated by the combination of JAK3 with substrates and test compounds. The reaction was incubated at room temperature for 60 min. and terminated by adding 45 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 8 µM; JAK3 fluorescent peptide, 1.5 µM; JAK3, 2.5 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations, each in duplicate. IC$_{50}$ values were derived by non-linear regression analysis SRC Tyrosine Kinase Assay The assays were performed in V-bottom 384-well plates. The final assay volume was 30 µl prepared from 15 µl additions of enzyme and substrates (fluoresceinated peptide and ATP) and test compounds in assay buffer (20 mM HEPES pH 7.4, 10 mM MnCl$_2$, 0.015% Brij35 and 4 mM DTT). The reaction was initiated by the combination of SRC with substrates and test compounds. The reaction was incubated at room temperature for 60 min. and terminated by adding 45 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reaction for 100% inhibition and vehicle-only reactions for 0% inhibition. The final concentration of reagents in the assays is ATP, 20 µM; SRC fluorescent peptide, 1.5 µM; SRC, 0.6 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations, each in duplicate. IC$_{50}$ values were derived by non-linear regression analysis

| Compound | Kinase Activity (IC$_{50}$, µM) | | |
|---|---|---|---|
| | Jak2 | Jak3 | Src |
| 100 | 0.005 | 0.024 | 0.105 |
| 101 | 0.004 | 0.02 | 0.0677 |
| 102 | 0.107 | 0.449 | 1.16 |
| 107 | 0.049 | 0.026 | 0.053 |
| 108 | 0.083 | 0.063 | 0.65 |
| 109 | 2.9 | 3.1 | 5.6 |
| 112 | 2.32 | 7.22 | 38.52 |
| 113 | 0.0008 | ND | 0.066 |
| 114 | 0.01 | ND | 0.78 |
| 118 | 0.063 | 0.322 | 0.775 |
| 119 | 0.096 | 0.52 | 0.931 |
| 122 | 0.004 | 0.016 | 0.081 |
| 123 | 0.01 | 0.005 | 0.33 |
| 127 | 8.54 | 22.31 | 31.11 |
| 128 | 0.009 | 0.02 | 0.72 |
| 130 | 40 | 40 | 40 |
| 137 | 15.66 | 45.01 | 50 |
| 139 | 2.05 | 4.48 | 7.62 |
| 140 | 2.38 | 2.97 | 1.55 |
| 143 | 3.43 | 8.66 | 7.49 |
| 144 | 0.09 | 0.11 | 0.75 |
| 145 | 0.02 | 0.009 | 0.24 |
| 148 | 0.08 | 0.13 | 1.18 |
| 152 | 0.01 | 0.02 | 0.9 |
| 153 | 0.02 | 0.006 | 0.72 |
| 154 | 0.08 | 0.13 | 1.18 |
| 156 | 0.07 | 0.11 | 1.21 |
| 159 | 0.01 | 0.005 | 0.11 |
| 167 | 0.001 | 0.004 | 0.14 |
| 169 | 0.01 | 0.04 | 0.09 |
| 170 | 0.001 | 0.017 | 0.42 |

CK2A1

Incubation mixtures employed for the Casein Kinase 2 A1 kinase assay contain Casecin Kinase 2 A1 kinase, a synthetic peptide substrate, ATP, ATP-γ-$^{33}$P and a Hepes buffer containing Mg$^{2+}$, NaCl, DTT, and Brij-35. Reactions were incubated for 60 minutes at 30° C. and stopped by the addition of trichloroacetic acid (TCA) to a final concentration 8%. TCA precipitates were collected onto GF/C unifilter plates using a Filtermate universal harvester and the filters are quantitated using a TopCount 96/384-well liquid scintillation counter. Dose response curves were generated to determine the concentration required to inhibit 50% of kinase activity (IC$_{50}$).

Compounds were dissolved at 10 mM in dimethyl sulfoxide (DMSO) and evaluated at ten concentrations, each in duplicate. The final concentration of DMSO in the assay is 1.7%. $IC_{50}$ values were derived by non-linear regression.

CK2A2

Incubation mixtures employed for the Casein Kinase 2 A2 kinase assay contain Casein Kinase 2 A2 kinase, a synthetic peptide substrate, ATP, ATP-$\gamma^{33}$P and a Hepes buffer containing $Mg^{++}$, NaCl, DTT, and Brij-35. Reactions were incubated for 60 minutes at 30° C. and stopped by the addition of trichloroacetic acid (TCA) to a final concentration 8%. TCA precipitates were collected onto GF/C unifilter plates using a Filtermate universal harvester and the filters are quantitated using a TopCount 96/384-well liquid scintillation counter. Dose response curves were generated to determine the concentration required to inhibit 50% of kinase activity ($IC^{50}$). Compounds were dissolved at 10 mM in dimethyl sulfoxide (DMSO) and evaluated at ten concentrations, each in duplicate. The final concentration of DMSO in the assay is 1.7%. $IC_{50}$ values were derived by non-linear regression.

Table of CK2 Activity

| Example | Kinase Activity ($IC_{50}$, µM) | |
|---|---|---|
| | CK2A1 | CK2A2 |
| 181 | 0.084 | 0.006 |
| 171 | 0.154 | 0.011 |
| 184 | 0.177 | 0.014 |
| 182 | 0.131 | 0.013 |
| 201 | 0.159 | 0.025 |
| 186 | 0.294 | 0.039 |
| 213 | 0.349 | 0.043 |
| 203 | 0.243 | 0.056 |
| 176 | 0.872 | 0.089 |
| 174 | 0.670 | 0.091 |
| 212 | 1.382 | 0.099 |
| 204 | 1.859 | 0.228 |
| 199 | 2.345 | 0.379 |
| 209 | 6.07 | 1.095 |
| 197 | 11.3 | 1.023 |

Abbreviations

The following abbreviations may be employed in the methods of preparation and Examples:
h=hours
DCM=dichloromethane
THF=tetrahydrofuran
HPLC=high performance liquid chromatography
DIEA=diisopropylethyl amine
i-PrOH=isopropyl alcohol
TFA=trifluoroacetic acid
min=minutes
DMF=dimethylformamide
EDC=N-(3-Dimethylaminopropyl)N'-ethylcarbodiimide
HOBt=hydroxybenzotriazole
NMP=N-methylpyrrolidinone
EtOAc=ethyl acetate
AcOH=acetic acid
BOP reagent=benzotriazole-1-yl-oxy-tris-(dimethylamino)-phasphoniumhexafluorophosphate
brine=saturated aqueous sodium chloride solution
$Et_3N$=triethylamine
$t_R$=retention time Methods of Preparation Compounds of formula I may generally be prepared according to the following schemes and the knowledge of one skilled in the art.

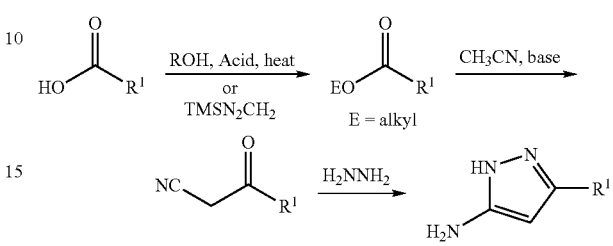

Amino pyrazoles may be prepared according to Scheme 1. An appropriately substituted carboxylic acid may be esterified using acid catalysis and heat or through the use of an esterification reagent such as $TMSCH_2N_2$. Condensation with acetonitrile under basic conditions afford α-cyano ketones that may be cyclized to the pyrazoles using hydrazine.

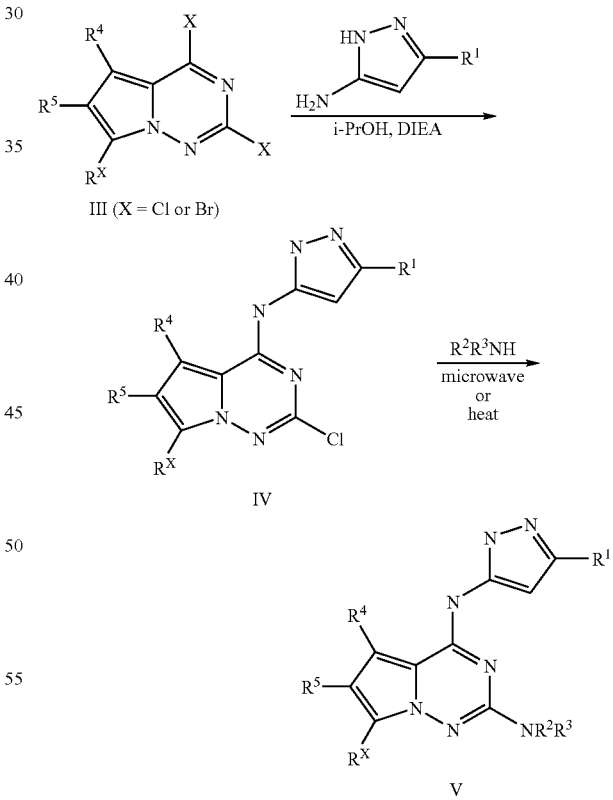

A suitable dihalo-pyrrolotriazine III may be treated with an appropriately substituted amino pyrazole in a suitable solvent such as isopropanol in the presence of a based such as diisopropylethylamine to afford compounds of general formula IV. The second halogen may be displaced by amines either thermally or under microwave conditions using either the amine or dimethylformamide or dimethylacetamide as solvent, in the presence or absence of a transition metal catalyst such as Pd and a phosphorous-based ligand, to afford compounds of formula V.

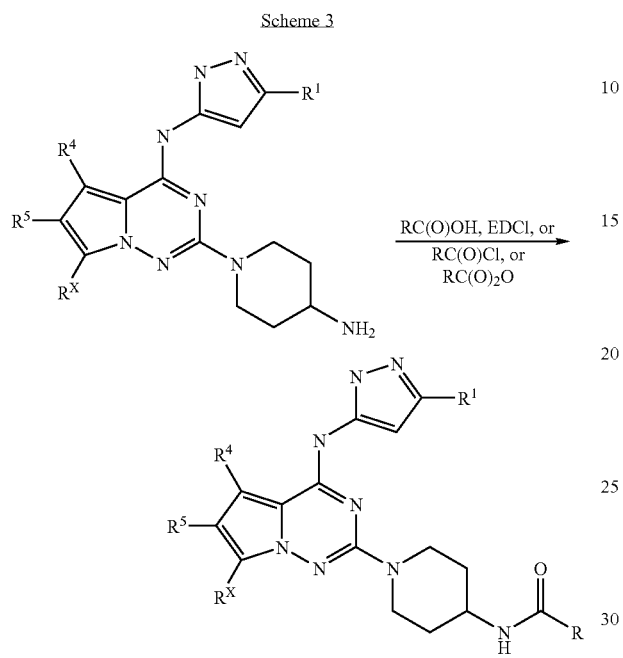

Compounds of formula V, where $R^2$ and $R^3$ form a substituted ring, may be further elaborated as shown in Scheme 3. Amides may be prepared using standard coupling conditions (EDCI) or through the coupling of acid chlorides, anhydrides, among other routes.

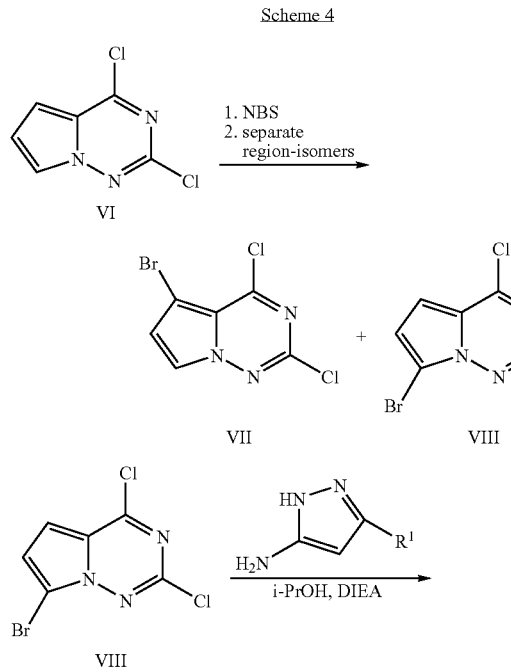

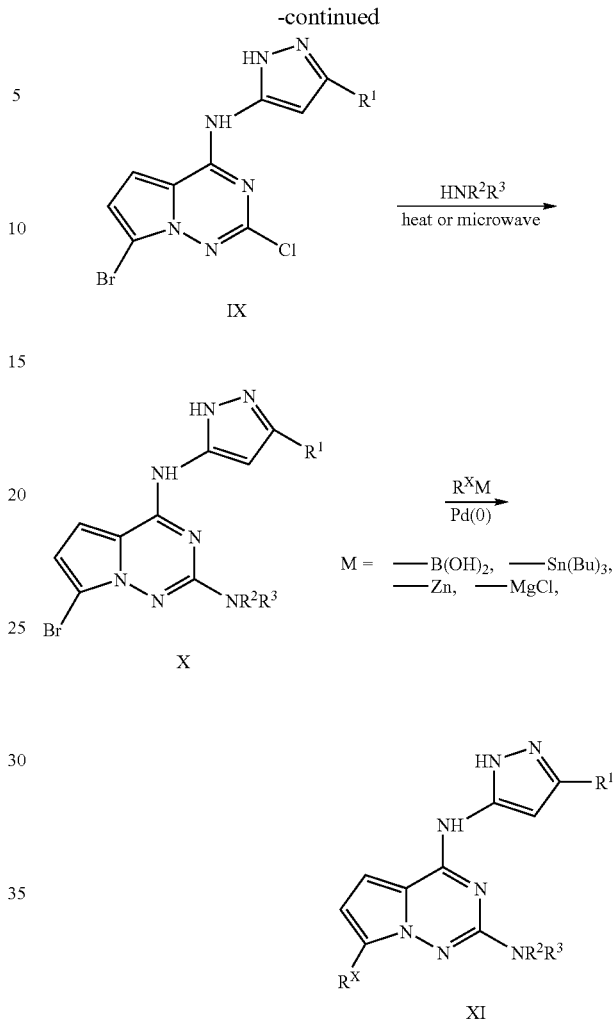

Compounds of formula XII, where $R^x$ is aryl or heteroaryl or alkyl may be synthesized using a general methodology as shown in Scheme 4. Bromination of intermediate VI would give two region-isomeric bromides (VII and VIII). Regioisomer VIII may be treated with suitably substituted pyrazole to afford IX. The second halogen may be displaced by amines either thermally or under microwave conditions using either the amine or dimethylformamide or dimethylacetamide as solvent, in the presence or absence of a transition metal catalyst such as Pd and a phosphorous-based ligand, to afford compounds of formula X. Transition metal promoted coupling of the bromide with suitably activated Rx maybe carried out to give XI.

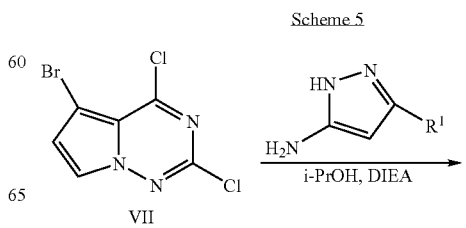

-continued

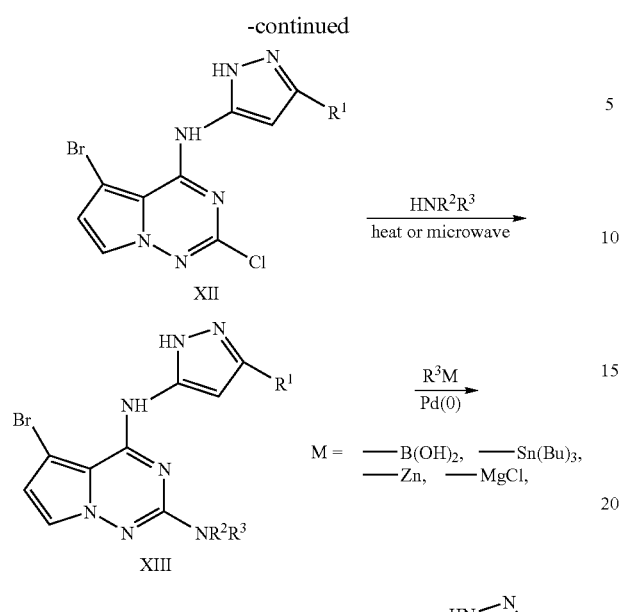

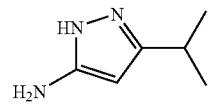

Similarly, regioisomer VII may be converted into compound of general formula XIV using protocol as described in Scheme 5.

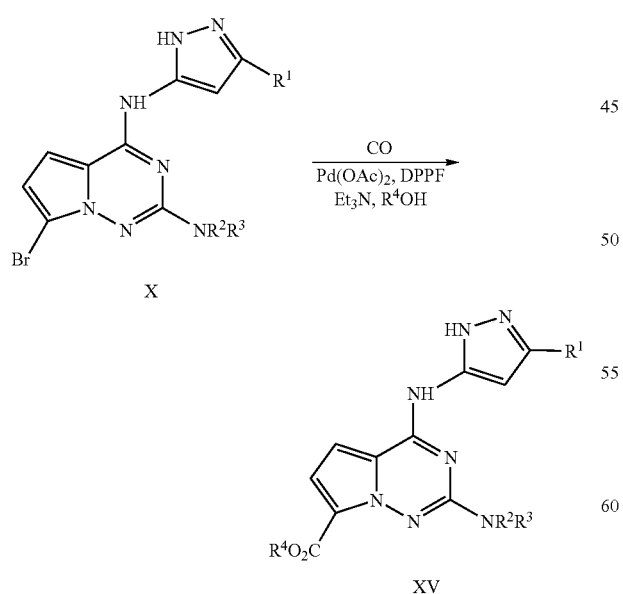

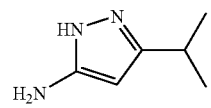

Compounds of formula XV, where R$^x$ is COOR$^4$ may be synthesized using a general methodology as shown in Scheme 6. Bromide X (Scheme 4) could be converted into ester (XVI) using transition metal catalyzed carbonylation.

PREPARATIVE EXAMPLE 1

3-Isopropyl-1H-pyrazol-5-amine

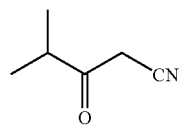

Method One

1A. Preparation of 4-methyl-3-oxopentanenitrile

A suspension of NaH (60% dispersion in mineral oil, 1.05 g, 0.026 mol) in 1,4-dioxane (20 mL), was treated with CH$_3$CN (1.5 mL, 0.028 mol). The reaction mixture was stirred at ambient temperature for 20 minutes, then ethyl isobutyrate (3 mL, 0.023 mol) was added. The reaction mixture was heated to 55° C. for 4 h, and then cooled to ambient temperature and stirred overnight. Water (40 mL) was added at 0° C., and the unreacted starting material was extracted with DCM (50 mL). The aqueous layer was acidified with 1N HCl to pH ~5 and then extracted with DCM (2×50 mL). The combined organic layers were dried (Na$_2$SO$_4$), filtered and concentrated to afford the desired product (1.8 g, 67%). $^1$HNMR (400 MHz, CD$_3$OD) δ 3.52 (s, 1H), 2.72-2.80 (m, 1H), 1.14 (d, J=6.8 Hz).

2B. Preparation of 3-isopropyl-1H-pyrazol-5-amine

To a mixture of 4-methyl-3-oxopentanenitrile (0.9 g, 0.008 mole) in ethyl alcohol (5 mL) was added hydrazine (0.25 mL, 0.008 mole). The reaction mixture was refluxed for 1 hour and then cooled to room temperature. The reaction mixture was concentrated and the residue was dissolved in MeOH (2 mL). The crude product was loaded on a sulfuric acid bound resin (AG 50W-X2, hydrogen form, 100-200 mesh, BioRad), washed with MeOH (50 mL), then washed with 2N NH$_3$ in methanol (10 mL). The ammonia washes were combined and concentrated to afford the desired product (700 mg, 68%). ¹HNMR (400 MHz, MeOD) δ 5.44 (s, 1H), 2.84-2.90 (m, 1H), 1.24 (d, J=6.4 Hz).

PREPARATIVE EXAMPLE 2

3-Ethyl-1H-pyrazol-5-amine

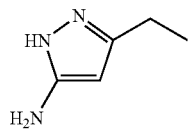

Method Two

2A. Preparation of 3-oxopentanenitrile

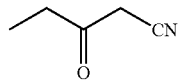

A solution of n-BuLi (1.6 M in Hexane, 5 mL, 8 mmol) in THF (15 mL) at −78° C. was treated with CH₃CN (0.4 mL, 8 mmol). The reaction mixture was stirred at −78° C. for 1 h, and then ethyl propionate (0.45 mL, 4 mmol) was added. The reaction mixture was stirred at −40° C. for 2 h, then slowly warmed to room temperature. The reaction was quenched with 1N HCl and brought to pH~5. The solution was extracted with diethyl ether (20 mL), dried (Na₂SO₄), then carefully concentrated under reduced pressure below 20° C. The crude product (0.4 g) was used in the next step without purification.

2B. Preparation of 3-ethyl-1H-pyrazol-5-amine

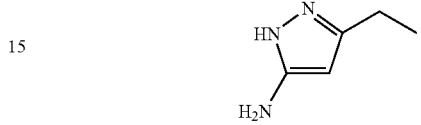

To a mixture of 3-oxopentanenitrile in ethanol (5 mL), was added hydrazine (0.2 mL, 6 mmol). The mixture was refluxed for 1 h, and then concentrated under reduced pressure. The residue was diluted with methanol (1 mL) and purified by preparative reversed-phase HPLC (YMC ODS-A 5 um 30×100 mm, 10-90% aqueous methanol containing 0.1% TFA, 15 min gradient, monitored at 220 nm) to give 3-ethyl-1H-pyrazol-5-amine (0.3 g, 68%). ¹HNMR (MeOD) δ 5.54 (s, 1H), 2.60 (q, 2H, J=7.6 Hz), 1.25 (t, 3H, J=7.6 Hz).

The compounds listed in Table 1 were prepared as described for Preparative Examples 1 or 2 as indicated.

TABLE 1

| # | R | Compound name | Method | HPLC Ret Time (min) |
|---|---|---|---|---|
| A | Et | 3-ethyl-1H-pyrazol-5-amine | 2 | 1.28[a] |
| B | i-Pr | 3-isopropyl-1H-pyrazol-5-amine | 1 | 1.11[a] |
| C | s-Bu | 3-sec-butyl-1H-pyrazol-5-amine | 2 | 0.76[a] |
| D | i-Bu | 3-isobutyl-1H-pyrazol-5-amine | 2 | 0.68[a] |
| E | c-Bu | 3-cyclobutyl-1H-pyrazol-5-amine | 2 | 0.56[a] |
| F | Benzyl | 3-benzyl-1H-pyrazol-5-amine | 1 | 1.75[a] |
| G | cyclopropylmethyl | 3-(cyclopropylmethyl)-1H-pyrazol-5-amine | 2 | 0.65[a] |
| H | trans-2-methylcyclopropyl | 3-(trans-2-methylcyclopropyl)-1H-pyrazol-5-amine | 2 | 0.76[a] |
| I | trans-2-phenylcyclopropyl | 3-(trans-2-phenylcyclopropyl)-1H-pyrazol-5-amine | 2 | 1.82[b] |

TABLE 1-continued

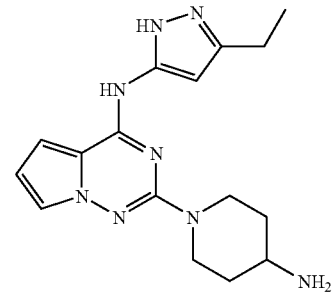

| # | R | Compound name | Method | HPLC Ret Time (min) |
|---|---|---|---|---|
| J | ![cyclopropyl] | 3-(1-methylcyclopropyl)-1H-pyrazol-5-amine | 2 | 0.62[a] |

HPLC Conditions:
[a] YMC S5 Combiscreen ODS 4.6 × 50 mm, 10-90% aqueous methanol containing 0.2% $H_3PO_4$, 4 min gradient, monitored at 220 or 254 nm)
[b] Chromolith SpeedROD 4.6 × 50 mm, 10-90% aqueous methanol containing 0.1% TFA, 4 min gradient, monitored at 220 or 254 nm)

EXAMPLES

Example 1

2-(4-Amino-1-piperidinyl)-N-(3-ethyl-1H-pyrazol-5-yl)pyrrolo[2,1-f][1,2,4]triazin-4-amine

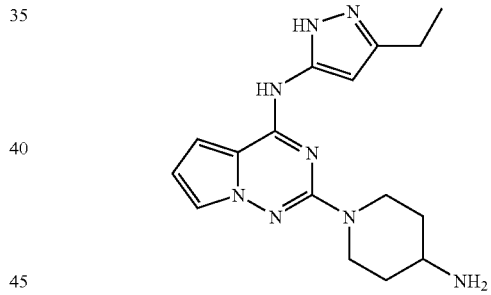

1A. Preparation of 2-chloro-N-(3-ethyl-1H-pyrazol-5-yl)pyrrolo[1,2-f][1,2,4]triazin-4-amine

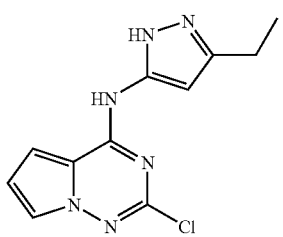

To a mixture of 3-ethyl-1H-pyrazol-5-amine (100 mg, 0.9 mmol) in isopropylalcohol (1 mL), was added 2,4-dichloropyrrolo[1,2-f][1,2,4]triazine (120 mg, 0.64 mmol) and DIEA (0.1 mL, 0.64 mmol). The reaction mixture was stirred at room temperature overnight. The precipitated product was filtered and washed with cold i-PrOH. The solid was dried under $N_2$ overnight to give the title compound. (118 mg, 71%). $^1$HNMR (400 MHz, MeOD), δ 7.60 (s, 1H), 7.03 (s, 1H), 6.72 (s, 1H), 6.61 (s, 1H), 2.73 (q, 2H, J=7.6 Hz), 1.33 (t, 3H, J=7.6 Hz). HPLC $R_t$=2.90 min. (Chromolith SpeedROD 4.6×50 mm, 10-90% aqueous methanol containing 0.1% TFA, 4 min gradient, monitored at 220). m/z=263.27 (M+H).

1B. Preparation of 2-(4-amino-1-piperidinyl)-N-(3-ethyl-1H-pyrazol-5-yl)pyrrolo[2,1-f][1,2,4]triazin-4-amine In a microwave vial (10 mL), 2-chloro-N-(3-ethyl-1H-pyrazol-5-yl)pyrrolo[1,2-f][1,2,4]triazin-4-amine (35 mg, 0.13 mmol) was dissolved in 4-aminopiperidine (0.3 mL). The mixture was heated at 90° C. for 30 minutes using 300 W continuous power. The reaction mixture was diluted with methanol (1 mL) and purified with preparative reversed-phase HPLC (YMC ODS-A 20×100 mm, 10-90% aqueous methanol containing 0.1% TFA, 20 min gradient, monitored at 220 nm) to give the title compound (28 mg, 67%). $^1$HNMR (DMSO-$d_6$) □ 10.34 (s, 1H), 7.89 (s, 3H), 7.42 (s, 1H), 7.08 (s, 1H), 6.48 (s, 1H), 6.45 (m, 1H), 4.42 (d, 2H, J=12.0 Hz), 3.31 (br s, 1H), 2.92 (q, 2H, J=12.0 Hz), 2.64 (q, 2H, J=8.0 Hz), 1.92 (d, 2H, J=8.0 Hz), 1.51 (m, 2H), 1.22 (t, 3H, J=8.0 Hz). HPLC(a) $R_t$=1.85 min. (Chromolith SpeedROD 4.6×50 mm, 10-90% aqueous methanol containing 0.1% TFA, 4 min gradient, monitored at 220). m/z=327.32 (M+H).

Examples 2 to 22

The following compounds in Table 2 have been synthesized utilizing the procedures described in Example 1.

TABLE 2

| Ex. No. | R¹ | R² | R³ | Compound name | [M + H] | HPLC Ret Time (min) |
|---|---|---|---|---|---|---|
| 2 | Me | H | H | 2-(4-amino-1-piperidinyl)-N-(5-methyl-1H-pyrazol-3-yl)pyrrolo[2,1-f][1,2,4]triazin-4-amine | 313.29 | 1.688[a] |
| 3 | cyclopropyl | H | H | 2-(4-amino-1-piperidinyl)-N-(3-cyclopropyl-1H-pyrazol-5-yl)pyrrolo[2,1-f][1,2,4]triazin-4-amine | 339.30 | 1.982[a] |
| 4 | H | H | H | 2-(4-amino-1-piperidinyl)-N-1H-pyrazol-5-ylpyrrolo[2,1-f][1,2,4]triazin-4-amine | 299.26 | 1.492[a] |
| 5 | cyclopropyl | Me | Me | N-(3-cyclopropyl-1H-pyrazol-5-yl)-2-(4-(dimethylamino)-1-piperidinyl)pyrrolo[2,1-f][1,2,4]triazin-4-amine | 367.33 | 1.973[b] |
| 6 | cyclopropyl | Me | H | N-(3-cyclopropyl-1H-pyrazol-5-yl)-2-(4-(methylamino)-1-piperidinyl)pyrrolo[2,1-f][1,2,4]triazin-4-amine | 353.33 | 2.020[b] |
| 7 | CO₂H | H | H | 5-((2-(4-amino-1-piperidinyl)pyrrolo[2,1-f][1,2,4]triazin-4-yl)amino)-1H-pyrazole-3-carboxylic acid | 343.24 | 1.833[a] |
| 8 | cyclopropyl | CH₂Ph | H | 2-(4-(benzylamino)-1-piperidinyl)-N-(3-cyclopropyl-1H-pyrazol-5-yl)pyrrolo[2,1-f][1,2,4]triazin-4-amine | 429.19 | 2.380[b] |
| 9 | C(O)NHPh | H | H | 5-((2-(4-amino-1-piperidinyl)pyrrolo[2,1-f][1,2,4]triazin-4-yl)amino)-N-phenyl-1H-pyrazole-3-carboxamide | 418.11 | 2.423[b] |
| 10 | Ph (α,α-dimethyl) | H | H | 2-(4-amino-1-piperidinyl)-N-(3-phenyl-1H-pyrazol-5-yl)pyrrolo[2,1-f][1,2,4]triazin-4-amine | 375.20 | 2.497[a] |
| 11 | CH₂Ph | H | H | 2-(4-amino-1-piperidinyl)-N-(3-benzyl-1H-pyrazol-5-yl)pyrrolo[2,1-f][1,2,4]triazin-4-amine | 389.25 | 2.352[b] |

TABLE 2-continued

| Ex. No. | R¹ | R² | R³ | Compound name | [M + H] | HPLC Ret Time (min) |
|---|---|---|---|---|---|---|
| 12 | (1S,2S)-2-phenylcyclopropyl | H | H | 2-(4-amino-1-piperidinyl)-N-(3-((1S,2S)-2-phenylcyclopropyl)-1H-pyrazol-5-yl)pyrrolo[2,1-f][1,2,4]triazin-4-amine | 415 | 2.680[b] |
| 13 | isopropyl | H | H | 2-(4-amino-1-piperidinyl)-N-(3-isopropyl-1H-pyrazol-5-yl)pyrrolo[2,1-f][1,2,4]triazin-4-amine | 341.31 | 2.077[b] |
| 14 | cyclopropylmethoxy | H | H | 2-(4-amino-1-piperidinyl)-N-(3-(cyclopropylmethoxy)-1H-pyrazol-5-yl)pyrrolo[2,1-f][1,2,4]triazin-4-amine | 369.25 | 2.298[a] |
| 15 | cyclopropylmethyl | H | H | 2-(4-amino-1-piperidinyl)-N-(3-(cyclopropylmethyl)-1H-pyrazol-5-yl)pyrrolo[2,1-f][1,2,4]triazin-4-amine | 353.26 | 2.158[b] |
| 16 | isobutyl | H | H | 2-(4-amino-1-piperidinyl)-N-(3-isobutyl-1H-pyrazol-5-yl)pyrrolo[2,1-f][1,2,4]triazin-4-amine | 355.28 | 2.265[b] |
| 17 | cyclobutylmethyl | H | H | 2-(4-amino-1-piperidinyl)-N-(3-cyclobutyl-1H-pyrazol-5-yl)pyrrolo[2,1-f][1,2,4]triazin-4-amine | 353.28 | 2.175[b] |

TABLE 2-continued

| Ex. No. | R¹ | R² | R³ | Compound name | [M + H] | HPLC Ret Time (min) |
|---|---|---|---|---|---|---|
| 18 | (1S,2S)-2-methylcyclopropyl | H | H | 2-(4-amino-1-piperidinyl)-N-(3-((1S,2S)-2-methylcyclopropyl)-1H-pyrazol-5-yl)pyrrolo[2,1-f][1,2,4]triazin-4-amine | 353.27 | 2.177[b] |
| 19 | sec-butyl | H | H | 2-(4-amino-1-piperidinyl)-N-(3-sec-butyl-1H-pyrazol-5-yl)pyrrolo[2,1-f][1,2,4]triazin-4-amine | 355.34 | 2.265[b] |
| 20 | ethyl | H | H | 2-(4-amino-1-piperidinyl)-N-(3-ethyl-1H-pyrazol-5-yl)pyrrolo[2,1-f][1,2,4]triazin-4-amine | 327.32 | 1.850[b] |
| 21 | tert-butyl | H | H | 2-(4-amino-1-piperidinyl)-N-(3-tert-butyl-1H-pyrazol-5-yl)pyrrolo[2,1-f][1,2,4]triazin-4-amine | 355.30 | 2.225[b] |
| 22 | 1-methylcyclopropyl | H | H | 2-(4-amino-1-piperidinyl)-N-(3-(1-methylcyclopropyl)-1H-pyrazol-5-yl)pyrrolo[2,1-f][1,2,4]triazin-4-amine | 353.27 | 2.150[b] |

HPLC Conditions:

[a] YMC S5 Combiscreen ODS 4.6 × 50 mm, 10-90% aqueous methanol containing 0.2% $H_3PO_4$, 4 min gradient, monitored at 220 or 254 nm)

[b] Chromolith SpeedROD 4.6 × 50 mm, 10-90% aqueous methanol containing 0.1% TFA, 4 min gradient, monitored at 220 or 254 nm)

Example 23

N-(1-(4-((3-Cyclopropyl-1H-pyrazol-5-yl)amino)pyrrolo[2,1-f][1,2,4]triazin-2-yl)-4-piperidinyl)-3-methylbutanamide

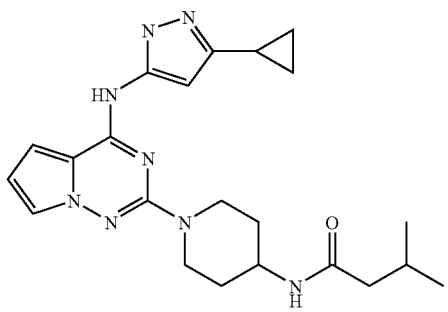

A solution of the compound from Example 3 (24 mg, 0.07 mmol) in DMF (0.35 mL) was treated with a solution of EDC (17 mg, 0.088 mmol), HOBt (12 mg, 0.088 mmol) and DIEA (0.061 mL, 0.35 mmol) in DMF (0.35 mL). 3-Methylbutanoic acid (6.4 mg, 0.063 mmol) was added and the reaction was agitated overnight at ambient temperature. The desired product was purified directly by reversed-phase HPLC with LC/MS detection (Waters SunFire Prep C18 OBD, 19×100 mm×5 um, 10-90% aqueous acetonitrile containing 0.1% TFA) to afford the title compound (9.5 mg). HPLC $R_t$=3.08 min (Waters SunFire C18 4.6×50 mm, 10-90% aqueous methanol containing 0.1% TFA, 4 min gradient, monitored at 220 nm). m/z=443.45 (M+H).

Examples 24 to 59

The following compounds in Table 3 have been synthesized utilizing the procedures described in Example 23.

TABLE 3

| Ex. No. | $R^2$ | Compound name | [M + H] | HPLC Ret Time (min)$^a$ |
|---|---|---|---|---|
| 24 | (CH$_2$N(CH$_3$)$_2$ ketone) | N-(1-(4-((3-cyclopropyl-1H-pyrazol-5-yl)amino)pyrrolo[2,1-f][1,2,4]triazin-2-yl)-4-piperidinyl)-2-(dimethylamino)acetamide | 424.5 | 2.24 |
| 25 | (4-chlorobenzoyl) | 4-chloro-N-(1-(4-((3-cyclopropyl-1H-pyrazol-5-yl)amino)pyrrolo[2,1-f][1,2,4]triazin-2-yl)-4-piperidinyl)benzamide | 477.35 | 3.38 |
| 26 | (2,2-diphenylacetyl) | N-(1-(4-((3-cyclopropyl-1H-pyrazol-5-yl)amino)pyrrolo[2,1-f][1,2,4]triazin-2-yl)-4-piperidinyl)-2,2-diphenylacetamide | 533.33 | 3.51 |

TABLE 3-continued

| Ex. No. | R² | Compound name | [M + H] | HPLC Ret Time (min)ᵃ |
|---|---|---|---|---|
| 27 | 4-methoxybenzoyl | N-(1-(4-((3-cyclopropyl-1H-pyrazol-5-yl)amino)pyrrolo[2,1-f][1,2,4]triazin-2-yl)-4-piperidinyl)-4-methoxybenzamide | 473.42 | 3.12 |
| 28 | 1-methyl-1H-pyrrol-2-ylcarbonyl | N-(1-(4-((3-cyclopropyl-1H-pyrazol-5-yl)amino)pyrrolo[2,1-f][1,2,4]triazin-2-yl)-4-piperidinyl)-1-methyl-1H-pyrrole-2-carboxamide | 446.45 | 3.04 |
| 29 | furan-2-ylcarbonyl | N-(1-(4-((3-cyclopropyl-1H-pyrazol-5-yl)amino)pyrrolo[2,1-f][1,2,4]triazin-2-yl)-4-piperidinyl)-2-furamide | 433.47 | 2.89 |
| 30 | benzofuran-2-ylcarbonyl | N-(1-(4-((3-cyclopropyl-1H-pyrazol-5-yl)amino)pyrrolo[2,1-f][1,2,4]triazin-2-yl)-4-piperidinyl)-1-benzofuran-2-carboxamide | 483.41 | 3.37 |
| 31 | pyrazin-2-ylcarbonyl | N-(1-(4-((3-cyclopropyl-1H-pyrazol-5-yl)amino)pyrrolo[2,1-f][1,2,4]triazin-2-yl)-4-piperidinyl)-2-pyrazinecarboxamide | 445.44 | 2.89 |
| 32 | pyridin-4-ylcarbonyl | N-(1-(4-((3-cyclopropyl-1H-pyrazol-5-yl)amino)pyrrolo[2,1-f][1,2,4]triazin-2-yl)-4-piperidinyl) isonicotinamide | 444.45 | 2.49 |
| 33 | 1,3-benzothiazol-2-ylcarbonyl | N-(1-(4-((3-cyclopropyl-1H-pyrazol-5-yl)amino)pyrrolo[2,1-f][1,2,4]triazin-2-yl)-4-piperidinyl)-1,3-benzothiazole-2-carboxamide | 500.32 | 3.52 |

TABLE 3-continued

| Ex. No. | R[2] | Compound name | [M + H] | HPLC Ret Time (min)[a] |
|---|---|---|---|---|
| 34 | (1-methyl-1H-indol-2-yl)carbonyl | N-(1-(4-((3-cyclopropyl-1H-pyrazol-5-yl)amino)pyrrolo[2,1-f][1,2,4]triazin-2-yl)-4-piperidinyl)-1-methyl-1H-indole-3-carboxamide | 496.41 | 3.26 |
| 35 | (5-phenyl-2-furyl)carbonyl | N-(1-(4-((3-cyclopropyl-1H-pyrazol-5-yl)amino)pyrrolo[2,1-f][1,2,4]triazin-2-yl)-4-piperidinyl)-5-phenyl-2-furamide | 509.35 | 3.51 |
| 36 | (2-thienyl)carbonyl | N-(1-(4-((3-cyclopropyl-1H-pyrazol-5-yl)amino)pyrrolo[2,1-f][1,2,4]triazin-2-yl)-4-piperidinyl)-2-thiophenecarboxamide | 496.41 | 3.26 |
| 37 | (2-methylphenyl)carbonyl | N-(1-(4-((3-cyclopropyl-1H-pyrazol-5-yl)amino)pyrrolo[2,1-f][1,2,4]triazin-2-yl)-4-piperidinyl)-2-methylbenzamide | 457.45 | 3.13 |
| 38 | isobutyryl | N-(1-(4-((3-cyclopropyl-1H-pyrazol-5-yl)amino)pyrrolo[2,1-f][1,2,4]triazin-2-yl)-4-piperidinyl)-2-methylpropanamide | 409.41 | 2.86 |
| 39 | cyanoacetyl | 2-cyano-N-(1-(4-((3-cyclopropyl-1H-pyrazol-5-yl)amino)pyrrolo[2,1-f][1,2,4]triazin-2-yl)-4-piperidinyl)acetamide | 406.5 | 2.6 |
| 40 | 3,3-dimethylbutanoyl | N-(1-(4-((3-cyclopropyl-1H-pyrazol-5-yl)amino)pyrrolo[2,1-f][1,2,4]triazin-2-yl)-4-piperidinyl)-3,3-dimethylbutanamide | 437.52 | 3.24 |

TABLE 3-continued

| Ex. No. | R² | Compound name | [M + H] | HPLC Ret Time (min)ᵃ |
|---|---|---|---|---|
| 41 | | N-(1-(4-((3-cyclopropyl-1H-pyrazol-5-yl)amino)pyrrolo[2,1-f][1,2,4]triazin-2-yl)-4-piperidinyl)-3,3-diphenylpropanamide | 547.32 | 3.55 |
| 42 | | N-(1-(4-((3-cyclopropyl-1H-pyrazol-5-yl)amino)pyrrolo[2,1-f][1,2,4]triazin-2-yl)-4-piperidinyl)propanamide | 395.51 | 2.72 |
| 43 | | N-(1-(4-((3-cyclopropyl-1H-pyrazol-5-yl)amino)pyrrolo[2,1-f][1,2,4]triazin-2-yl)-4-piperidinyl)-3-phenylpropanamide | 471.42 | 3.26 |
| 44 | | N-(1-(4-((3-cyclopropyl-1H-pyrazol-5-yl)amino)pyrrolo[2,1-f][1,2,4]triazin-2-yl)-4-piperidinyl)-4-methylpentanamide | 437.51 | 3.27 |
| 45 | | N-(1-(4-((3-cyclopropyl-1H-pyrazol-5-yl)amino)pyrrolo[2,1-f][1,2,4]triazin-2-yl)-4-piperidinyl)-2,2-dimethylpropanamide | 423.52 | 3.04 |
| 46 | | N-(1-(4-((3-cyclopropyl-1H-pyrazol-5-yl)amino)pyrrolo[2,1-f][1,2,4]triazin-2-yl)-4-piperidinyl)-2-phenylacetamide | 457.45 | 3.12 |
| 47 | | 2-(4-chlorophenyl)-N-(1-(4-((3-cyclopropyl-1H-pyrazol-5-yl)amino)pyrrolo[2,1-f][1,2,4]triazin-2-yl)-4-piperidinyl)acetamide | 491.35 | 3.39 |
| 48 | | N-(1-(4-((3-cyclopropyl-1H-pyrazol-5-yl)amino)pyrrolo[2,1-f][1,2,4]triazin-2-yl)-4-piperidinyl)pentanamide | 423.5 | 3.10 |

TABLE 3-continued

| Ex. No. | R² | Compound name | [M + H] | HPLC Ret Time (min)ᵃ |
|---|---|---|---|---|
| 49 | | N-(1-(4-((3-cyclopropyl-1H-pyrazol-5-yl)amino)pyrrolo[2,1-f][1,2,4]triazin-2-yl)-4-piperidinyl)-2-(2-thienyl)acetamide | 463.39 | 3.06 |
| 50 | | N-(1-(4-((3-cyclopropyl-1H-pyrazol-5-yl)amino)pyrrolo[2,1-f][1,2,4]triazin-2-yl)-4-piperidinyl)-3-(1-piperidinyl)propanamide | 478.48 | 2.39 |
| 51 | | 3-(4-chlorophenyl)-N-(1-(4-((3-cyclopropyl-1H-pyrazol-5-yl)amino)pyrrolo[2,1-f][1,2,4]triazin-2-yl)-4-piperidinyl)propanamide | 505.35 | 3.45 |
| 52 | | N-(1-(4-((3-cyclopropyl-1H-pyrazol-5-yl)amino)pyrrolo[2,1-f][1,2,4]triazin-2-yl)-4-piperidinyl)-3-methoxypropanamide | 425.84 | 2.68 |
| 53 | | N-(1-(4-((3-cyclopropyl-1H-pyrazol-5-yl)amino)pyrrolo[2,1-f][1,2,4]triazin-2-yl)-4-piperidinyl)-3-(2-oxo 1-pyrrolidinyl)propanamide | 478.42 | 2.65 |
| 54 | | Methyl 4-((1-(4-((3-cyclopropyl-1H-pyrazol-5-yl)amino)pyrrolo[2,1-f][1,2,4]triazin-2-yl)-4-piperidinyl)amino)-4-oxobutanoate | 453.45 | 2.73 |
| 55 | | N-(1-(4-((3-cyclopropyl-1H-pyrazol-5-yl)amino)pyrrolo[2,1-f][1,2,4]triazin-2-yl)-4-piperidinyl)-2-(1H-tetrazol-5-yl)acetamide | 449.44 | 2.54 |

TABLE 3-continued

| Ex. No. | R² | Compound name | [M + H] | HPLC Ret Time (min)[a] |
|---|---|---|---|---|
| 56 | ![structure] | 4-(aminosulfonyl)-N-(1-(4-((3-cyclopropyl-1H-pyrazol-5-yl)amino)pyrrolo[2,1-f][1,2,4]triazin-2-yl)-4-piperidinyl)butanamide | 488.36 | 2.49 |
| 57 | ![structure] | N-(1-(4-((3-cyclopropyl-1H-pyrazol-5-yl)amino)pyrrolo[2,1-f][1,2,4]triazin-2-yl)-4-piperidinyl)tetrahydro-2-furancarboxamide | 437.48 | 2.82 |
| 58 | ![structure] | N-(1-(4-((3-cyclopropyl-1H-pyrazol-5-yl)amino)pyrrolo[2,1-f][1,2,4]triazin-2-yl)-4-piperidinyl)succinamide | 438.47 | 2.46 |
| 59 | ![structure] | N-(1-(4-((3-cyclopropyl-1H-pyrazol-5-yl)amino)pyrrolo[2,1-f][1,2,4]triazin-2-yl)-4-piperidinyl)-4-pentynamide | 419.48 | 2.80 |

[a]Waters SunFire C18 4.6 × 50 mm, 10-90% aqueous methanol containing 0.1% TFA, 4 min gradient, monitored at 220 nm).

Example 60

1-(4-(3-Cyclopropyl-1H-pyrazol-5-ylamino)pyrrolo[1,2-f][1,2,4]triazin-2-yl)piperidin-4-yl)benzamide

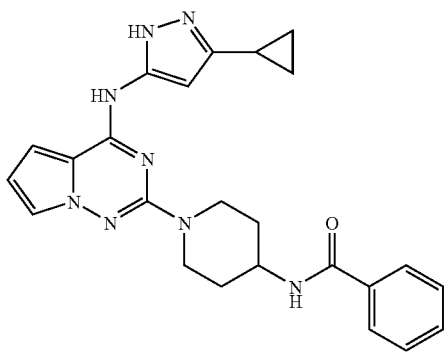

A mixture of 2-(4-aminopiperidin-1-yl)-N-(3-cyclopropyl-1H-pyrazol-5-yl)pyrrolo[1,2-f][1,2,4]triazin-4-amine (20 mg, 0.06 mmol) in DMF (1 mL) was treated with benzoic acid (10 mg, 0.08 mmol), N,N,N',N'-tetramethyl-O-(benzotriazol-1-yl)uronium tetrafluoroborate (20 mg, 0.06 mmol), and DIEA (0.1 mL, 0.59 mmol). The reaction was stirred at room temperature overnight. The mixture was diluted with methanol and purified with preparative reversed-phase HPLC (YMC ODS-A 20×100 mm, 10-90% aqueous methanol containing 0.1% TFA, 10 min gradient, monitored at 220 nm) to give N-(1-(4-(3-cyclopropyl-1H-pyrazol-5-ylamino)pyrrolo[1,2-f][1,2,4]triazin-2-yl)piperidin-4-yl)benzamide (11 mg, 42%). ¹HNMR (DMSO) δ 10.22 (s, 1H), 8.18 (d, 1H, J=7.6 Hz), 7.77 (d, 2H, J=7.6 Hz), 7.43 (m, 5H), 7.00 (s, 1H), 6.36 (s, 1H), 6.28 (s, 1H), 4.33 (d, 2H, J=13.2 Hz), 4.02 (s, 1H), 3.23 (t, 2H, J=7.6 Hz), 1.84 (m, 3H), 1.54 (m, 2H), 0.88 (m, 2H), 0.63 (m, 2H). HPLC (b). $R_t$=2.76 min. (Chromolith

Example 61

N-(1-(4-(3-Cyclopropyl-1H-pyrazol-5-ylamino)pyrrolo[1,2-f][1,2,4]triazin-2-yl)piperidin-4-yl)acetamide

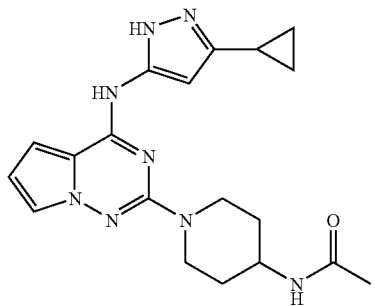

A mixture of 2-(4-aminopiperidin-1-yl)-N-(3-cyclopropyl-1H-pyrazol-5-yl)pyrrolo[1,2-f][1,2,4]triazin-4-amine (24 mg, 0.07 mmol) in toluene (10 mL) was treated with acetic anhydride (0.032 mL, 0.28 mmol). The reaction was refluxed for 6 h, concentrated to dryness and redissolved in MeOH (10 mL). Potassium carbonate (20 mg) was added and the mixture was stirred at room temperature for 1 h. The solid was removed by filtration and the mixture was purified with preparative reversed-phase HPLC (YMC ODS-A 20×100 mm, 10-90% aqueous methanol containing 0.1% TFA, 10 min gradient, monitored at 220 nm) to give N-(1-(4-(3-cyclopropyl-1H-pyrazol-5-ylamino)pyrrolo[1,2-f][1,2,4]triazin-2-yl)piperidin-4-yl)acetamide (14 mg, 53%). $^1$HNMR (DMSO) δ 10.28 (s, 1H), 7.79 (d, 1H, J=7.6 Hz), 7.41 (s, 1H), 7.05 (s, 1H), 6.42 (m, 1H), 6.33 (s, 1H), 4.26 (d, 2H, J=13.2 Hz), 3.81 (s, 1H), 2.98 (t, 2H, J=11.6 Hz), 1.93 (m, 1H), 1.79 (s, 3H), 1.75 (m, 3H), 1.36 (m, 2H), 0.96 (m, 2H), 0.67 (m, 2H). HPLC (b). $t_R$=2.39 min. (Chromolith SpeedROD 4.6×50 mm, 10-90% aqueous methanol containing 0.1% TFA, 4 min gradient, monitored at 220 or 254 nm). m/z=381.29 (M+H).

Example 62

1-(1-(4-(3-Cyclopropyl-1H-pyrazol-5-ylamino)pyrrolo[1,2-f][1,2,4]triazin-2-yl)piperidin-4-yl)-3-ethylurea

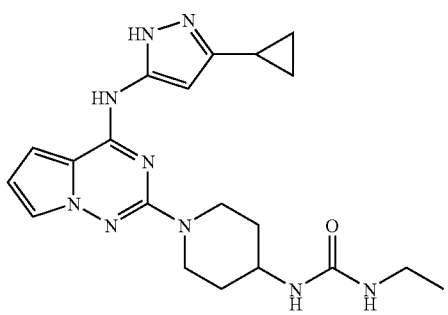

A solution of 2-(4-aminopiperidin-1-yl)-N-(3-cyclopropyl-1H-pyrazol-5-yl)pyrrolo[1,2-f][1,2,4]triazin-4-amine (14 mg, 0.04 mmol) in acetonitrile (20 mL) was treated with ethyl isocyanate (0.5 mL, 0.08 M in acetonitrile, 0.04 mmol). The reaction was stirred at room temperature for 1 hour, and then concentrated. The crude product was purified with preparative reversed-phase HPLC (YMC ODS-A 20×100 mm, 10-90% aqueous methanol containing 0.1% TFA, 10 min gradient, monitored at 220 nm) to give 1-(1-(4-(3-cyclopropyl-1H-pyrazol-5-ylamino)pyrrolo[1,2-f][1,2,4]triazin-2-yl)piperidin-4-yl)-3-ethylurea (3 mg, 18%). $^1$HNMR (DMSO) δ 10.18 (s, 1H), 7.30 (s, 1H), 6.98 (s, 1H), 6.34 (m, 1H), 6.26 (s, 1H), 4.13 (d, 2H, J=13.2 Hz), 3.55 (s, 1H), 2.93 (m, 4H), 1.84 (m, 1H), 1.72 (m, 2H), 1.23 (m, 2H), 0.90 (m, 6H), 0.59 (m, 2H). HPLC (a). $t_R$=2.63 min. (YMC S5 Combiscreen ODS 4.6×50 mm, 10-90% aqueous methanol containing 0.2% $H_3PO_4$, 4 min gradient, monitored at 220 or 254 nm). m/z=410.22 (M+H).

Example 63

N-(1-(4-(3-Cyclopropyl-1H-pyrazol-5-ylamino)pyrrolo[1,2-f][1,2,4]triazin-2-yl)piperidin-4-yl)methanesulfonamide

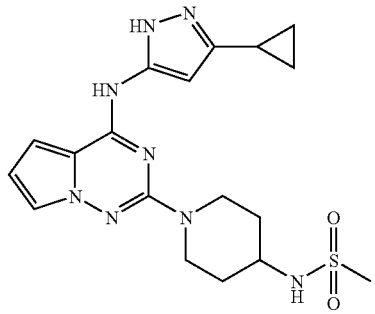

A suspension of 2-(4-aminopiperidin-1-yl)-N-(3-cyclopropyl-1H-pyrazol-5-yl)pyrrolo[1,2-f][1,2,4]triazin-4-amine (50 mg, 0.15 mmol) in THF (20 mL) was treated with methanesulfonyl chloride (1 mL, 0.13 M in THF, 0.13 mmol). The reaction mixture was stirred at room temperature overnight. The solvent was removed under reduced pressure and the crude product was purified by preparative reversed-phase HPLC (YMC ODS-A 20×100 mm, 10-90% aqueous methanol containing 0.1% TFA, 10 min gradient, monitored at 220 nm) to give N-(1-(4-(3-cyclopropyl-1H-pyrazol-5-ylamino)pyrrolo[1,2-f][1,2,4]triazin-2-yl)piperidin-4-yl)methanesulfonamide (10 mg, 19%). $^1$HNMR (DMSO) δ 10.20 (s, 1H), 7.34 (s, 1H), 7.02 (m, 2H), 6.35 (s, 1H), 6.26 (s, 1H), 4.19 (d, 2H, J=12.8 Hz), 3.34 (s, 1H), 2.90 (m, 3H), 2.88 (s, 3H), 1.83 (m, 3H), 1.37 (m, 2H), 0.90 (m, 2H), 0.60 (m, 2H). HPLC (a). $R_f$=2.58 min. (YMC S5 Combiscreen ODS 4.6×50 mm, 10-90% aqueous methanol containing 0.2% $H_3PO_4$, 4 min gradient, monitored at 220 or 254 nm). m/z=417.19 (M+H).

Example 64

N-(1-(4-(3-Cyclopropyl-1H-pyrazol-5-ylamino)pyrrolo[1,2-f][1,2,4]triazin-2-yl)piperidin-4-yl)-2,2,2-trifluoroacetamide

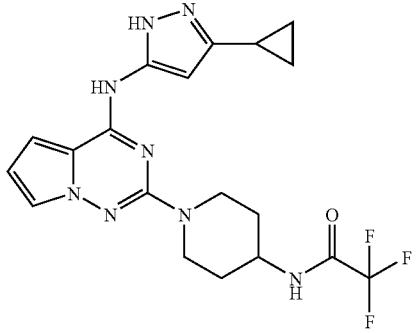

A solution of 2-(4-aminopiperidin-1-yl)-N-(3-cyclopropyl-1H-pyrazol-5-ylamino)pyrrolo[1,2-f][1,2,4]triazin-4-amine (35 mg, 0.08 mmol) in toluene (10 mL) was treated with acetic anhydride (60 uL, 0.63 mmol). The reaction was refluxed for 6 hours and then concentrated to dryness. The crude reaction mixture was dissolved in MeOH (5 mL) and potassium carbonate (100 mg) was added. After stirring at room temperature for 2 hours, the mixture was filtered and the filtrate was concentrated and purified with preparative reversed-phase HPLC (YMC ODS-A 20×100 mm, 10-90% aqueous methanol containing 0.1% TFA, 10 min gradient, monitored at 220 nm) to give N-(1-(4-(3-cyclopropyl-1H-pyrazol-5-ylamino)pyrrolo[1,2-f][1,2,4]triazin-2-yl)piperidin-4-yl)-2,2,2-trifluoroacetamide (4 mg, 12%). $^1$HNMR (DMSO) δ 10.20 (s, 1H), 9.21 (d, 1H, J=7.6 Hz), 7.35 (s, 1H), 6.99 (s, 1H), 6.36 (s, 1H), 6.26 (s, 1H), 4.30 (d, 2H, J=12.8 Hz), 3.87 (s, 1H), 3.10 (s, 1H), 2.86 (t, 2H, J=12.8 Hz), 1.85 (m, 1H), 1.72 (m, 2H), 1.50 (m, 2H), 0.88 (m, 2H), 0.61 (m, 2H). HPLC (a). $R_t$=2.95 min. (YMC S5 Combiscreen ODS 4.6×50 mm, 10-90% aqueous methanol containing 0.2% $H_3PO_4$, 4 min gradient, monitored at 220 or 254 nm). m/z=435.17 (M+H).

Example 65

N-(1-(4-(3-Isobutyl-1H-pyrazol-5-ylamino)pyrrolo[1,2-f][1,2,4]triazin-2-yl)piperidin-4-yl)acetamide

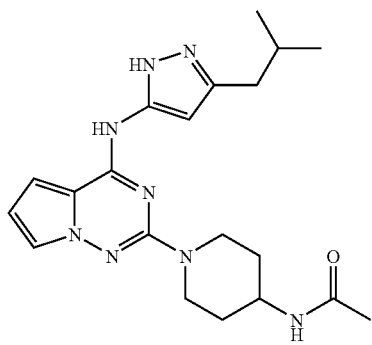

A solution of 2-(4-aminopiperidin-1-yl)-N-(3-isobutyl-1H-pyrazol-5-yl)pyrrolo[1,2-f][1,2,4]triazin-4-amine (8 mg, 0.02 mmol) in toluene (5 mL) was filtered through a pad of sodium bicarbonate. The filtrate was treated with acetic anhydride (0.005 mL, 0.05 mmol) and refluxed for 3 hours. The solvent was removed under reduced pressure and the residue was dissolved in MeOH (5 mL). Aqueous NaOH (0.5 mL, 1M) was added, and the mixture was stirred at room temperature for 30 min. The mixture was concentrated and purified with preparative reversed-phase HPLC (YMC ODS-A 20×100 mm, 10-90% aqueous methanol containing 0.1% TFA, 10 min gradient, monitored at 220 nm) to give N-(1-(4-(3-isobutyl-1H-pyrazol-5-ylamino)pyrrolo[1,2-f][1,2,4]triazin-2-yl)piperidin-4-yl)acetamide (1 mg, 15%). $^1$HNMR (DMSO) δ 10.25 (s, 1H), 7.78 (d, 1H, J=8.0 Hz), 7.41 (s, 1H), 7.06 (s, 1H), 6.45 (s, 1H), 6.42 (m, 1H), 4.28 (d, 2H, J=13.2 Hz), 3.79 (s, 1H), 2.96 (t, 2H, J=11.6 Hz), 1.91 (m, 1H), 1.79 (s, 3H), 1.74 (m, 2H), 1.34 (m, 2H), 0.92 (d, 6H, J=6.4 Hz). HPLC (b). $t_R$=2.62 min. (Chromolith SpeedROD 4.6×50 mm, 10-90% aqueous methanol containing 0.1% TFA, 4 min gradient, monitored at 220 or 254 nm). m/z=397.30 (M+H).

Example 66

N-(1-(4-(3-(Cyclopropylmethoxy)-1H-pyrazol-5-ylamino)pyrrolo[1,2-f][1,2,4]triazin-2-yl)piperidin-4-yl)acetamide

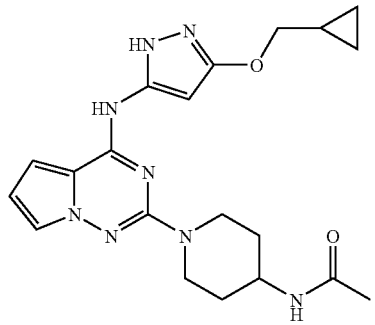

A mixture of 2-(4-aminopiperidin-1-yl)-N-(3-(cyclopropylmethoxy)-1H-pyrazol-5-ylamino)pyrrolo[1,2-f][1,2,4]triazin-4-amine (5 mg, 0.01 mmol) in toluene (5 mL) was treated with acetic anhydride (0.005 mL, 0.05 mmol) and refluxed for 3 hours. The reaction was concentrated and then redissolved in MeOH (1 mL). Aqueous NaOH (0.5 mL, 1M) was added and the mixture was stirred at room temperature for 30 min. The resulting mixture was purified directly by preparative reversed-phase HPLC (YMC ODS-A 20×100 mm, 10-90% aqueous methanol containing 0.1% TFA, 10 min gradient, monitored at 220 nm) to give N-(1-(4-(3-(cyclopropylmethoxy)-1H-pyrazol-5-ylamino)pyrrolo[1,2-f][1,2,4]triazin-2-yl)piperidin-4-yl)acetamide (1 mg, 19%). $^1$HNMR (DMSO) δ 10.28 (s, 1H), 7.80 (d, 1H, J=7.6 Hz), 7.45 (s, 1H), 6.95 (s, 1H), 6.46 (m, 1H), 5.88 (s, 1H), 4.26 (d, 2H, J=13.2 Hz), 3.90 (d, 2H, J=7.2 Hz), 3.79 (s, 1H), 2.96 (t, 2H, J=11.2 Hz), 1.79 (s, 3H), 1.76 (m, 2H), 1.32 (m, 2H), 1.25 (m, 2H), 0.57 (m, 2H), 0.33 (m, 2H). HPLC (b). $t_R$=2.62 min. (Chromolith SpeedROD 4.6×50 mm, 10-90% aqueous methanol containing 0.1% TFA, 4 min gradient, monitored at 220 or 254 nm). m/z=411.22 (M+H).

Example 67

Rac-N-(1-(4-((3-((1R,2R)-2-methylcyclopropyl)-1H-pyrazol-5-yl)amino)pyrrolo[2,1-f][1,2,4]triazin-2-yl)-4-piperidinyl)acetamide

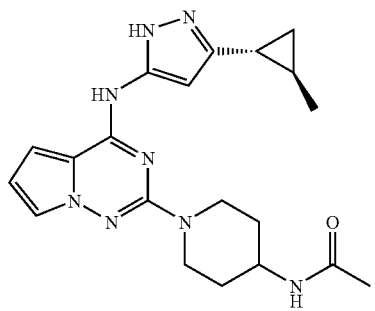

A mixture of 2-(4-aminopiperidin-1-yl)-N-(3-(trans-2-methylcyclopropyl)-1H-pyrazol-5-yl)pyrrolo[1,2-f][1,2,4] triazin-4-amine (7 mg, 0.02 mmol) in toluene (5 mL) was treated with acetic anhydride (5 uL, 0.05 mmol) and refluxed for 3 hours. The solvent was removed under reduced pressure and the residue was redissolved in MeOH (2 mL). Aqueous NaOH (5 drops, 1M) was added and the mixture was stirred at room temperature for 30 min. The mixture was purified directly by preparative reversed-phase HPLC (YMC ODS-A 20×100 mm, 10-90% aqueous methanol containing 0.1% TFA, 10 min gradient, monitored at 220 nm) to give N-(1-(4-(3-(trans-2-methylcyclopropyl)-1H-pyrazol-5-ylamino)pyrrolo[1,2-f][1,2,4]triazin-2-yl)piperidin-4-yl)acetamide (4 mg, 53%). $^1$HNMR (DMSO) δ 10.25 (s, 1H), 7.79 (d, 1H, J=7.6 Hz), 7.40 (s, 1H), 7.06 (s, 1H), 6.42 (m, 1H), 6.30 (s, 1H), 4.26 (d, 2H, J=13.2 Hz), 3.80 (s, 1H), 2.98 (t, 2H, J=11.6 Hz), 1.79 (s, 3H), 1.76 (m, 2H), 1.63 (m, 1H), 1.33 (m, 2H), 1.14 (m, 3H), 1.10 (m, 1H), 0.85 (m, 1H), 0.77 (m, 1H). HPLC $t_R$=2.53 min. (Chromolith SpeedROD 4.6×50 mm, 10-90% aqueous methanol containing 0.1% TFA, 4 min gradient, monitored at 220 or 254 nm). m/z=395.22 (M+H).

Example 68

4-Amino-N-(1-(4-((3-cyclopropyl-1H-pyrazol-5-yl) amino)pyrrolo[2,1-f][1,2,4]triazin-2-yl)-4-piperidinyl)butanamide

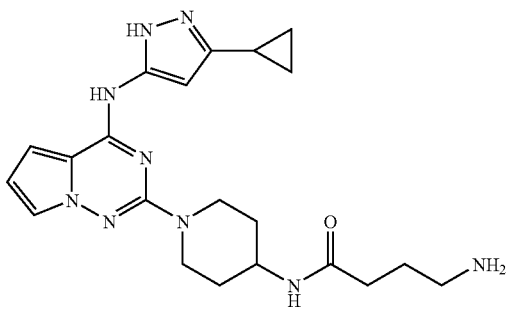

A mixture of 2-(4-aminopiperidin-1-yl)-N-(3-cyclopropyl-1H-pyrazol-5-yl)pyrrolo[1,2-f][1,2,4]triazin-4-amine (Example 3) (35 mg, 0.08 mmol) in DMF (1 mL), was treated with 4-(tert-butoxycarbonylamino)butanoic acid (21 mg, 0.10 mmol), N,N,N',N'-tetramethyl-O-(benzotriazol-1-yl) uronium tetrafluoroborate (40 mg, 0.12 mmol), and DIEA (0.1 mL, 0.59 mmol). The reaction was stirred at room temperature overnight. The reaction was filtered and the product was purified with preparative reversed-phase HPLC (YMC ODS-A 20×100 mm, 10-90% aqueous methanol containing 0.1% TFA, 10 min gradient, monitored at 220 nm) to give tert-butyl 4-(1-(4-(3-cyclopropyl-1H-pyrazol-5-ylamino) pyrrolo[1,2-f][1,2,4]triazin-2-yl)piperidin-4-ylamino)-4-oxobutylcarbamate (10 mg, 25%). The protected amine was dissolve in DCM (10 mL), and TFA (0.1 mL, 1.3 mmol) was added The mixture was stirred at room temperature overnight, concentrated and purified with preparative reversed-phase HPLC (YMC ODS-A 20×100 mm, 10-90% aqueous methanol containing 0.1% TFA, 10 min gradient, monitored at 220 nm) to give 4-amino-N-(1-(4-(3-cyclopropyl-1H-pyrazol-5-ylamino)pyrrolo[1,2-f][1,2,4]triazin-2-yl)piperidin-4-yl)butanamide (6 mg, 75%). $^1$HNMR (MeOD) δ 7.53 (q, 1H, J=1.6 Hz), 7.06 (dd, 1H, J=1.2 Hz, 3.2 Hz), 6.63 (q, 1H, J=2.4 Hz), 6.19 (s, 1H), 4.31 (d, 2H, J=16 Hz), 3.96 (m, 1H), 3.14 (t, 2H, J=12 Hz), 2.99 (t, 2H, J=8 Hz), 2.37 (t, 2H, J=8 Hz), 1.96 (m, 6H), 1.58 (m, 2H), 1.07 (m, 2H), 0.79 (m, 2H). HPLC $t_R$=2.14 min. (Chromolith SpeedROD 4.6×50 mm, 10-90% aqueous methanol containing 0.1% TFA, 4 min gradient, monitored at 220 or 254 nm). m/z=424.25 (M+H).

Example 69

1-(4-((3-Cyclopropyl-1H-pyrazol-5-yl)amino)pyrrolo[2,1-f][1,2,4]triazin-2-yl)-4-piperidinecarboxamide

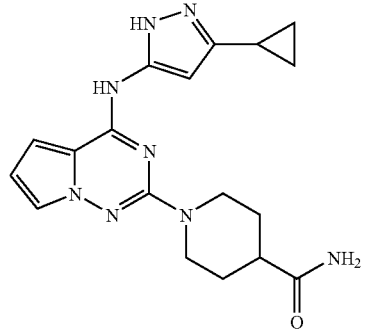

69A. Preparation of 2-chloro-N-(3-cyclopropyl-1H-pyrazol-5-yl)pyrrolo[1,2-f][1,2,4]triazin-4-amine

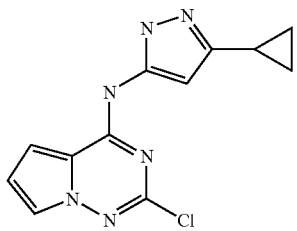

A solution of 2,4-dichloropyrrolo[1,2-f][1,2,4]triazine (1.5 g, 5.3 mmol) in i-PrOH (15 mL) was treated with 3-cyclopropyl-1H-pyrazol-5-amine (657 mg, 5.3 mmol) and DIEA (0.92 mL, 5.3 mmol). The reaction was stirred overnight at ambient temperature and then filtered. The filter cake was washed with cold i-PrOH and dried under vacuum to afford 69A as a solid (1.3 g, 90%). HPLC $t_R$=3.301 min (YMC S5 Combiscreen ODS 4.6×50 mm, 10-90% aqueous methanol containing 0.2% $H_3PO_4$, 4 min gradient, monitored at 254 nm). [M+H]$^+$=275.37.

A solution of 2-chloro-N-(3-cyclopropyl-1H-pyrazol-5-yl)pyrrolo[1,2-f][1,2,4]triazin-4-amine (1A) (100 mg, 0.36 mmol) and piperidine-4-carboxamide (467 mg, 3.6 mmol) in NMP (1 mL) was heated in a microwave safe tube (CEM Corporation, 10 mL) at 100° C. for 40 minutes using 300 W continuous power. The reaction was diluted with EtOAc (10 mL) and washed with 10% aqueous LiCl solution (2×10 mL). The organic layers were combined and dried (Na$_2$SO$_4$), filtered and concentrated. The crude product was purified by preparative reversed-phase HPLC to afford the title compound (23 mg, 15%). HPLC $t_R$=2.398 min (YMC S5 Combiscreen ODS 4.6×50 mm, 10-90% aqueous methanol containing 0.2% $H_3PO_4$, 4 min gradient, monitored at 254 nm). [M+H]$^+$=367.21.

Examples 70 to 97

The following compounds in Table 4 have been synthesized utilizing the procedures described in Example 69.

TABLE 4

| Ex. No. | R$^1$ | R$^2$ | Compound name | [M + H] | HPLC Ret Time (min) |
|---|---|---|---|---|---|
| 70 | Me | 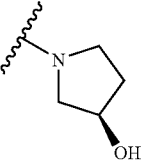 | (3R)-1-(4-((5-methyl-1H-pyrazol-3-yl)amino)pyrrolo[2,1-f][1,2,4]triazin-2-yl)-3-pyrrolidinol | 300.28 | 1.892$^b$ |
| 71 | Me | 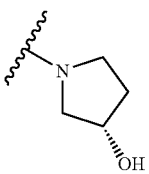 | (3S)-1-(4-((5-methyl-1H-pyrazol-3-yl)amino)pyrrolo[2,1-f][1,2,4]triazin-2-yl)-3-pyrrolidinol | 300.28 | 1.897$^b$ |
| 73 | 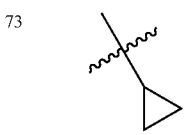 | 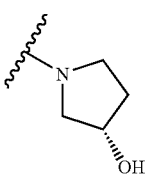 | (3S)-1-(4-((3-cyclopropyl-1H-pyrazol-5-yl)amino)pyrrolo[2,1-f][1,2,4]triazin-2-yl)-3-pyrrolidinol | 326 | 1.087$^c$ |
| 74 | Me | 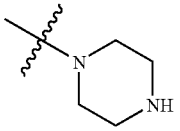 | N-(5-methyl-1H-pyrazol-3-yl)-2-(1-piperazinyl)pyrrolo[2,1-f][1,2,4]triazin-4-amine | 299.31 | 1.492$^a$ |
| 75 | Me | 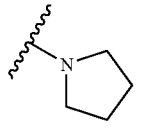 | N-(5-methyl-1H-pyrazol-3-yl)-2-(1-pyrrolidinyl)pyrrolo[2,1-f][1,2,4]triazin-4-amine | 284.29 | 2.403$^b$ |
| 76 | Me | 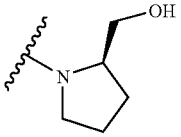 | ((2R)-1-(4-((5-methyl-1H-pyrazol-3-yl)amino)pyrrolo[2,1-f][1,2,4]triazin-2-yl)-2-pyrrolidinyl)methanol | 314 | 1.92$^d$ |
| 77 | Me | 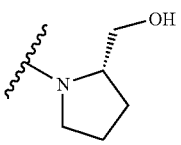 | ((2S)-1-(4-((5-methyl-1H-pyrazol-3-yl)amino)pyrrolo[2,1-f][1,2,4]triazin-2-yl)-2-pyrrolidinyl)methanol | 314 | 1.91$^d$ |

TABLE 4-continued

| Ex. No. | R¹ | R² | Compound name | [M + H] | HPLC Ret Time (min) |
|---|---|---|---|---|---|
| 78 | cyclopropyl | (2R)-pyrrolidinyl-CH2OH | ((2R)-1-(4-((3-cyclopropyl-1H-pyrazol-5-yl)amino)pyrrolo[2,1-f][1,2,4]triazin-2-yl)-2-pyrrolidinyl)methanol | 340 | 1.427$^c$ |
| 79 | cyclopropyl | pyrrolidinyl | N-(3-cyclopropyl-1H-pyrazol-5-yl)-2-(1-pyrrolidinyl)pyrrolo[2,1-f][1,2,4]triazin-4-amine | 310 | 1.495$^c$ |
| 80 | cyclopropyl | (2S)-pyrrolidinyl-C(O)NH2 | (2S)-1-(4-((3-cyclopropyl-1H-pyrazol-5-yl)amino)pyrrolo[2,1-f][1,2,4]triazin-2-yl)-2-pyrrolidinecarboxamide | 353 | 1.338$^c$ |
| 81 | cyclopropyl | morpholinyl | N-(3-cyclopropyl-1H-pyrazol-5-yl)-2-(4-morpholinyl)pyrrolo[2,1-f][1,2,4]triazin-4-amine | 326 | 1.48$^c$ |
| 82 | cyclopropyl | piperidinyl | N-(3-cyclopropyl-1H-pyrazol-5-yl)-2-(1-piperidinyl)pyrrolo[2,1-f][1,2,4]triazin-4-amine | 324 | 1.652$^c$ |
| 83 | cyclopropyl | 4-piperidinecarboxamide | 1-(4-((3-cyclopropyl-1H-pyrazol-5-yl)amino)pyrrolo[2,1-f][1,2,4]triazin-2-yl)-4-piperidinecarboxamide | 367.21 | 2.398 $^a$ |
| 84 | cyclopropyl | (2R)-pyrrolidinyl-C(O)NH2 | (2R)-1-(4-((3-cyclopropyl-1H-pyrazol-5-yl)amino)pyrrolo[2,1-f][1,2,4]triazin-2-yl)-2-pyrrolidinecarboxamide | 353 | 1.307$^c$ |
| 85 | cyclopropyl | (2S)-2-(aminomethyl)-1-pyrrolidinyl | 2-((2S)-2-(aminomethyl)-1-pyrrolidinyl)-N-(3-cyclopropyl-1H-pyrazol-5-yl)pyrrolo[2,1-f][1,2,4]triazin-4-amine | 339 | 1.067$^c$ |

TABLE 4-continued

| Ex. No. | R¹ | R² | Compound name | [M + H] | HPLC Ret Time (min) |
|---|---|---|---|---|---|
| 86 | 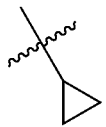 | 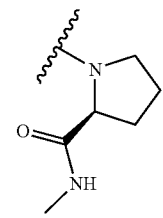 | (2S)-1-(4-((3-cyclopropyl-1H-pyrazol-5-yl)amino) pyrrolo[2,1-f][1,2,4]triazin-2-yl)-N-methyl-2-pyrrolidinecarboxamide | 367 | 1.352[c] |
| 87 | 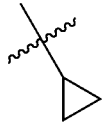 | 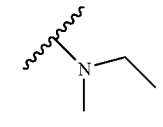 | N~4~-(3-cyclopropyl-1H-pyrazol-5-yl)-N~2~-ethyl-N~2~-methylpyrrolo[2,1-f][1,2,4]triazine-2,4-diamine | 298 | 1.495[c] |
| 88 | 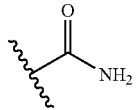 | 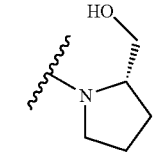 | 5-((2-((2S)-2-(hydroxymethyl)-1-pyrrolidinyl)pyrrolo[2,1-f][1,2,4]triazin-4-yl)amino)-1H-pyrazole-3-carboxamide | 343 | 2.032[d] |
| 89 | 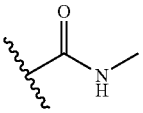 | 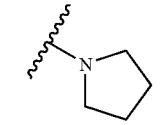 | N-methyl-3-((2-(1-pyrrolidinyl)pyrrolo[2,1-f][1,2,4]triazin-4-yl)amino)-1H-pyrazole-5-carboxamide | 327 | 2,420[d] |
| 90 |  | 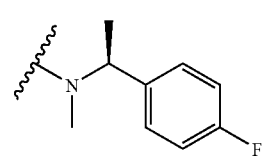 | N-4-(3-cyclopropyl-1H-N-2-((1S)-1-phenylethyl) pyrrolo[2,1-f][1,2,4]triazine-2,4-diamine | 374.41 | 3.415[b] |
| 91 | 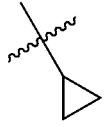 | 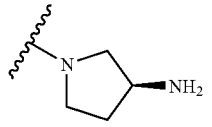 | 2-((3S)-3-amino-1-pyrrolidinyl)-N-(3-cyclopropyl-1H-pyrazol-5-yl)pyrrolo[2,1-f][1,2,4]triazin-4-amine | 325.27 | 1.815[a] |
| 92 |  | 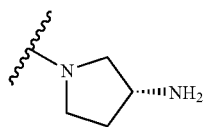 | 2-((3R)-3-amino-1-pyrrolidinyl)-N-(3-cyclopropyl-1H-pyrazol-5-yl)pyrrolo[2,1-f][1,2,4]triazin-4-amine | 325.26 | 1.810[a] |
| 93 | Me | 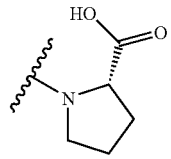 | (2S)-1-(4-((3-methyl-1H-pyrazol-5-yl)amino) pyrrolo[2,1-f][1,2,4]triazin-2-yl)-2-pyrrolidinecarboxylic acid | 328.24 | 2.44[a] |
| 94 | Me | 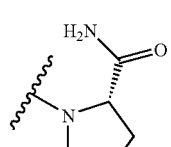 | (2S)-1-(4-((3-methyl-1H-pyrazol-5-yl)amino)pyrrolo[2,1-f][1,2,4]triazin-2-yl)-2-pyrrolidinecarboxamide | 327.24 | 2.055[a] |

TABLE 4-continued

| Ex. No. | R¹ | R² | Compound name | [M + H] | HPLC Ret Time (min) |
|---|---|---|---|---|---|
| 95 | Me | -N(morpholinyl) | N-(3-methyl-1H-pyrazol-5-yl)-2-(4-morpholinyl)pyrrolo [2,1-f][1,2,4]triazin-4-amine | 300.29 | 2.275[b] |
| 96 | cyclopropyl | -N(piperazinyl) | N-(3-cyclopropyl-1H-pyrazol-5-yl)-2-(1-piperazinyl)pyrrolo[2,1-f][1,2,4]triazin-4-amine | 325.27 | 1.837[a] |
| 97 | phenyl | -N(4-aminomethylpiperidinyl) | 2-(4-(aminomethyl)-1-piperidinyl)-N-(3-phenyl-1H-pyrazol-5-yl)pyrrolo[2,1-f][1,2,4]triazin-4-amine | 389.22 | 2438[b] |

HPLC Conditions:
[a]YMC S5 Combiscreen ODS 4.6 × 50 mm, 10-90% aqueous methanol containing 0.2% $H_3PO_4$, 4 min gradient, monitored at 220 or 254 nm)
[b]Chromolith SpeedROD 4.6 × 50 mm, 10-90% aqueous methanol containing 0.1% TFA, 4 min gradient, monitored at 220 or 254 nm)
[c]Phenomenex-luna S10 3.0 × 50 mm, 10-90% aqueous methanol containing 0.2% $H_3PO_4$, 2 min gradient, monitored at 220 or 254 nm
[d]Phenomenex-luna S10 4.6 × 50 mm, 10-90% aqueous methanol containing 0.2% $H_3PO_4$, 3 min gradient, monitored at 220 or 254 nm Example 98

1-(4-(3-Cyclopropyl-1H-pyrazol-5-ylamino)pyrrolo[1,2-f][1,2,4]triazin-2-yl)piperidin-4-yl)methyl)acetamide

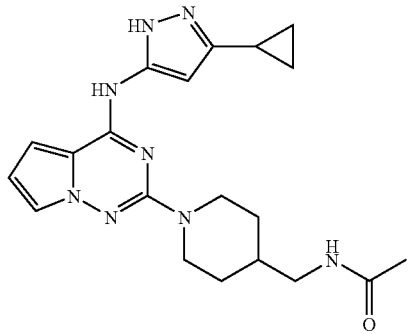

A mixture of 2-(4-(aminomethyl)piperidin-1-yl)-N-(3-cyclopropyl-1H-pyrazol-5-yl)pyrrolo[1,2-f][1,2,4]triazin-4-amine (5 mg, 0.014 mmol) in toluene (5 mL) was treated with acetic anhydride (0.005 mL, 0.05 mmol) and refluxed for 3 h. The reaction was concentrated to dryness and redissolved in MeOH (0.5 mL). aqueous NaOH (0.5 mL, 1M) was added and the mixture was stirred at room temperature for 30 min. The mixture was purified with preparative reversed-phase HPLC (YMC ODS-A 20×100 mm, 10-90% aqueous methanol containing 0.1% TFA, 10 min gradient, monitored at 220 nm) to give N-((1-(4-(3-cyclopropyl-1H-pyrazol-5-ylamino)pyrrolo[1,2-f][1,2,4]triazin-2-yl)piperidin-4-yl)methyl)acetamide (1 mg, 18%). ¹HNMR (DMSO) δ 10.17 (s, 1H), 7.80 (m, 1H), 7.32 (s, 1H), 6.97 (s, 1H), 6.34 (m, 1H), 6.28 (s, 1H), 4.30 (d, 2H, J=12.4 Hz), 2.88 (m, 2 H), 2.70 (m, 2H), 1.86 (m, 1H), 1.75 (s, 3H), 1.60 (m, 3H), 1.07 (m, 2H), 0.90 (m, 2H), 0.61 (m, 2H). HPLC (b). $t_R$=2.47 min. (Chromolith Speed-ROD 4.6×50 mm, 10-90% aqueous methanol containing 0.1% TFA, 4 min gradient, monitored at 220 or 254 nm). m/z=395.26 (M+H).

Example 99

2-(4-Aminopiperidin-1-yl)-N-(3-cyclopropyl-1H-pyrazol-5-yl)-7-(pyrrolidin-1-ylmethyl)pyrrolo[1,2-f][1,2,4]triazin-4-amine

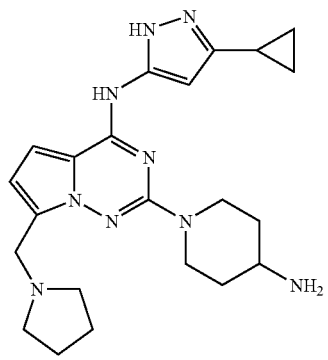

99A. Preparation of 2,4-dichloropyrrolo[1,2-f][1,2,4]triazine-7-carbaldehyde

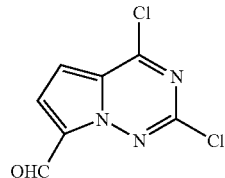

To a solution of POCl$_3$ (1.24 mL, 13.3 mmol) at 0° C. was added DMF (0.52 mL, 6.6 mmol) and the reaction was stirred until gas evolution subsided. The reaction was then warmed to ambient temperature and 2,4-dichloropyrrolo[1,2-f][1,2,4]triazine (250 mg, 1.33 mmol) was added as a solid in one portion. The reaction was warmed to 95° C. and stirred for five hours, then cooled to room temperature. The mixture was poured into ice cold 1:1 saturated aqueous NaHCO$_3$/CH$_2$Cl$_2$ (50 mL). The layers were separated and the aqueous layer extracted with CH$_2$Cl$_2$ (3×25 mL). The combine organic layers were dried (Na$_2$SO$_4$), filtered and concentrated. The crude product was purified by flash chromatography (SiO$_2$, 40 g column, 50% CH$_2$Cl$_2$/Hexanes to 75% CH$_2$Cl$_2$/Hexanes, 25 minute gradient) to afford the desired product as a powder (170 mg, 60%). $^1$HNMR (DMSO) δ 10.3 (s, 1H), 7.68 (d, 1H, J=4.8 Hz), 7.32 (d, 1H, J=4.8 Hz. HPLC $t_R$=2.35 min (YMC S5 Combiscreen ODS 4.6×50 mm, 10-90% aqueous methanol containing 0.2% H$_3$PO$_4$, 4 min gradient, monitored at 254 nm). [M+H]$^+$=216.2.

99B. Preparation of 2-chloro-4-(3-cyclopropyl-1H-pyrazol-5-ylamino)pyrrolo[1,2-f][1,2,4]triazine-7-carbaldehyde

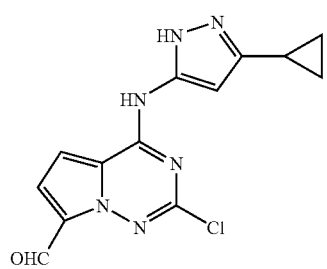

A solution of 99A (170 mg, 0.79 mmol) in iPrOH (1 mL) was treated with 3-cyclopropyl-1H-pyrazol-5-amine (110 mg, 0.79 mmol) and diisopropylethyl amine (0.23 mL, 1.34 mmol). The reaction was allowed to stir at room temperature for 16 hours, and was then cooled to 0° C. The reaction was concentrated to dryness and purified by flash chromatography (SiO$_2$, 40 g column, 100% CH$_2$Cl$_2$ to 5% MeOH/CH$_2$Cl$_2$, 20 minute gradient) to afford the title compound (160 mg, 67%). $^1$HNMR (DMSO) δ 12.4 (s, 1H), 11.5 (s, 1H), 10.2 (s, 1H), 7.46 (d, 1H, J=4.4 Hz), 7.33 (d, 1H, J=5.2 Hz), 6.51 (s, 1H), 1.97 (m, 1H), 0.97 (m, 2H), 0.74 (m, 2H). HPLC $t_R$=3.21 min (YMC S5 Combiscreen ODS 4.6×50 mm, 10-90% aqueous methanol containing 0.2% H3PO4, 4 min gradient, monitored at 254 nm). [M+H]$^+$=303.18.

99C. Preparation of 2-chloro-N-(3-cyclopropyl-1H-pyrazol-5-yl)-7-(pyrrolidin-1-ylmethyl)pyrrolo[1,2-f][1,2,4]triazin-4-amine

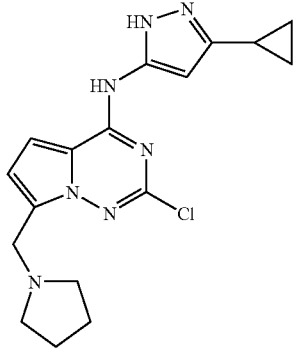

A solution of 99B (110 mg, 0.36 mmol) in dichloroethane (3 mL) was treated with pyrrolidine (0.033 mL, 0.4 mmol) and acetic acid (0.027 mL). To this suspension was added NaBH(OAc)$_3$ (100 mg, 0.47 mmol) and the reaction was stirred for 8 hours. An additional amount of NaBH(OAc)$_3$ (25 mg) was added and the reaction was allowed to stir for an additional 18 hours. The reaction was quenched with 1 N NaOH (10 mL), the layers were separated and the aqueous layer was extracted with CH$_2$Cl$_2$ (3×10 mL). The combined organic layers were dried (Na$_2$SO$_4$), filtered and concentrated. The crude product was purified by preparative reversed phase HPLC to afford the desired compound as a TFA salt. (87 mg, 51%). $^1$HNMR (DMSO) δ 12.4 (s, 1H), 11.5 (s, 1H), 10.2 (s, 1H), 7.46 (d, 1H, J=4.4 Hz), 7.33 (d, 1H, J=5.2 Hz), 6.51 (s, 1H), 1.97 (m, 1H), 0.97 (m, 2H), 0.74 (m, 2H). HPLC $t_R$=2.13 min (YMC S5 Combiscreen ODS 4.6×50 mm, 10-90% aqueous methanol containing 0.2% H$_3$PO$_4$, 4 min gradient, monitored at 254 nm). [M+H]$^+$=358.22.

99D. Preparation of 2-(4-aminopiperidin-1-yl)-N-(3-cyclopropyl-1H-pyrazol-5-yl)-7-(pyrrolidin-1-ylmethyl)pyrrolo[1,2-f][1,2,4]triazin-4-amine

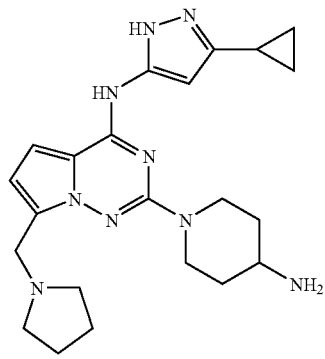

A mixture of 99C (20 mg, 0.056 mmol) and 4-amino piperidine (0.5 mL) was heated to 90° C. in a microwave for 30 minutes at 300 W continuous power. The resulting mixture was purified directly by reversed phase preparative HPLC to afford the title compound (8 mg, 35%). HPLC $t_R$=1.542 min (YMC S5 Combiscreen ODS 4.6×50 mm, 10-90% aqueous methanol containing 0.2% $H_3PO_4$, 4 min gradient, monitored at 254 nm). $[M+H]^+$=422.28.

Example 100

(R)-N-Cyclopropyl-3-(2-(2-(pyridin-2-yl)pyrrolidin-1-yl)pyrrolo[1,2-f][1,2,4]triazin-4-ylamino)-1H-pyrazole-5-carboxamide

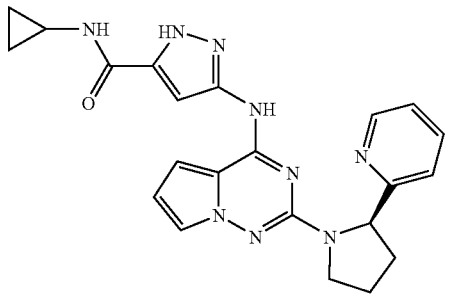

100A. Preparation of N-cyclopropyl-3-nitro-1H-pyrazole-5-carboxamide

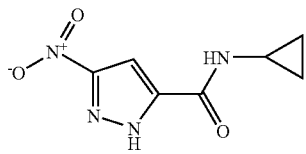

Oxalyl chloride (8.75 mL, 100 mmol) was added to a suspension of 3-nitro-1H-pyrazole-5-carboxylic acid (7.85 g, 50 mmol) in dichloromethane (100 mL) and THF (5.00 mL) at 0° C. and one drop of DMF was then added to the reaction mixture. The reaction mixture was stirred at room temperature for 3 hours. The solvent was evaporated and the residue was redissolved in dichloromethane (100 mL). To the reaction mixture was added a solution of cyclopropanamine (4.16 mL, 60.0 mmol) and pyridine (8.09 mL, 100 mmol) in dichloromethane (10 mL) over a period of 10 minutes. The reaction mixture was stirred overnight and then diluted with ethyl acetate (50 mL), washed with water, dried over $MgSO_4$ and concentrated in vacuo. The crude was purified by silica gel column chromatography (0-5% 2N $NH_3$/$CD_3OD$ichloromethane) to give 9.16 g of N-cyclopropyl-3-nitro-1H-pyrazole-5-carboxamide. MS (ESI) m/z 197.1 (M+H). $^1H$ NMR ($CD_3OD$) δ ppm 7.38 (s, 1H), 2.81-2.86 (m, 1H), 0.82 (td, J=7.08, 5.36 Hz, 2H), 0.62-0.68 (m, 2H).

100B. Preparation of 3-amino-N-cyclopropyl-1H-pyrazole-5-carboxamide

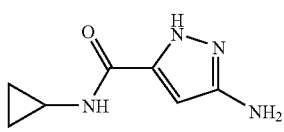

N-cyclopropyl-3-nitro-1H-pyrazole-5-carboxamide (1.0 g, 5.10 mmol) and platinum (iv) oxide (0.116 g, 0.510 mmol) in ethanol were hydrogenated at 50 psi for 2 hours. The reaction mixture was filtrated through Celite and the filtrate was concentrated to give 0.916 g of 3-amino-N-cyclopropyl-1H-pyrazole-5-carboxamide as a solid. The crude was used without purification. MS (ESI) m/z 167.1 (M+H).

100C. Preparation of 3-(2-chloropyrrolo[1,2-f][1,2,4]triazin-4-ylamino)-N-cyclopropyl-1H-pyrazole-5-carboxamide

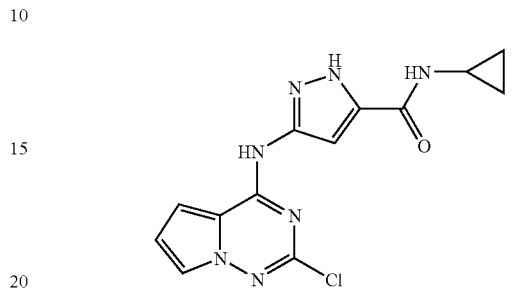

2,4-dichloropyrrolo[1,2-f][1,2,4]triazine (0.865 g, 4.6 mmol) was added to a solution of 3-amino-N-cyclopropyl-1H-pyrazole-5-carboxamide (0.917 g, 5.52 mmol) and triethylamine (0.962 mL, 6.90 mmol) in 2-propanol (40 mL) and the reaction mixture was stirred at 40° C. overnight. The precipitate was collected to give 0.91 g of 3-(2-chloropyrrolo[1,2-f][1,2,4]triazin-4-ylamino)-N-cyclopropyl-1H-pyrazole-5-carboxamide as a solid. MS (ESI) m/z 318.1 (M+H). $^1H$ NMR (DMSO-d6) δ ppm 13.34 (s, 1H), 11.15 (s, 1H), 8.65 (s, 1H), 7.76 (s, 1H), 7.32 (s, 1H), 7.22 (s, 1HO, 6.71 (s, 1H), 2.78-2.85 9 m, 1H), 0.67-0.73 (m, 2H), 0.57-0.61 (m, 2H).

100D. Preparation of (R)-N-cyclopropyl-3-(2-(2-(pyridin-2-yl)pyrrolidin-1-yl)pyrrolo[1,2-f][1,2,4]triazin-4-ylamino)-1H-pyrazole-5-carboxamide

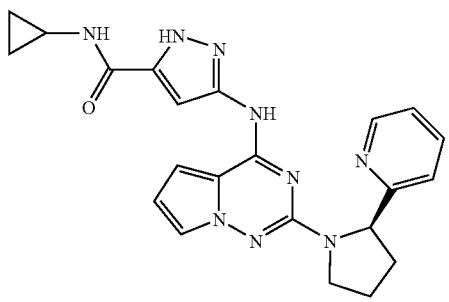

A mixture of 3-(2-chloropyrrolo[1,2-f][1,2,4]triazin-4-ylamino)-N-cyclopropyl-1H-pyrazole-5-carboxamide (60 mg, 0.189 mmol), (R)-2-(pyrrolidin-2-yl)pyridine (28.0 mg, 0.189 mmol) and diisopropylethylamine (0.049 mL, 0.283 mmol) in NMP (0.5 mL) was heated at 130° C. for 48 h. The reaction mixture was diluted with MeOH/$H_2O$ and purified by preparative HPLC using the conditions as outlined below.
Column: Waters Sunflower C-18 19×100 mm
Gradient: 25-100% aqueous methanol over 10 minutes containing 0.1% TFA
Flow rate: 20 mL/min
Retention time: 5.7 min
The resulting TFA salt was converted to free base by a cation exchange column to give 51 mg of (R)-N-cyclopropyl-3-(2-(2-(pyridin-2-yl)pyrrolidin-1-yl)pyrrolo[1,2-f][1,2,4]triazin-4-ylamino)-1H-pyrazole-5-carboxamide as a solid. MS (ESI) 430 (M+H). $^1H$ NMR ($CD_3OD$) δ ppm 8.67 (d, J=5.50 Hz, 1H), 8.54 (t, J=7.70 Hz, 1H), 8.09 (d, J=7.97 Hz, 1H), 7.93 (t, J=6.74 Hz, 1H), 7.43 (s, 1H), 7.10 (d, J=3.85 Hz, 1H), 6.68 (s, 1H), 6.61 (dd, J=4.54, 2.34 Hz, 1H), 5.46 (dd, J=8.80, 3.02 Hz, 1H), 4.08 (br. s, 1H), 3.82-3.88 (m, 1H), 2.85-2.91 (m, 1H), 2.66-2.75 (m, 1H), 2.14-2.26 (m, 3H), 0.81-0.88 (m, 2H), 0.65-0.71 (m, 2H).

Example 101

(S)-N-Cyclopropyl-3-(2-(2-(pyridin-2-yl)pyrrolidin-1-yl)pyrrolo[1,2-f][1,2,4]triazin-4-ylamino)-1H-pyrazole-5-carboxamide

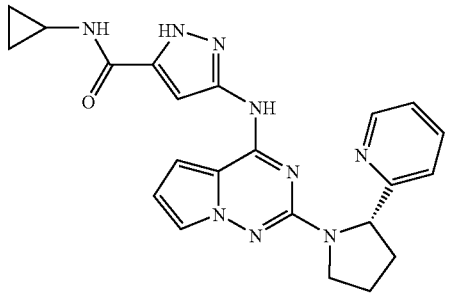

A mixture of 3-(2-chloropyrrolo[1,2-f][1,2,4]triazin-4-ylamino)-N-cyclopropyl-1H-pyrazole-5-carboxamide (60 mg, 0.189 mmol) (Example 100C), (S)-2-(pyrrolidin-2-yl)pyridine (28.0 mg, 0.189 mmol) and diisopropylethylamine (0.049 mL, 0.283 mmol) in NMP (0.5 mL) was heated at 130° C. for 48 hours. The reaction mixture was diluted with MeOH/H$_2$O and purified by preparative HPLC using the conditions as outlined below.
Column: Waters Sunflower C-18 19×100 mm
Gradient: 25-100% aqueous methanol over 10 minutes containing 0.1% TFA
Flow rate: 20 mL/min
Retention time: 5.8 min
The resulting TFA salt was converted to the free base by passing through a SCX column. to furnish 24 mg of (S)-N-cyclopropyl-3-(2-(2-(pyridin-2-yl)pyrrolidin-1-yl)pyrrolo[1,2-f][1,2,4]triazin-4-ylamino)-1H-pyrazole-5-carboxamide as a solid. MS (ESI) m/z 430 (M+H). $^1$H NMR (CD$_3$OD) δ ppm 8.46 (s, 1H), 7.63 (s, 1H), 7.26 (s, 2H), 7.12 (s, 1H), 6.71 (d, J=3.85 Hz, 1H), 6.37 (s, 1H), 5.20 (s, 1H), 3.80-3.86 (m, 1H), 3.64 (s, 1H), 2.75 (s, 1H), 2.42 (s, 1H), 1.96 (s, 3H), 0.74 (s, 2H), 0.58 (s, 2H).

Example 102

N-Cyclopropyl-3-(2-(2-phenylpyrrolidin-1-yl)pyrrolo[1,2-f][1,2,4]triazin-4-ylamino)-1H-pyrazole-5-carboxamide

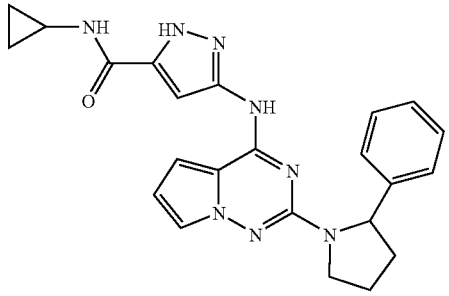

A mixture of 3-(2-chloropyrrolo[1,2-f][1,2,4]triazin-4-ylamino)-N-cyclopropyl-1H-pyrazole-5-carboxamide (30 mg, 0.094 mmol) (Example 100C), 2-phenylpyrrolidine (13.90 mg, 0.094 mmol) and diisopropylethylamine (0.025 mL, 0.142 mmol) in NMP (0.4 mL) was heated at 130° C. overnight. The reaction mixture was diluted with MeOH/H$_2$O and purified by preparative HPLC using the conditions as shown below.
Column: Waters Sunflower C-18 19×100 mm
Gradient: 25-100% aqueous methanol over 10 minutes containing 0.1% TFA
Flow rate: 20 mL/min
Retention time: 11.3 min
The resulting TFA salt was converted to the free base by passing through a SCX column to obtain 21 mg of N-cyclopropyl-3-(2-(2-phenylpyrrolidin-1-yl)pyrrolo[1,2-f][1,2,4]triazin-4-ylamino)-1H-pyrazole-5-carboxamide as a solid. MS (ESI) m/z 429.1 (M+H). $^1$H NMR (CD$_3$OD) δ ppm 7.38 (s, 1H), 7.29 (s, 4H), 7.16 (s, 1H), 6.79 (d, J=3.85 Hz, 1H), 6.47 (s, 1H), 5.31 (s, 1H), 3.89 (d, J=4.12 Hz, 1H), 3.66-3.72 (m, 1H), 2.78-2.84 (m, 1H), 2.39-2.48 (m, 1H), 1.97-2.04 (m, 2H), 1.88-1.96 (m, 1H), 0.78-0.86 (m, 2H), 0.66 (br s, 2H).

Example 103

N-Cyclopropyl-3-(2-(2-(thiazol-2-yl)pyrrolidin-1-yl)pyrrolo[1,2-f][1,2,4]triazin-4-ylamino)-1H-pyrazole-5-carboxamide

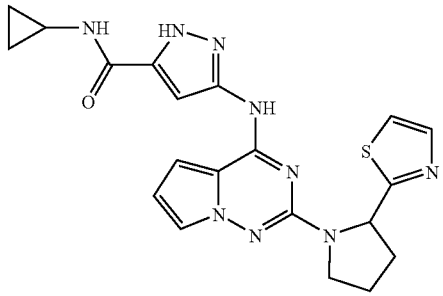

A mixture of 3-(2-chloropyrrolo[1,2-f][1,2,4]triazin-4-ylamino)-N-cyclopropyl-1H-pyrazole-5-carboxamide (30 mg, 0.094 mmol) (Example 100C), 2-(pyrrolidin-2-yl)thiazole (21.84 mg, 0.142 mmol) and diisopropylethylamine (0.033 mL, 0.189 mmol) in NMP (0.4 mL) was heated at 220° C. for 1 h in a microwave reactor. The reaction mixture was diluted with MeOH/H$_2$O and purified by preparative HPLC using the conditions as outlined below.
Column: Waters Sunflower C-18 19×100 mm
Gradient: 25-100% aqueous methanol over 10 minutes containing 0.1% TFA
Flow rate: 20 mL/min
Retention time: 11.4 min
The resulting TFA salt was converted to free base by passing through a SCX column to give 7.4 mg of N-cyclopropyl-3-(2-(2-(thiazol-2-yl)pyrrolidin-1-yl)pyrrolo[1,2-f][1,2,4]triazin-4-ylamino)-1H-pyrazole-5-carboxamide as a solid. MS (ESI) 436.1 (M+H). $^1$H NMR (CD$_3$OD) δ ppm 7.71 (br s, 1H), 7.39 (s, 2H), 6.83 (dd, J=4.40, 1.37 Hz, 1H), 6.48 (s, 1H), 5.61 (s, 1H), 3.82-3.88 (m, 1H), 3.56-3.67 (m, 1H), 2.88 (br s, 1H), 2.44-2.53 (m, 1H), 2.04-2.27 (m, 3H), 0.85 (br s, 2H), 0.70 (br s, 2H)

Example 104

(S)-N-Cyclopropyl-3-(2-(3-(pyridin-2-yl)pyrrolidin-1-yl)pyrrolo[1,2-f][1,2,4]triazin-4-ylamino)-1H-pyrazole-5-carboxamide

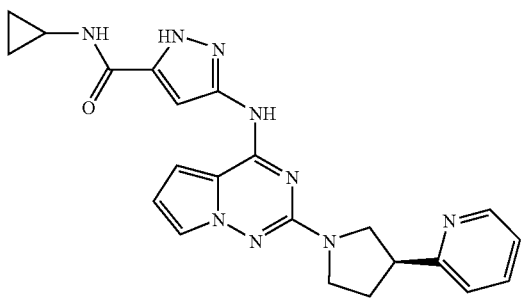

A mixture of 3-(2-chloropyrrolo[1,2-f][1,2,4]triazin-4-ylamino)-N-cyclopropyl-1H-pyrazole-5-carboxamide (30 mg, 0.094 mmol) (Example 100C), (S)-2-(pyrrolidin-3-yl)pyridine (20.99 mg, 0.142 mmol) and diisoprpylethylamine (0.033 mL, 0.189 mmol) in NMP (0.4 mL) was heated at 220° C. for 1 h in a microwave reactor. The reaction mixture was diluted with MeOH/H₂O and purified by preparative HPLC using conditions as shown below.

Column: Waters Sunflower C-18 19×100 mm
Gradient: 25-100% aqueous methanol over 10 minutes containing 0.1% TFA
Flow rate: 20 mL/min
Retention time: 8.2 min The resulting TFA salt was converted to the free base by passing through a SCX column to furnish 2.9 mg of (S)-N-cyclopropyl-3-(2-(3-(pyridin-2-yl)pyrrolidin-1-yl)pyrrolo[1,2-f][1,2,4]triazin-4-ylamino)-1H-pyrazole-5-carboxamide as a solid. MS (ESI) m/z 430 (M+H). ¹H NMR (CDCl₃) δ ppm 8.63 (d, J=1.92 Hz, 1H), 8.44 (d, J=3.57 Hz, 1H), 7.60 (d, J=7.97 Hz, 1H), 7.39 (t, J=1.92 Hz, 1H), 7.24-7.26 (m, 2H), 6.45 (dd, J=4.40, 2.47 Hz, 1H), 5.26 (dd, J=5.78, 2.47 Hz, 1H), 3.86-3.92 (m, 1H), 3.70-3.76 (m, 1H), 3.05 (br s, 1H), 2.41-2.49 (m, 2H), 2.01-2.07 (m, 2H), 1.92-1.99 (m, 1H), 1.60 (br s, 1H), 0.88-0.97 (m, 4H).

Example 105

(R)-N-Cyclopropyl-3-(2-(3-(pyridin-2-yl)pyrrolidin-1-yl)pyrrolo[1,2-f][1,2,4]triazin-4-ylamino)-1H-pyrazole-5-carboxamide

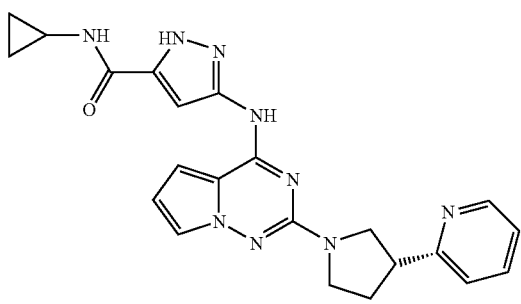

A mixture of 3-(2-chloropyrrolo[1,2-f][1,2,4]triazin-4-ylamino)-N-cyclopropyl-1H-pyrazole-5-carboxamide (30 mg, 0.094 mmol) (Example 100C), (R)-2-(pyrrolidin-3-yl)pyridine (13.99 mg, 0.094 mmol) and diisopropylethylamine (0.082 mL, 0.472 mmol) in NMP (2 mL) was heated at 200° C. for 8 hours. The reaction mixture was diluted with methanol/water and purified by preparative HPLC using the same conditions as outlined for Example 104 (Retention time 8.2 min). The resulting TFA salt of (R)-N-cyclopropyl-3-(2-(3-(pyridin-2-yl)pyrrolidin-1-yl)pyrrolo[1,2-f][1,2,4]triazin-4-ylamino)-1H-pyrazole-5-carboxamide was converted to free base by passing through a SCX column to give 5.7 mg as a solid. MS (ESI) m/z 430 (M+H). ¹H NMR (CD₃OD) δ ppm 8.73 (s, 1H), 8.65 (d, J=5.50 Hz, 1H), 8.53 (d, J=7.97 Hz, 1H), 7.96 (dd, J=8.11, 5.91 Hz, 1H), 7.36 (s, 1H), 6.84 (dd, J=4.40, 1.37 Hz, 1H), 6.56 (s, 1H), 6.50 (dd, J=4.67, 2.47 Hz, 1H), 5.40 (dd, J=8.39, 2.61 Hz, 1H), 3.93-3.98 (m, 1H), 3.76-3.84 (m, 1H), 2.81-2.89 (m, 2H), 2.56-2.65 (m, 1H), 1.98-2.15 (m, 4H), 0.80-0.87 (m, 2H), 0.63-0.70 (m, 2H).

Example 106

N-Cyclopropyl-3-(2-(2-phenylpiperidin-1-yl)pyrrolo[1,2-f][1,2,4]triazin-4-ylamino)-1H-pyrazole-5-carboxamide

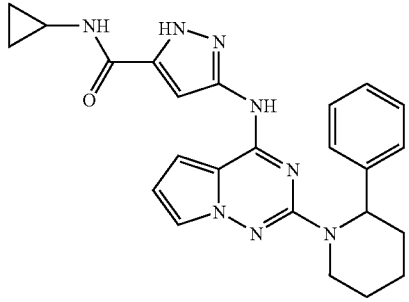

A mixture of 3-(2-chloropyrrolo[1,2-f][1,2,4]triazin-4-ylamino)-N-cyclopropyl-1H-pyrazole-5-carboxamide (30 mg, 0.094 mmol) (Example 100C), 2-phenylpiperidine (228 mg, 1.416 mmol) was heated neat at 180° C. overnight. The reaction mixture was diluted with MeOH/H₂O and purified by preparative HPLC using the same conditions as outlined for Example 104 (Retention time: 11 min). The resulting TFA salt was converted to the free base by passing through a SCX column to give 5.7 mg of N-cyclopropyl-3-(2-(2-phenylpiperidin-1-yl)pyrrolo[1,2-f][1,2,4]triazin-4-ylamino)-1H-pyrazole-5-carboxamide as a solid. MS (ESI) m/z 443.2 (M+H). ¹H NMR (CD₃OD) δ ppm 7.46 (s, 1H), 7.28-7.34 (m, 4H), 7.16-7.21 (m, 1H), 6.95 (d, J=3.57 Hz, 1H), 6.70 (s, 1H), 6.55-6.58 (m, 1H), 5.71-5.75 (m, 1H), 4.33 (d, J=12.92 Hz, 1H), 3.15-3.21 (m, 1H), 2.78-2.83 (m, 1H), 2.35-2.41 (m, 1H), 2.03-2.11 (m, 1H), 1.66-1.75 (m, 3H), 1.5-1.63 (m, 1H), 0.77-0.84 (m, 2H), 0.60-0.66 (m, 2H).

Example 107

(S)-N-Cyclopropyl-3-(2-(2-(hydroxymethyl)pyrrolidin-1-yl)pyrrolo[1,2-f][1,2,4]triazin-4-ylamino)-1H-pyrazole-5-carboxamide

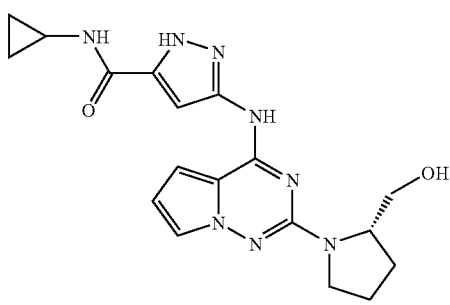

A mixture of 3-(2-chloropyrrolo[1,2-f][1,2,4]triazin-4-ylamino)-N-cyclopropyl-1H-pyrazole-5-carboxamide (30 mg, 0.094 mmol) (Example 100C), (S)-pyrrolidin-2-ylmethanol (11.46 mg, 0.113 mmol) and diisopropylethylamine (0.082 mL, 0.472 mmol) in NMP (1 mL) was heated at 200° C. for 6 h. The reaction mixture was diluted with MeOH/water and purified by preparative HPLC using the same conditions as outlined for Example 104 (Retention time: 9 min). The resulting TFA salt was converted to free base by passing through a SCX column to give 18 mg (S)—N-cyclopropyl-3-(2-(2-(hydroxymethyl)pyrrolidin-1-yl)pyrrolo[1,2-f][1,2,4]triazin-4-ylamino)-1H-pyrazole-5-carboxamide as a solid. MS (ESI) m/z 383 (M+H). $^1$H NMR (CD$_3$OD) δ ppm 7.51 (t, J=1.685 Hz, 1H), 7.08 (d, J=3.85 Hz, 1H), 6.93 (s, 1H), 6.59 (dd, J=4.67, 2.47 Hz, 1H), 4.18-4.24 (m, 1H), 3.77 (dd, J=10.86, 5.09 Hz, 1H), 3.56-3.65 (m, 2H), 3.46-3.55 (m, 1H), 2.80-2.86 (m, 1H), 2.02-2.11 (m, 4H), 0.81 (td, J=7.08, 5.09 Hz, 2H), 0.62-0.69 (m, 2H).

Example 108

(R)-N-Cyclopropyl-3-(2-(2-(hydroxymethyl)pyrrolidin-1-yl)pyrrolo[1,2-f][1,2,4]triazin-4-ylamino)-1H-pyrazole-5-carboxamide

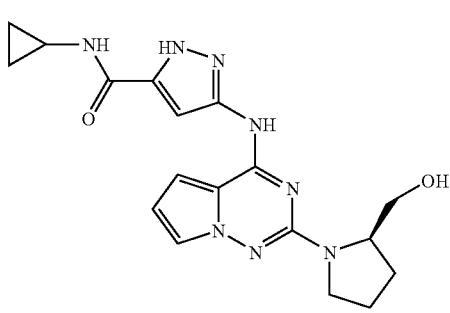

A mixture of 3-(2-chloropyrrolo[1,2-f][1,2,4]triazin-4-ylamino)-N-cyclopropyl-1H-pyrazole-5-carboxamide (50 mg, 0.157 mmol) (Example 100C), (R)-pyrrolidin-2-ylmethanol (31.8 mg, 0.315 mmol) and diisopropylethylamine (0.110 mL, 0.629 mmol) in NMP (1 mL) was heated at 200° C. for 3 hours. The reaction mixture was diluted with methanol/water and purified by preparative HPLC using the same conditions as shown for Example 104 (Retention time: 8.93 min). The resulting TFA salt was converted to free base by passage through a SCX column to obtain 30 mg of (R)-N-cyclopropyl-3-(2-(2-(hydroxymethyl)pyrrolidin-1-yl)pyrrolo[1,2-f][1,2,4]triazin-4-ylamino)-1H-pyrazole-5-carboxamide as a solid. MS (ESI) m/z 383 (M+H). $^1$H NMR (CD$_3$OD) δ ppm 7.46-7.48 (m, 1H), 7.02 (d, J=3.85 Hz, 1H), 6.95 (s, 1H), 6.55 (dd, J=4.67, 2.47 Hz, 1H), 4.18-4.24 (m, 1H), 3.79 (dd, J=11.00, 4.95 Hz, 1H), 3.54-3.62 (m, 2H), 3.43-3.51 (m, 1H), 2.80-2.86 (m, 1H), 2.00-2.10 (m, 4H), 0.81 (td, J=7.08, 5.09 Hz, 2H), 0.62-0.69 (m, 2H).

Example 109

3-(2-(3-Acetamidopyrrolidin-1-yl)pyrrolo[1,2-f][1,2,4]triazin-4-ylamino)-N-cyclopropyl-1H-pyrazole-5-carboxamide

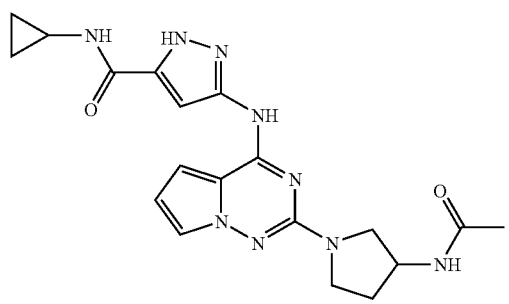

A mixture of 3-(2-chloropyrrolo[1,2-f][1,2,4]triazin-4-ylamino)-N-cyclopropyl-1H-pyrazole-5-carboxamide (30 mg, 0.094 mmol) (Example 100C), N-(pyrrolidin-3-yl)acetamide (24.20 mg, 0.189 mmol) and diisopropylethylamine (0.066 mL, 0.378 mmol) in NMP (1 mL) was heated at 180° C. for 4 h. The reaction mixture was diluted with methanol/water and purified by preparative HPLC using the same conditions as outlined for Example 104 (Retention time 7.731 min). The resulting TFA salt was converted to free base by passing through a SCX column to furnish 27 mg of 3-(2-(3-acetamidopyrrolidin-1-yl)pyrrolo[1,2-f][1,2,4]triazin-4-ylamino)-N-cyclopropyl-1H-pyrazole-5-carboxamide as a solid. MS (ESI) m/z 410 (M+H). $^1$H NMR (CD$_3$OD) δ ppm 7.53-7.56 (m, 1H), 7.12 (dd, J=4.61, 1.32 Hz, 1H), 6.80 (s, 1H), 6.62 (dd, J=4.72, 2.53 Hz, 1H), 4.44-4.51 (m, 1H), 3.84 (dd, J=10.55, 6.37 Hz, 1H), 3.67-3.72 (m, 1H), 3.59-3.65 (m, 1H), 3.44 (dd, J=10.44, 4.50 Hz, 1H), 2.84 (ddd, J=7.36, 3.63, 3.52 Hz, 1H), 2.27-2.36 (m, 1H), 2.00-2.09 (m, 1H), 1.97 (s, 3H), 0.82 (td, J=7.20, 5.16 Hz, 2H), 0.62-0.71 (m, 2H).

Example 110

(S)-3-(2-(2-(1,2,4-Thiadiazol-5-yl)pyrrolidin-1-yl)pyrrolo[1,2-f][1,2,4]triazin-4-ylamino)-N-cyclopropyl-1H-pyrazole-5-carboxamide

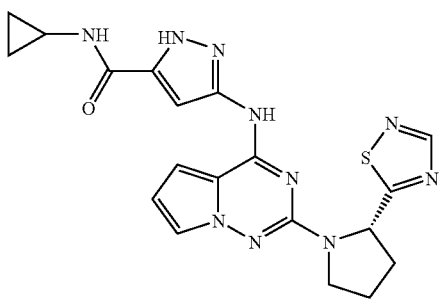

A mixture of 3-(2-chloropyrrolo[1,2-f][1,2,4]triazin-4-ylamino)-N-cyclopropyl-1H-pyrazole-5-carboxamide (50 mg, 0.157 mmol) (Example 100C), (S)-5-(pyrrolidin-2-yl)-1,2,4-thiadiazole (48.9 mg, 0.315 mmol) and diisopropylethylamine (0.110 mL, 0.629 mmol) in NMP (0.4 mL) was heated at 200° C. for 3 h. The reaction mixture was diluted with methanol/water and purified by preparative HPLC using same conditions as of Example 104 (Retention time: 9.893 min). The resulting TFA salt was converted to the free base by passing through a SCX column to afford 8 mg of (S)-3-(2-(2-(1,2,4-thiadiazol-5-yl)pyrrolidin-1-yl)pyrrolo[1,2-f][1,2,4]triazin-4-ylamino)-N-cyclopropyl-1H-pyrazole-5-carboxamide. MS (ESI) m/z 437 (M+H). $^1$H NMR (CD$_3$OD and CDCl$_3$ mixture) δ ppm 8.62 (s, 1H), 7.40 (t, J=1.65 Hz, 1H), 6.85 (d, J=4.40 Hz, 1H), 6.49 (dd, J=4.54, 2.34 Hz, 1H), 5.70 (s, 1H), 3.85-3.90 (m, 1H), 3.59-3.66 (m, 1H), 2.85 (br s, 1H), 2.47-2.54 (m, 1H), 2.14-2.28 (m, 3H), 0.85 (d, J=6.87 Hz, 2H), 0.70 (s, 2H).

Example 111

N-Cyclopropyl-3-(2-(2-(pyridin-3-yl)pyrrolidin-1-yl)pyrrolo[1,2-f][1,2,4]triazin-4-ylamino)-1H-pyrazole-5-carboxamide

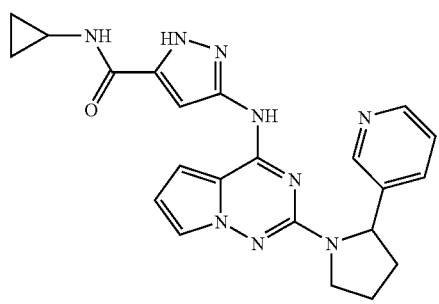

A mixture of 3-(2-chloropyrrolo[1,2-f][1,2,4]triazin-4-ylamino)-N-cyclopropyl-1H-pyrazole-5-carboxamide (40 mg, 0.126 mmol) (Example 100C), 3-(pyrrolidin-2-yl)pyridine (37.3 mg, 0.252 mmol) and diisopropylethylamine (0.088 mL, 0.504 mmol) in NMP (1 mL) was heated at 200° C. for 4 h. The reaction mixture was diluted with methanol/water and purified by preparative HPLC using same conditions as applied to Example 104 (Retention time: 6.7 min). The product from preparative HPLC contained about 10% impurities and thus was first converted to free base by passing through a SCX column and then purified by prep-TLC on silica gel plate (5% 2M ammonia in methanol-dichloromethane) to obtain 26 mg of N-cyclopropyl-3-(2-(2-(pyridin-3-yl)pyrrolidin-1-yl)pyrrolo[1,2-f][1,2,4]triazin-4-ylamino)-1H-pyrazole-5-carboxamide as a solid. MS (ESI) m/z 430.2 (M+H). $^1$H NMR (CD$_3$OD) δ ppm 8.72 (s, 1H), 8.64 (d, J=5.77 Hz, 1H), 8.52 (d, J=8.25 Hz, 1H), 7.96 (dd, J=8.25, 5.77 Hz, 1H), 7.35 (s, 1H), 6.83 (dd, J=4.67, 1.37 Hz, 1H), 6.56 (s, 1H), 6.50 (dd, J=4.67, 2.47 Hz, 1H), 5.40 (dd, J=8.39, 2.61 Hz, 1H), 3.97 (s, 1H), 3.93-3.97 (m, 1H), 3.76-3.82 (m, 1H), 2.81-2.89 (m, 1H), 2.57-2.65 (m, 1H), 2.02-2.11 (m, 3H), 0.80-0.88 (m, 2H), 0.64-0.71 (m, 2H).

Example 112

N-Cyclopropyl-3-(2-(2-(pyridin-4-yl)pyrrolidin-1-yl)pyrrolo[1,2-f][1,2,4]triazin-4-ylamino)-1H-pyrazole-5-carboxamide

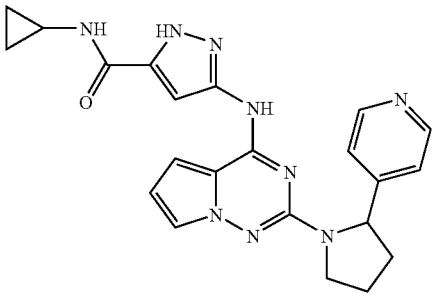

A mixture of 3-(2-chloropyrrolo[1,2-f][1,2,4]triazin-4-ylamino)-N-cyclopropyl-1H-pyrazole-5-carboxamide (40 mg, 0.126 mmol) (Example 100C), 4-(pyrrolidin-2-yl)pyridine (37.3 mg, 0.252 mmol) and diisopropylethylamine (0.088 mL, 0.504 mmol) in NMP (1 mL) was heated at 200° C. for 4 h. The reaction mixture was diluted with methanol/water and purified by preparative HPLC using same conditions as applied for Example 104 (Retention time: 6.6 min). The product from preparative HPLC was converted to the free base through a SCX column and then purified by silica gel prep-TLC (5% 2M ammonia in methanol-dichloromethane) to give 23 mg of N-cyclopropyl-3-(2-(2-(pyridin-4-yl)pyrrolidin-1-yl)pyrrolo[1,2-f][1,2,4]triazin-4-ylamino)-1H-pyrazole-5-carboxamide as a solid. MS (ESI) m/z 432 (M+H). $^1$H NMR (CDCl$_3$) δ ppm 8.53 (d, J=6.05 Hz, 2H), 7.35 (s, 1H), 7.25 (t, J=2.89 Hz, 2H), 6.39 (dd, J=4.12, 2.20 Hz, 1H), 6.28 (br s, 1H), 5.19 (d, J=7.97 Hz, 2H), 3.80-3.88 (m, 1H), 3.65-3.73 (m, 1H), 2.83 (s, 1H), 2.38-2.46 (m, 1H), 1.90-1.99 (m, 4H), 1.86 (s, 1H), 0.87 (s, 2H), 0.68 (s, 2H).

Example 113

(S)-N-(5-Methyl-1H-pyrazol-3-yl)-2-(2-(pyridin-2-yl)pyrrolidin-1-yl)pyrrolo[1,2-f][1,2,4]triazin-4-amine TFA salt

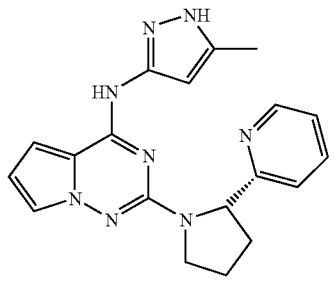

113A. Preparation of 2-chloro-N-(5-methyl-1H-pyrazol-3-yl)pyrrolo[1,2-f][1,2,4]triazin-4-amine

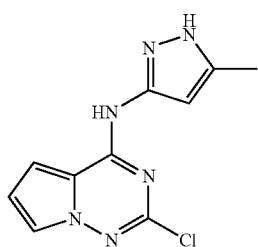

3-Methyl-1H-pyrazol-5-amine (387 mg, 3.99 mmol) was added to a stirred suspension of 2,4-dichloropyrrolo[1,2-f][1,2,4]triazine (500 mg, 2.66 mmol) in a mixture of 2-propanol and triethylamine (4:0.2 mL). The reaction mixture was stirred at 45° C. for 16 hours. The reaction mixture was cooled at room temperature and concentrated in vacuo. The crude was purified using silica gel column chromatography (dichloromethane-methanol (98:2 to 94:6) gradient). The fractions were collected, analyzed, combined and concentrated to afford 350 mg of 2-chloro-N-(5-methyl-1H-pyrazol-3-yl)pyrrolo[1,2-f][1,2,4]triazin-4-amine. MS (ESI) m/z 249.06 (M+H). $^1$H NMR (CDCl$_3$) δ ppm 8.75 (s, 1H), 7.66 (s, 1H), 6.71 (s, 1H), 6.05 (br s, 1H), 2.27 (s, 3H).

113B. Preparation of (S)-N-(5-methyl-1H-pyrazol-3-yl)-2-(2-(pyridin-2-yl)pyrrolidin-1-yl)pyrrolo[1,2-f][1,2,4]triazin-4-amine TFA salt

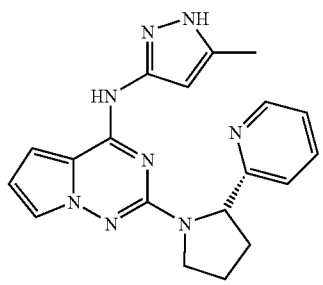

2(S)-Pyrrolidin-2-ylpyridine (447 mg, 3.0 mmol) was added to the mixture containing 2-chloro-N-(5-methyl-1H-pyrazol-3-yl)pyrrolo[1,2-f][1,2,4]triazin-4-amine (250 mg, 1.00 mmol) and diisopropylethylamine (780 mg, 6.03 mmol) in NMP. The reaction mixture was heated at 130° C. for 72 hours and then diluted with ethyl acetate-water (20 mL, 4:1). The organic layer was separated and washed with water, dried (Na$_2$SO$_4$) and concentrated to afford the crude product. The crude product was dissolved in methanol and purified using preparative HPLC using conditions as shown below to give 92 mg of (S)-N-(5-methyl-1H-pyrazol-3-yl)-2-(2-(pyridin-2-yl)pyrrolidin-1-yl)pyrrolo[1,2-f][1,2,4]triazin-4-amine as the TFA salt.

Column: YMC ODS S5 35×100 mm
Gradient: 10-100% aqueous methanol over 12 minutes containing 0.1% TFA
Flow rate: 20 mL/min
Retention time: 9 min MS (ESI) m/z 361.18 (M+H). $^1$H NMR (CD$_3$OD) δ ppm 8.75 (d, J=5.4 Hz, 1H), 8.48 (dd, J=7.66, 2.2, 1H), 8.2 (d, J=8 Hz), 1H), 7.86 (dd, J=5.8, 1.9 Hz, 1H), 7.55 (s, 1H), 6.93 (d, J=4.8 Hz, 1H), 6.51 (d, J=4.8 Hz, 1H), 5.45 (m, 1H), 3.92 (m, 1H), 3.76 (m, 1H), 2.62 (m, 1H), 2.29 (s, 3H), 2.16 (m, 4H).

Example 114

(R)-N-(5-Methyl-1H-pyrazol-3-yl)-2-(2-(pyridin-2-yl)pyrrolidin-1-yl)pyrrolo[1,2-f][1,2,4]triazin-4-amine TFA salt

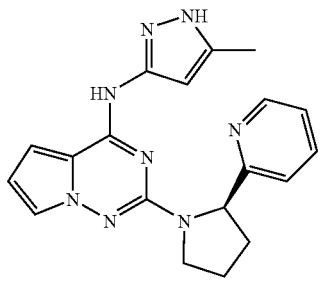

2(R)-Pyrrolidin-2-ylpyridine (447 mg, 3.0 mmol) was added to a mixture containing 2-chloro-N-(5-methyl-1H-pyrazol-3-yl)pyrrolo[1,2-f][1,2,4]triazin-4-amine (250 mg, 1.00 mmol) (Example 113A) and diisopropylethylamine (780 mg, 6.03 mmol) in NMP. The reaction mixture was heated at 130° C. for 72 hours and then reaction mixture diluted with ethyl acetate:water (20 mL, 4:1). The organic layer was separated and washed with water, dried (Na$_2$SO$_4$) and concentrated to afford the crude product. The crude product was dissolved in methanol and purified using preparative HPLC using the conditions shown below to afford 80 mg of (R)-N-(5-methyl-1H-pyrazol-3-yl)-2-(2-(pyridin-2-yl)pyrrolidin-1-yl)pyrrolo[1,2-f][1,2,4]triazin-4-amine as the TFA salt.

Column: YMC ODS S5 35×100 mm
Gradient: 10-100% aqueous methanol over 12 minutes containing 0.1% TFA
Flow rate: 20 mL/min
Retention time: 9 min MS (ESI) m/z 361.18 (M+H). $^1$H NMR (CD$_3$OD) δ ppm 8.75 (d, J=5.4 Hz, 1H), 8.48 (dd, J=7.66, 2.2, 1H), 8.2 (d, J=8 Hz), 1H), 7.86 (dd, J=5.8, 1.9 Hz, 1H), 7.55 (s, 1H), 6.93 (d, J=4.8 Hz, 1H), 6.51 (d, J=4.8 Hz, 1H), 5.45 (m, 1H), 3.92 (m, 1H), 3.76 (m, 1H), 2.62 (m, 1H), 2.29 (s, 3H), 2.16 (m, 4H).

Example 115

N-(5-tert-Butyl-1H-pyrazol-3-yl)-2-(2-(pyridin-2-yl)pyrrolidin-1-yl)pyrrolo[1,2-f][1,2,4]triazin-4-amine TFA salt

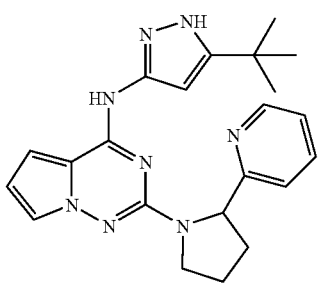

115A. Preparation of N-(5-tert-butyl-1H-pyrazol-3-yl)-2-chloropyrrolo[1,2-f][1,2,4]triazin-4-amine

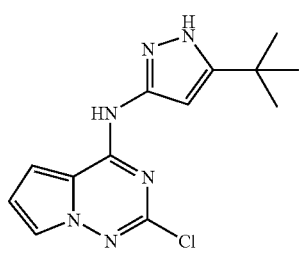

3-tert-Butyl-1H-pyrazol-5-amine (222 mg, 1.6 mmol) was added to a stirred suspension of 2,4-dichloropyrrolo[1,2-f][1,2,4]triazine (250 mg, 1.3 mmol) (Example 1, Part B) in a mixture of 2-propanol (2 mL) and triethylamine (0.2 mL). The reaction mixture was stirred at 45° C. for 16 hours. The reaction mixture was cooled at room temperature and concentrated in vacuo. The crude was purified using silica gel column chromatography (dichloromethane-methanol (98:2 to 94:6) gradient).to afford 290 mg of the N-(5-tert-butyl-1H-pyrazol-3-yl)-2-chloropyrrolo[1,2-f][1,2,4]triazin-4-amine. MS (ESI) m/z 291 (M+H).

115B. Preparation of N-(5-tert-butyl-1H-pyrazol-3-yl)-2-(2-(pyridin-2-yl)pyrrolidin-1-yl)pyrrolo[1,2-f][1,2,4]triazin-4-amine TFA salt

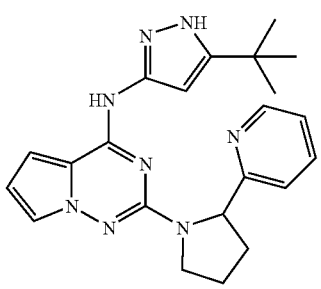

2-Pyrrolidin-2-ylpyridine (204 mg, 1.3 mmol) was added to a mixture containing N-(5-tert-butyl-1H-pyrazol-3-yl)-2-chloropyrrolo[1,2-f][1,2,4]triazin-4-amine (200 mg, 0.7 mmol) and diisopropylethylamine (190, 1.4 mmol) in NMP (1 mL). The reaction mixture was heated at 130° C. for 72 hours and then diluted with ethyl acetate-water (20 mL, 4:1). The organic layer was separated and washed with water, dried (Na$_2$SO$_4$) and concentrated to afford the crude product. The crude product was dissolved in methanol and purified using preparative HPLC using the conditions shown below to afford 172 mg of N-(5-tert-butyl-1H-pyrazol-3-yl)-2-(2-(pyridin-2-yl)pyrrolidin-1-yl)pyrrolo[1,2-f][1,2,4]triazin-4-amine as the TFA salt.

Column: YMC ODS S5 35×100 mm
Gradient: 15-100% aqueous methanol over 12 minutes containing 0.1% TFA
Flow rate: 20 mL/min
Retention time: 10 min MS (ESI) m/z 403.3 (M+H). $^1$H NMR (CD$_3$OD) δ ppm 8.75 (d, J=5.4 Hz, 1H), 8.48 (dd, J=7.66, 2.2, 1H), 8.2 (d, J=8 Hz), 1H), 7.86 (dd, J=5.8, 1.9 Hz, 1H), 7.55 (s, 1H), 6.93 (d, J=4.8 Hz, 1H), 6.51 (d, J=4.8 Hz, 1H), 5.45 (m, 1H), 3.92 (m, 1H), 3.76 (m, 1H), 2.62 (m, 1H), 2.16 (m, 4H), 1.42 (s, 9H).

Example 116

N-Cyclopropyl-3-(7-phenyl-2-(2-(pyridin-2-yl)pyrrolidin-1-yl)pyrrolo[1,2-f][1,2,4]triazin-4-ylamino)-1H-pyrazole-5-carboxamide

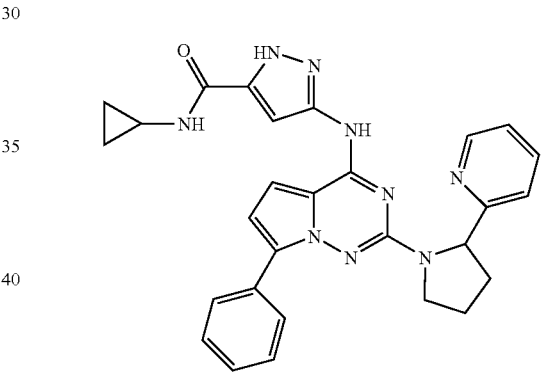

116A. Preparation of 7-bromo-2,4-dichloropyrrolo[1,2-f][1,2,4]triazine

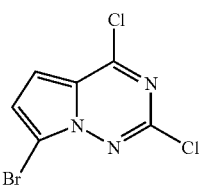

A slurry of N-bromosuccinimide (4.17 g, 23.40 mmol) in 10 mL of acetonitrile was added to a cooled (0° C.) solution of 2,4-dichloropyrrolo[1,2-f][1,2,4]triazine (4 g, 21.27 mmol) in acetonitrile over 1 h. The reaction mixture was allowed to come to room temperature and stirred for an additional 16 hr to get a solution. The solvents were evaporated to get a solid. To this residue was added dichloromethane to dissolve most of the solids and the resulting solution was loaded onto 250 gm of silica in a 350 mL coarse frit funnel (preequilibrated with 5% EtOAc in hexanes). The silica gel was washed with 5% to 50% EtOAC in hexanes. The fractions were collected and evaporated to obtain 7-bromo-2,4-dichloropyrrolo[1,2-f][1,2,4]triazine (5.29 g, 93% pure) as crystals contaminated with ~7% of the 5-bromo isomer. The mixture as such was carried to the next step without further purification. MS (ESI) m/z 266.08 (M+H).

116B. Preparation of 3-(7-bromo-2-chloropyrrolo[1,2-f][1,2,4]triazin-4-ylamino)-N-cyclopropyl-1H-pyrazole-5-carboxamide

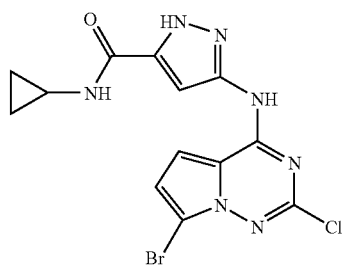

A mixture containing 7-bromo-2,4-dichloropyrrolo[1,2-f][1,2,4]triazine (1.379 g, 5.17 mmol), 3-amino-N-cyclopropyl-1H-pyrazole-5-carboxamide (1.03 g, 6.20 mmol), 2- and triethylamine (1.080 mL, 7.75 mmol) in 2-propanol (50 mL) was heated at 40° C. for 18 h. The reaction mixture was cooled to room temperature and evaporated to half of the solvent using a rotary evaporator. The mixture was diluted with equal amounts (~25 Ml) of water. The precipitate was filtered, washed with water (3×25 mL) and dried. 1.91 g of the dried powder was taken in 100 mL MeCN. The suspension was heated to ~70° C. on a hot water bath, cooled to RT and filtered to get 1.2 g of 3-(7-bromo-2-chloropyrrolo[1,2-f][1,2,4]triazin-4-ylamino)-N-cyclopropyl-1H-pyrazole-5-carboxamide. MS (ESI) m/z 396.1 (M+H). $^1$H NMR (500 MHz, Solvent) δ ppm 0.60 (s, 2H) 0.70 (s, 2H) 2.82 (s, 1H) 6.92 (s, 1H) 7.23 (s, 1H) 7.45 (s, 1H) 8.68 (s, 1H) 11.31 (s, 1H) 13.38 (s, 1H).

116C. Preparation of 3-(7-bromo-2-(2-(pyridin-2-yl)pyrrolidin-1-yl)pyrrolo[1,2-f][1,2,4]triazin-4-ylamino)-N-cyclopropyl-1H-pyrazole-5-carboxamide

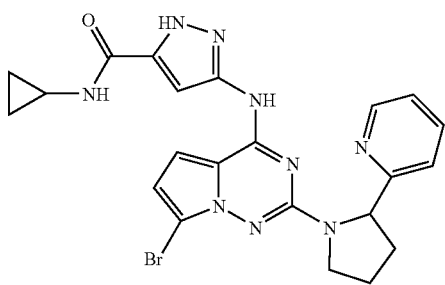

To a scintillation vial containing 3-(7-bromo-2-chloropyrrolo[1,2-f][1,2,4]triazin-4-ylamino)-N-cyclopropyl-1H-pyrazole-5-carboxamide (1.2 g, 3.03 mmol) was added 2-(pyrrolidin-2-yl)pyridine (0.897 g, 6.05 mmol) followed by Xylene (4 mL). The vial was heated at 120° C. for 67 h. The reaction mixture was cooled to room temperature and was diluted with n-hexane (2×30 mL). The resulting suspension was agitated and filtered through a medium frit funnel to get a residue. The residue was washed with ether (1×30 mL) and DCM (2×30 mL) to afford a powder and a filtrate. The filtrate was gradually evaporated to half its volume to get more ppt. This was filtered and combined with the original residue to get 3-(7-bromo-2-(2-(pyridin-2-yl)pyrrolidin-1-yl)pyrrolo[1,2-f][1,2,4]triazin-4-ylamino)-N-cyclopropyl-1H-pyrazole-5-carboxamide (1.38 g) as a powder. MS (ESI) m/z 508.27 (M+H). $^1$H NMR (500 MHz, Solvent) δ ppm 0.91 (dd, J=10.17, 4.12 Hz, 1H) 0.94-1.00 (m, 2H) 1.03 (dd, J=10.17, 4.12 Hz, 1H) 1.88-1.96 (m, 1H) 2.07-2.15 (m, 2H) 2.51 (td, J=8.66, 3.57 Hz, 1H) 3.15 (td, J=7.01, 3.57 Hz, 1H) 3.81-3.88 (m, 1H) 4.01-4.08 (m, 1H) 5.39 (s, 1H) 6.49 (d, J=4.95 Hz, 1H) 7.03-7.10 (m, 1H) 7.21 (d, J=8.25 Hz, 1H) 7.49 (s, 1H) 7.55 (t, J=7.42 Hz, 1H) 7.78 (d, J=4.95 Hz, 1H) 8.36 (d, J=2.20 Hz, 1H) 8.93 (s, 1H) 10.70 (s, 1H) 14.03 (s, 1H).

116D. Preparation of N-cyclopropyl-3-(7-phenyl-2-(2-(pyridin-2-yl)pyrrolidin-1-yl)pyrrolo[1,2-f][1,2,4]triazin-4-ylamino)-1H-pyrazole-5-carboxamide

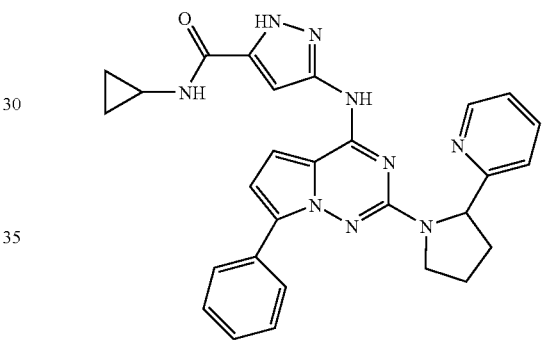

In a 10 mL CEM microwave vessel with stir bar was taken 3-(7-bromo-2-(2-(pyridin-2-yl)pyrrolidin-1-yl)pyrrolo[1,2-f][1,2,4]triazin-4-ylamino)-N-cyclopropyl-1H-pyrazole-5-carboxamide (Example 116C, 20 mg, 0.039 mmol) in THF (1 mL) and phenylboronic acid (19.19 mg, 0.157 mmol), Pd(Ph3P)$_4$ (9.09 mg, 7.87 μmol) and an aqueous solution of 3M potassium phosphate (0.079 mL, 0.236 mmol) were added. The reaction mixture was flushed with nitrogen and heated in the microwave at 150° C. for 10 min. The solvents were evaporated and the residue was dissolved in MeOH and purified by prep HPLC using the conditions as shown below to afford 6 mg of N-cyclopropyl-3-(7-phenyl-2-(2-(pyridin-2-yl)pyrrolidin-1-yl)pyrrolo[1,2-f][1,2,4]triazin-4-ylamino)-1H-pyrazole-5-carboxamide as the TFA salt Column: Luna 5u C18 250×21.2 mm
Gradient: 0-100% aqueous methanol over 26 minutes containing 0.1% TFA
Flow rate: 20 mL/min
Retention time: 24.1 min MS (ESI) m/z 506.4 (M+H). $^1$H NMR (500 MHz, CD$_3$OD) δ ppm 0.66-0.70 (m, 2H) 0.83-0.88 (m, 2H) 2.10-2.19 (m, 3H) 2.64-2.72 (m, 1H) 2.85-2.90 (m, 1H) 3.88-3.95 (m, 1H) 4.06 (d, J=3.85 Hz, 1H) 5.39 (dd, J=8.52, 3.02 Hz, 1H) 6.67 (s, 1H) 6.83 (d, J=4.95 Hz, 1H) 6.99 (d, J=4.95 Hz, 1H) 7.26 (t, J=7.15 Hz, 1H) 7.33 (t, J=7.42 Hz, 2H) 7.79 (s, 1H) 7.80-7.87 (m, 2H) 8.03 (d, J=8.25 Hz, 1H) 8.47 (t, J=7.97 Hz, 1H) 8.60 (d, J=5.50 Hz, 1H).

Examples 117 to 122

The following compounds in Table 5 have been synthesized using the procedure described in Example 116.

TABLE 5

| Ex. No. | R⁶ | Compound name | [M + H] | HPLC Ret Time (min) |
|---|---|---|---|---|
| 117 | 4-chlorophenyl | 3-(7-(4-chlorophenyl)-2-(2-(pyridin-2-yl)pyrrolidin-1-yl)pyrrolo[1,2-f][1,2,4]triazin-4-ylamino)-N-cyclopropyl-1H-pyrazole-5-carboxamide | 540.27 | 3.1 |
| 118 | 4-methoxyphenyl (OCH₃) | N-cyclopropyl-3-(7-(4-methoxyphenyl)-2-(2-(pyridin-2-yl)pyrrolidin-1-yl)pyrrolo[1,2-f][1,2,4]triazin-4-ylamino)-1H-pyrazole-5-carboxamide | 536.31 | 2.65 |
| 119 | o-tolyl | N-cyclopropyl-3-(2-(2-(pyridin-2-yl)pyrrolidin-1-yl)-7-o-tolylpyrrolo[1,2-f][1,2,4]triazin-4-ylamino)-1H-pyrazole-5-carboxamide | 520.3 | 2.85 |
| 120 | 3-acetamidophenyl | 3-(7-(3-acetamidophenyl)-2-(2-(pyridin-2-yl)pyrrolidin-1-yl)pyrrolo[1,2-f][1,2,4]triazin-4-ylamino)-N-cyclopropyl-1H-pyrazole-5-carboxamide | 563.4 | 2.09 |
| 121 | 2-methoxyphenyl (H₃CO) | N-cyclopropyl-3-(7-(2-methoxyphenyl)-2-(2-(pyridin-2-yl)pyrrolidin-1-yl)pyrrolo[1,2-f][1,2,4]triazin-4-ylamino)-1H-pyrazole-5-carboxamide | 536.4 | 2.64 |
| 122 | 4-methoxypyridin-3-yl (H₃CO) | N-cyclopropyl-3-(7-(4-methoxypyridin-3-yl)-2-(2-(pyridin-2-yl)pyrrolidin-1-yl)pyrrolo[1,2-f][1,2,4]triazin-4-ylamino)-1H-pyrazole-5-carboxamide | 537.28 | 1.97 |

Example 123

N-Cyclobutyl-3-(2-(2-(pyridin-2-yl)pyrrolidin-1-yl)pyrrolo[1,2-f][1,2,4]triazin-4-ylamino)-1H-pyrazole-5-carboxamide

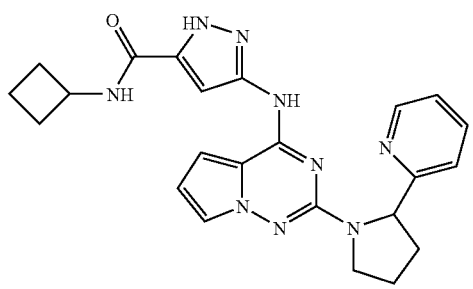

123A. Preparation of methyl 3-nitro-1H-pyrazole-5-carboxylate

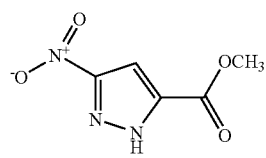

The compound was synthesized according to the procedure as reported (*Synthesis*, 12, 2003, p 1815).

123B. Preparation of methyl 3-amino-1H-pyrazole-5-carboxylate

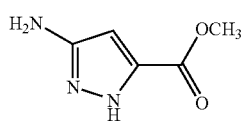

A suspension of methyl 3-nitro-1H-pyrazole-5-carboxylate (10 g, 58.4 mmol) and 10% Pd on charcoal (1.2 g) in methanol (150 Ml) was stirred under 50 psi pressure of hydrogen gas for 16 h. The reaction mixture was filtered over a bed of Celite and the filtrate was concentrated to give 9.2 g of methyl 3-amino-1H-pyrazole-5-carboxylate which was used as such in the next reaction. MS (ESI) m/z 142.3 (M+H).

123C. Preparation of methyl 3-(2-chloropyrrolo[1,2-f][1,2,4]triazin-4-ylamino)-1H-pyrazole-5-carboxylate

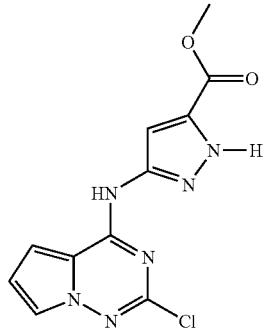

Methyl 5-amino-1H-pyrazole-3-carboxylate (2.8 g, 20.2 mmol) was added to the stirred suspension of 2,4-dichloropyrrolo[1,2-f][1,2,4]triazine (3.2 g, 17 mmol) in a mixture of 2-propanol and triethylamine (7 mL, 51 mmol). The reaction mixture was stirred at 45° C. for 16 hours. The reaction mixture was cooled at room temperature and concentrated in vacuo. The residue was suspended in water and the solid was filtered. The solid was washed with water and then dried under vacuum to furnish 4.4 g of methyl 3-(2-chloropyrrolo[1,2-f][1,2,4]triazin-4-ylamino)-1H-pyrazole-5-carboxylate. MS (ESI) m/z 293.5 (M+H).

123D. Preparation of sodium 3-(2-chloropyrrolo[1,2-f][1,2,4]triazin-4-ylamino)-1H-pyrazole-5-carboxylate

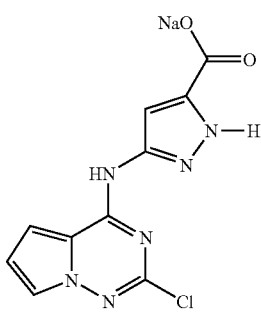

A mixture of methyl 3-(2-chloropyrrolo[1,2-f][1,2,4]triazin-4-ylamino)-1H-pyrazole-5-carboxylate (1.15 g, 3.93 mmol) and 1.0 N aqueous sodium hydroxide (3.93 mL, 3.93 mmol) in ethanol (4 mL) was stirred at 70° C. for 18 hr. The reaction mixture was concentrated under a stream of nitrogen to provide a syrup. 2-Propanol was added to the residue and the mixture was shaken vigorously and filtered. The solid was washed with 2-propanol (2×10 mL) and dried to furnish 1.06 g of sodium 3-(2-chloropyrrolo[1,2-f][1,2,4]triazin-4-ylamino)-1H-pyrazole-5-carboxylate as a solid. This was taken to the next step without further purification. MS (ESI) m/z 279.18 (M+H free acid).

123E. Preparation of 5-(2-(2-(pyridin-2-yl)pyrrolidin-1-yl)pyrrolo[1,2-f][1,2,4]triazin-4-ylamino)-1H-pyrazole-3-carboxylic acid

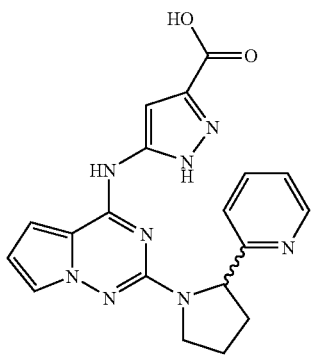

To a 20 mL scintillation vial containing sodium 3-(2-chloropyrrolo[1,2-f][1,2,4]triazin-4-ylamino)-1H-pyrazole-5-carboxylate (1.06 g, 3.53 mmol) was added 2-(pyrrolidin-2-yl)pyridine (1.045 g, 7.05 mmol) and xylene (4 mL) and the solution was heated at 125° C. for 72 hr. The reaction mixture was evaporated under a stream of nitrogen to get a solid. The solid was dissolved in 4 mL of DMF to get a solution. This solution was added dropwise into a rapidly stirring solution of acetic acid (0.606 mL, 10.58 mmol) in 12 mL ice cold water. The precipitate was filtered, washed with cold water (2×10 mL) and dried to give 910 mg of 5-(2-(2-(pyridin-2-yl)pyrrolidin-1-yl)pyrrolo[1,2-f][1,2,4]triazin-4-ylamino)-1H-pyrazole-3-carboxylic acid. MS (ESI) m/z 391.34 (M+H).

123F. Preparation of N-cyclobutyl-3-(2-(2-(pyridin-2-yl)pyrrolidin-1-yl)pyrrolo[1,2-f][1,2,4]triazin-4-ylamino)-1H-pyrazole-5-carboxamide hydrochloride

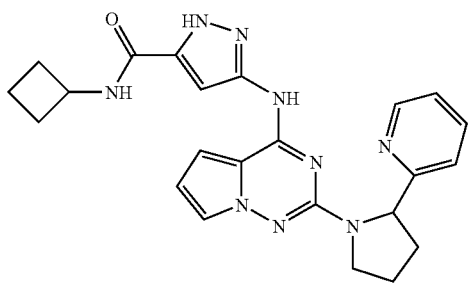

O-(7-azabenzotriazol-1-yl)-N,N,N',N'-tetramethyluronium PF6 (23.5 mg, 0.057 mmol) was added to a solution containing 5-(2-(2-(pyridin-2-yl)pyrrolidin-1-yl)pyrrolo[1,2-f][1,2,4]triazin-4-ylamino)-1H-pyrazole-3-carboxylic acid (20 mg, 0.051 mmol), cyclobutylamine (8 μL, 0.060 mmol) and Hunig base (16 μL, 0.12 mmol) in DMF (0.5 mL). The reaction mixture was stirred at room temperature for 16 hours. The reaction mixture was diluted with methanol and the mixture was purified using the conditions as below.

Column: YMC ODS S5 30×100 mm
Flow rate: 20 ml/min
Gradient: 20% B to 100% B over 12 minutes
Solvent A: 10% MeOH-90% water-0.1% TFA
Solvent B: 90% MeOH-10% water-0.1% TFA
Retention time: 6.3 minutes The fractions were combined and concentrated. The residue was taken up in methanol and was treated with a 4 N HCl solution in dioxane. The solution was concentrated in vacuo; re-constituted with methanol (2 mL) and concentrated to give 5.0 mg of N-cyclobutyl-3-(2-(2-(pyridin-2-yl)pyrrolidin-1-yl)pyrrolo[1,2-f][1,2,4]triazin-4-ylamino)-1H-pyrazole-5-carboxamide hydrochloride. MS (ESI) m/z 415 (M+H). $^1$H NMR (CD$_3$OD) δ ppm 8.46 (s, 1H), 7.63 (s, 1H), 7.26 (s, 2H), 7.12 (s, 1H), 6.71 (d, J=3.85 Hz, 1H), 6.37 (s, 1H), 5.20 (s, 1H), 3.80-3.86 (m, 1H), 3.64 (s, 1H), 2.75 (s, 1H), 2.42 (s, 1H), 1.96 (s, 3H), 0.74 (s, 2H), 0.58 (s, 2H).

Examples 124 to 167

The following compounds in Table 6 have been synthesized using the procedure described for in Example 123.

TABLE 6

| Ex. No. | R | Compound name | [M + H] | HPLC Ret Time (min) |
|---|---|---|---|---|
| 124 | -NH-CH2CH2-OH | N-(2-hydroxyethyl)-3-(2-(2-(pyridin-2-yl)pyrrolidin-1-yl)pyrrolo[1,2-f][1,2,4]triazin-4-ylamino)-1H-pyrazole-5-carboxamide | 434.03 | 1.65 |
| 125 | -NH-CH(Et)2 | N-(pentan-3-yl)-3-(2-(2-(pyridin-2-yl)pyrrolidin-1-yl)pyrrolo[1,2-f][1,2,4]triazin-4-ylamino)-1H-pyrazole-5-carboxamide | 460.11 | 2.46 |
| 126 | -N(Me)(propyl) | N-propyl-3-(2-(2-(pyridin-2-yl)pyrrolidin-1-yl)pyrrolo[1,2-f][1,2,4]triazin-4-ylamino)-1H-pyrazole-5-carboxamide | 446.09 | 2.07 |
| 127 | 4-hydroxypiperidin-1-yl | (4-hydroxypiperidin-1-yl)(3-(2-(2-(pyridin-2-yl)pyrrolidin-1-yl)pyrrolo[1,2-f][1,2,4]triazin-4-ylamino)-1H-pyrazol-5-yl)methanone | 474.06 | 1.55 |
| 128 | -NH-Ph | N-phenyl-3-(2-(2-(pyridin-2-yl)pyrrolidin-1-yl)pyrrolo[1,2-f][1,2,4]triazin-4-ylamino)-1H-pyrazole-5-carboxamide | 466.26 | 2.51 |
| 129 | -NH-C6H4-CONH2 | N-(4-carbamoylphenyl)-3-(2-(2-(pyridin-2-yl)pyrrolidin-1-yl)pyrrolo[1,2-f][1,2,4]triazin-4-ylamino)-1H-pyrazole-5-carboxamide | 509.25 | 1.89 |
| 130 | -NH-C6H4-iPr | N-(4-isopropylphenyl)-3-(2-(2-(pyridin-2-yl)pyrrolidin-1-yl)pyrrolo[1,2-f][1,2,4]triazin-4-ylamino)-1H-pyrazole-5-carboxamide | 508.28 | 3.04 |
| 131 | -NH-CH2-Ph | N-benzyl-3-(2-(2-(pyridin-2-yl)pyrrolidin-1-yl)pyrrolo[1,2-f][1,2,4]triazin-4-ylamino)-1H-pyrazole-5-carboxamide | 480.27 | 2.34 |
| 132 | -NH-iBu | N-isobutyl-3-(2-(2-(pyridin-2-yl)pyrrolidin-1-yl)pyrrolo[1,2-f][1,2,4]triazin-4-ylamino)-1H-pyrazole-5-carboxamide | 446.3 | 2.3 |

TABLE 6-continued

| Ex. No. | R | Compound name | [M + H] | HPLC Ret Time (min) |
|---|---|---|---|---|
| 133 | —NH—CH2-cyclopropyl | N-(cyclopropylmethyl)-3-(2-(2-(pyridin-2-yl)pyrrolidin-1-yl)pyrrolo[1,2-f][1,2,4]triazin-4-ylamino)-1H-pyrazole-5-carboxamide | 444.27 | 2.17 |
| 134 | HN-cyclopentyl | N-cyclopentyl-3-(2-(2-(pyridin-2-yl)pyrrolidin-1-yl)pyrrolo[1,2-f][1,2,4]triazin-4-ylamino)-1H-pyrazole-5-carboxamide | 458.28 | 2.32 |
| 135 | HN-tert-butyl | N-tert-butyl-3-(2-(2-(pyridin-2-yl)pyrrolidin-1-yl)pyrrolo[1,2-f][1,2,4]triazin-4-ylamino)-1H-pyrazole-5-carboxamide | 446.28 | 2.37 |
| 136 | HN-sec-butyl | N-sec-butyl-3-(2-(2-(pyridin-2-yl)pyrrolidin-1-yl)pyrrolo[1,2-f][1,2,4]triazin-4-ylamino)-1H-pyrazole-5-carboxamide | 446.25 | 2.22 |
| 137 | 4-(hydroxymethyl)piperidin-1-yl | (4-(hydroxymethyl)piperidin-1-yl)(3-(2-(2-(pyridin-2-yl)pyrrolidin-1-yl)pyrrolo[1,2-f][1,2,4]triazin-4-ylamino)-1H-pyrazol-5-yl)methanone | 488.27 | 1.64 |
| 138 | piperidin-1-yl | piperidin-1-yl(3-(2-(2-(pyridin-2-yl)pyrrolidin-1-yl)pyrrolo[1,2-f][1,2,4]triazin-4-ylamino)-1H-pyrazol-5-yl)methanone | 458.27 | 2.04 |
| 139 | N,N-diethyl | N,N-diethyl-3-(2-(2-(pyridin-2-yl)pyrrolidin-1-yl)pyrrolo[1,2-f][1,2,4]triazin-4-ylamino)-1H-pyrazole-5-carboxamide | 446.27 | 2.07 |
| 140 | pyrrolidin-1-yl | (3-(2-(2-(pyridin-2-yl)pyrrolidin-1-yl)pyrrolo[1,2-f][1,2,4]triazin-4-ylamino)-1H-pyrazol-5-yl)(pyrrolidin-1-yl)methanone | 444.27 | 1.93 |
| 141 | N-isopropyl-N-methyl | N-isopropyl-N-methyl-3-(2-(2-(pyridin-2-yl)pyrrolidin-1-yl)pyrrolo[1,2-f][1,2,4]triazin-4-ylamino)-1H-pyrazole-5-carboxamide | 446.26 | 2.00 |
| 142 | azetidin-1-yl | azetidin-1-yl(3-(2-(2-(pyridin-2-yl)pyrrolidin-1-yl)pyrrolo[1,2-f][1,2,4]triazin-4-ylamino)-1H-pyrazol-5-yl)methanone | 430.25 | 1.84 |

TABLE 6-continued

| Ex. No. | R | Compound name | [M + H] | HPLC Ret Time (min) |
|---|---|---|---|---|
| 143 | (R)-3-hydroxypyrrolidin-1-yl, N-linked | ((R)-3-hydroxypyrrolidin-1-yl)(3-(2-(2-(pyridin-2-yl)pyrrolidin-1-yl)pyrrolo[1,2-f][1,2,4]triazin-4-ylamino)-1H-pyrazol-5-yl)methanone | 460.27 | 1.59 |
| 144 | HN-CH(CH2OH)- (R) | N-((R)-1-hydroxypropan-2-yl)-3-(2-(2-(pyridin-2-yl)pyrrolidin-1-yl)pyrrolo[1,2-f][1,2,4]triazin-4-ylamino)-1H-pyrazole-5-carboxamide | 448.26 | 1.72 |
| 145 | HN-CH2-CH(OH)-CH2OH (R) | N-((R)-2,3-dihydroxypropyl)-3-(2-(2-(pyridin-2-yl)pyrrolidin-1-yl)pyrrolo[1,2-f][1,2,4]triazin-4-ylamino)-1H-pyrazole-5-carboxamide | 464.23 | 1.56 |
| 146 | HN-CH2-CH(OH)-CH2OH (S) | N-((S)-2,3-dihydroxypropyl)-3-(2-(2-(pyridin-2-yl)pyrrolidin-1-yl)pyrrolo[1,2-f][1,2,4]triazin-4-ylamino)-1H-pyrazole-5-carboxamide | 464.23 | 1.54 |
| 147 | 3-hydroxyazetidin-1-yl | (3-hydroxyazetidin-1-yl)(3-(2-(2-(pyridin-2-yl)pyrrolidin-1-yl)pyrrolo[1,2-f][1,2,4]triazin-4-ylamino)-1H-pyrazol-5-yl)methanone | 446.21 | 1.61 |
| 148 | HN-CH2-CH(OH)-CH3 (R) | N-((R)-2-hydroxypropyl)-3-(2-(2-(pyridin-2-yl)pyrrolidin-1-yl)pyrrolo[1,2-f][1,2,4]triazin-4-ylamino)-1H-pyrazole-5-carboxamide | 448.26 | 1.66 |
| 149 | HN-CH(CH2OH)- (S) | N-((S)-1-hydroxypropan-2-yl)-3-(2-(2-(pyridin-2-yl)pyrrolidin-1-yl)pyrrolo[1,2-f][1,2,4]triazin-4-ylamino)-1H-pyrazole-5-carboxamide | 448.22 | 1.72 |
| 150 | HN-CH2CH2-OCH3 | N-(2-methoxyethyl)-3-(2-(2-(pyridin-2-yl)pyrrolidin-1-yl)pyrrolo[1,2-f][1,2,4]triazin-4-ylamino)-1H-pyrazole-5-carboxamide | 448.21 | 1.85 |
| 151 | HN-iPr | N-isopropyl-3-(2-(2-(pyridin-2-yl)pyrrolidin-1-yl)pyrrolo[1,2-f][1,2,4]triazin-4-ylamino)-1H-pyrazole-5-carboxamide | 432.21 | 2.09 |
| 152 | HN-CH2-CH(OH)-CH3 (S) | N-((S)-2-hydroxypropyl)-3-(2-(2-(pyridin-2-yl)pyrrolidin-1-yl)pyrrolo[1,2-f][1,2,4]triazin-4-ylamino)-1H-pyrazole-5-carboxamide | 448.21 | 1.68 |

TABLE 6-continued

| Ex. No. | R | Compound name | [M + H] | HPLC Ret Time (min) |
|---|---|---|---|---|
| 153 | (3-methoxyphenyl)NH- | N-(3-methoxyphenyl)-3-(2-(2-(pyridin-2-yl)pyrrolidin-1-yl)pyrrolo[1,2-f][1,2,4]triazin-4-ylamino)-1H-pyrazole-5-carboxamide | 496.25 | 2.65 |
| 154 | (4-chlorophenyl)NH- | N-(4-chlorophenyl)-3-(2-(2-(pyridin-2-yl)pyrrolidin-1-yl)pyrrolo[1,2-f][1,2,4]triazin-4-ylamino)-1H-pyrazole-5-carboxamide | 500.22 | 2.82 |
| 155 | (4-methoxyphenyl)NH- | N-(4-methoxyphenyl)-3-(2-(2-(pyridin-2-yl)pyrrolidin-1-yl)pyrrolo[1,2-f][1,2,4]triazin-4-ylamino)-1H-pyrazole-5-carboxamide | 496.22 | 2.49 |
| 156 | (3-carbamoylphenyl)NH- | N-(3-carbamoylphenyl)-3-(2-(2-(pyridin-2-yl)pyrrolidin-1-yl)pyrrolo[1,2-f][1,2,4]triazin-4-ylamino)-1H-pyrazole-5-carboxamide | 509.26 | 1.91 |
| 157 | (4-acetamidophenyl)NH- | N-(4-acetamidophenyl)-3-(2-(2-(pyridin-2-yl)pyrrolidin-1-yl)pyrrolo[1,2-f][1,2,4]triazin-4-ylamino)-1H-pyrazole-5-carboxamide | 523.26 | 1.98 |
| 158 | (2-methoxyphenyl)NH- | N-(2-methoxyphenyl)-3-(2-(2-(pyridin-2-yl)pyrrolidin-1-yl)pyrrolo[1,2-f][1,2,4]triazin-4-ylamino)-1H-pyrazole-5-carboxamide | 496.24 | 2.64 |
| 159 | -NHCH$_2$CO$_2$CH$_3$ | methyl 2-(3-(2-(2-(pyridin-2-yl)pyrrolidin-1-yl)pyrrolo[1,2-f][1,2,4]triazin-4-ylamino)-1H-pyrazole-5-carboxamido)acetate | 462.21 | 1.89 |
| 160 | (4-hydroxycyclohexyl)NH- | N-(4-hydroxycyclohexyl)-3-(2-(2-(pyridin-2-yl)pyrrolidin-1-yl)pyrrolo[1,2-f][1,2,4]triazin-4-ylamino)-1H-pyrazole-5-carboxamide | 488.27 | 1.77 |

TABLE 6-continued

| Ex. No. | R | Compound name | [M + H] | HPLC Ret Time (min) |
|---|---|---|---|---|
| 161 | (tetrahydrofuran-2-yl)methylamino | 3-(2-(2-(pyridin-2-yl)pyrrolidin-1-yl)pyrrolo[1,2-f][1,2,4]triazin-4-ylamino)-N-((tetrahydrofuran-2-yl)methyl)-1H-pyrazole-5-carboxamide | 474.27 | 1.95 |
| 162 | HN-CH2CH2-CO2CH3 | methyl 3-(3-(2-(2-(pyridin-2-yl)pyrrolidin-1-yl)pyrrolo[1,2-f][1,2,4]triazin-4-ylamino)-1H-pyrazole-5-carboxamido)propanoate | 476.25 | 1.92 |
| 163 | tetrahydro-2H-pyran-4-ylamino | 3-(2-(2-(pyridin-2-yl)pyrrolidin-1-yl)pyrrolo[1,2-f][1,2,4]triazin-4-ylamino)-N-(tetrahydro-2H-pyran-4-yl)-1H-pyrazole-5-carboxamide | 474.25 | 1.85 |
| 164 | HN-CH2CH2-OCH3 | N-(3-methoxypropyl)-3-(2-(2-(pyridin-2-yl)pyrrolidin-1-yl)pyrrolo[1,2-f][1,2,4]triazin-4-ylamino)-1H-pyrazole-5-carboxamide | 462.25 | 1.93 |
| 165 | (1R,2R)-2-hydroxycyclopentylamino | N-((1R,2R)-2-hydroxycyclopentyl)-3-(2-(2-(pyridin-2-yl)pyrrolidin-1-yl)pyrrolo[1,2-f][1,2,4]triazin-4-ylamino)-1H-pyrazole-5-carboxamide | 474.25 | 1.88 |
| 166 | 2-hydroxy-2-phenylethylamino | N-(2-hydroxy-2-phenylethyl)-3-(2-(2-(pyridin-2-yl)pyrrolidin-1-yl)pyrrolo[1,2-f][1,2,4]triazin-4-ylamino)-1H-pyrazole-5-carboxamide | 510.26 | 2.08 |
| 167 | pyridin-4-ylamino | 3-(2-(2-(pyridin-2-yl)pyrrolidin-1-yl)pyrrolo[1,2-f][1,2,4]triazin-4-ylamino)-N-(pyridin-4-yl)-1H-pyrazole-5-carboxamide | 467.21 | 2.01 |

Example 168

(S)-N-Cyclopropyl-3-(2-(2-(pyrimidin-2-yl)pyrrolidin-1-yl)pyrrolo[1,2-f][1,2,4]triazin-4-ylamino)-1H-pyrazole-5-carboxamide

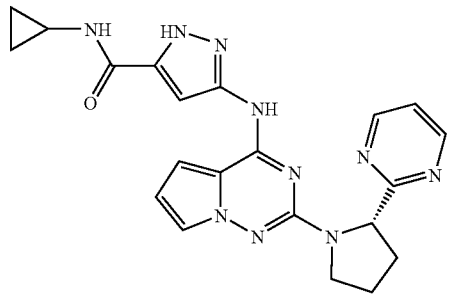

168A. Preparation of (S)-2-(pyrrolidin-2-yl)pyrimidine

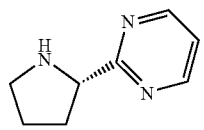

The compound was prepared according to the procedure reported in WO 02/060894 (example INT62).

168B. Preparation of (S)-N-cyclopropyl-3-(2-(2-(pyrimidin-2-yl)pyrrolidin-1-yl)pyrrolo[1,2-f][1,2,4]triazin-4-ylamino)-1H-pyrazole-5-carboxamide A mixture of 3-(2-chloropyrrolo[1,2-f][1,2,4]triazin-4-ylamino)-N-cyclopropyl-1H-pyrazole-5-carboxamide (60 mg, 0.189 mmol, example 100C), (S)-2-(pyrrolidin-2-yl)pyrimidine (42.3 mg, 0.283 mmol) and Hunig base (0.132 ml, 0.755 mmol) in N-methyl-2-pyrrolidinone (2 ml) was heated at 180° C. for 8 h. The reaction mixture was diluted with methanol/water and purified by prep-HPLC (Rt 10.91 min, Waters Sunflower C-18 column 19×100 mm, 30-80% aqueous methanol over 10 minutes containing 0.1% TFA, 20 mL/min, monitoring at 254 nm). The resulting product still contained about 10% impurities and was further purified by prep-TLC, eluting with 7% 2N ammonia/methanol/dichloromethane to give 6.0 mg of (S)—N-cyclopropyl-3-(2-(2-(pyrimidin-2-yl)pyrrolidin-1-yl)pyrrolo[1,2-f][1,2,4]triazin-4-ylamino)-1H-pyrazole-5-carboxamide as a solid. MS (ESI) m/z 430 (M+H). $^1$H NMR (500 MHz, mixed solvent of CDCl$_3$ and methanol-d$_4$) δ ppm 8.75 (d, J=4.95 Hz, 2H), 7.35 (s, 1H), 7.24 (t, J=4.81 Hz, 1H), 6.81 (d, J=3.30 Hz, 1H), 6.42-6.44 (m, 1H), 6.36 (s, 1H), 5.41-5.44 (m, 1H), 3.83-3.88 (m, 1H), 3.68-m 3.75 (m, 1H), 2.80-2.87 (m, 1H), 2.50-2.57 (m, 1H), 2.42-2.47 (m, 1H), 2.14-2.23 (m, 1H), 2.07-2.14 (m, 1H), 0.80-0.87 (m, 2H), 0.63-0.71 (m, 2H).

Example 169

Ethyl 4-(5-(cyclopropylcarbamoyl)-1H-pyrazol-3-ylamino)-2-(2-(pyridine-2-yl)pyrrolidin-1-yl)pyrrolo[1,2-f][1,2,4]triazine-7-carboxylate

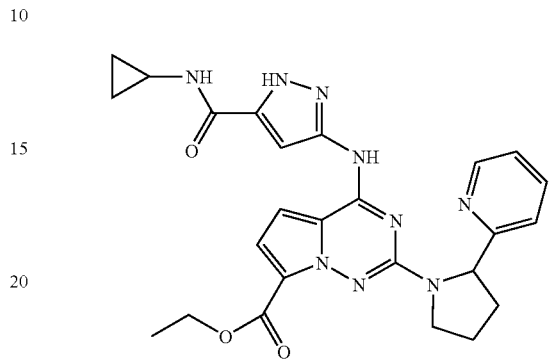

A steel autoclave charged with 3-(7-bromo-2-(2-(pyridin-2-yl)pyrrolidin-1-yl)pyrrolo[1,2-f][1,2,4]triazin-4-ylamino)-N-cyclopropyl-1H-pyrazole-5-carboxamide (100 mg, 0.197 mmol, example 116C), palladium(II) acetate (0.221 mg, 0.984 μmol), DPPF (8.18 mg, 0.015 mmol), triethylamine (0.082 ml, 0.590 mmol) and ethanol (15 ml) was pressurized with 80 psi of carbon monoxide gas. The reaction mixture was then heated at 100° C. for 6 h and cooled to room temperature. The solvent was evaporated and the residue was purified by flash chromatography on silica gel using an automated ISCO system (40 g column, eluting with 0-10% 2N ammonia in methanol/dichloromethane, Flow rate: 40 mL/min) to give ethyl 4-(5-(cyclopropylcarbamoyl)-1H-pyrazol-3-ylamino)-2-(2-(pyridin-2-yl)pyrrolidin-1-yl)pyrrolo[1,2-f][1,2,4]triazine-7-carboxylate (109 mg, 0.217 mmol, 110% yield) as a solid. 30 mg of the compound was purified by prep-HPLC (Rt 7.63 min, Waters Sunflower C-18 column 19×100 mm, 30-80% aqueous methanol over 10 minutes containing 0.1% TFA, 20 mL/min, monitoring at 254 nm), however $^1$H NMR and HPLC showed a impurity accounted for about 15%. The compound was further purified by prep-HPLC (Rt. 11.10 min, Phenomenex Luna C8(2), 3 μm, 4.6×150 mm column, column temperature 30° C., 20-95% acetonitrile/water containing 0.05% TFA over 30 minutes, 1 mL/min, monitoring at 254 nm) and 6.6 mg of Ethyl 4-(5-(cyclopropylcarbamoyl)-1H-pyrazol-3-ylamino)-2-(2-(pyridine-2-yl)pyrrolidin-1-yl)pyrrolo[1,2-f][1,2,4]triazine-7-carboxylate was obtained. MS (ESI) m/z 502 (M+H). $^1$H NMR (500 MHz, methanol-d$_4$) δ ppm 8.71 (d, J=5.50 Hz, 1H), 8.50 (t, J=7.70 Hz, 1H), 8.07 (d, J=7.97 Hz, 1H), 8.50 (t, J=6.60 Hz, 1H), 7.14 (, J=4.95 Hz, 1H), 6.92 (d, J=4.60 Hz, 1H), 6.83 (br. s, 1H), 5.39 (dd, J=8.52, 3.57 Hz, 1H), 4.37 (q, J=7.15 Hz, 2H), 3.95-4.02 (m, 1H), 3.84-3.91 (m, 1H), 2.82-2.87 (m, 1H), 2.58-2.66 (m, 1H), 2.33-2.41 (m, 1H), 2.19-2.28 (m, 2H), 1.93 (s, 4H), 1.38 (t, J=7.15 Hz, 2H), 0.79-0.87 (m, 2H), 0.63-0.70 (m, 2H).

Example 170

(3S,4R)-1-(4-(5-Methyl-1H-pyrazol-3-ylamino)pyrrolo[1,2-f][1,2,4]triazin-2-yl)-4-phenylpyrrolidin-3-ol

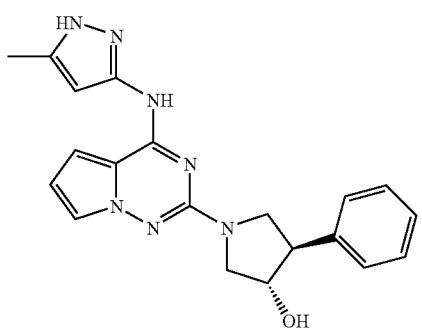

170A. Preparation of (3S,4R)-4-phenylpyrrolidin-3-ol

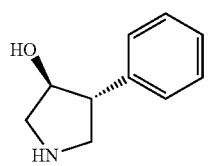

The compound was prepared using the procedure as reported in WO 2005/032464 (example 1, step A).

170B. Preparation of (3S,4R)-1-(4-(5-methyl-1H-pyrazol-3-ylamino)pyrrolo[1,2-f][1,2,4]triazin-2-yl)-4-phenylpyrrolidin-3-ol A mixture of 2-chloro-N-(5-methyl-1H-pyrazol-3-yl)pyrrolo[1,2-f][1,2,4]triazin-4-amine (34 mg, 0.137 mmol, example 113A), (3S,4R)-4-phenylpyrrolidin-3-ol (44.6 mg, 0.273 mmol) and DIEA (0.096 mL, 0.547 mmol) in N-methyl-2-pyrrolidinone (1 mL) was heated at 140° C. overnight. LC/MS showed about 60% completion. The reaction mixture was diluted with methanol/water and purified by prep-HPLC (Phenomenex Luna 5u 21×250 mm column, Rt 21.5 min, 10-100% aqueous methanol over 25 minutes containing 0.1% TFA, 20 mL/min, monitoring at 254 nm). The resulting TFA salt was converted to the free base by a SCX column. (3S,4R)-1-(4-(5-methyl-1H-pyrazol-3-ylamino)pyrrolo[1,2-f][1,2,4]triazin-2-yl)-4-phenylpyrrolidin-3-ol (7.6 mg, 0.020 mmol, 14.81% yield) was obtained as a solid. MS (ESI) m/z 376 (M+H). $^1$H NMR (500 MHz, methanol-d4) δ ppm 7.61 (dd, J=2.47, 1.65 Hz, 1 H), 7.36 (s, 2H), 7.35 (s, 2 H), 7.25-7.30 (m, 1 H), 7.20 (dd, J=4.81, 1.51 Hz, 1 H), 6.67 (dd, J=4.95, 2.47 Hz, 1 H), 6.21 (s, 1 H), 4.49 (q, J=6.05 Hz, 1 H), 4.12 (dd, J=10.04, 7.84 Hz, 1 H), 3.96 (dd, J=10.58, 6.19 Hz, 1 H), 3.78 (dd, J=10.04, 7.29 Hz, 1 H), 3.52 (dd, J=10.58, 5.36 Hz, 1 H), 3.46 (q, J=7.33 Hz, 1 H), 2.32 (s, 3 H).

Example 171

N-(3-Ethyl-1H-pyrazol-5-yl)-2-(3-(2-fluorophenyl)pyrrolidin-1-yl)pyrrolo[1,2-f][1,2,4]triazin-4-amine

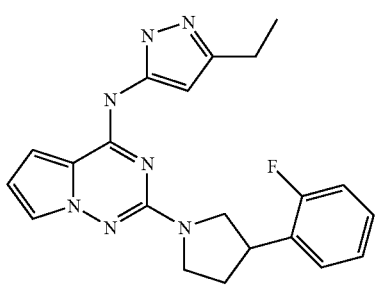

A solution of 1A (10 mg, 0.038 mmol) in N-methylpyrrolidone (NMP, 1 mL) was treated with 3-(2-fluorophenyl)pyrrolidine hydrochloride (35 mg, 0.174 mmol) and N,N-diisopropylethylamine (0.1 mL, 0.574 mmol) in a microwave vial (CEM Corporation, 10 mL). The mixture was heated at 120° C. for 30 minutes using 300 W continuous power. The reaction mixture was then diluted with methanol (1 mL) and purified by preparative reversed-phase HPLC (YMC ODS-A 20×100 mm, 10-90% aqueous methanol containing 0.1% TFA, 20 min gradient, monitored at 220 nm) to give the title compound (7.8 mg, 53%). $^1$HNMR (DMSO-d$_6$) δ 10.32 (s, 1H), 7.41 (s, 2H), 7.31 (m, 1H), 7.20 (m, 2H), 7.18 (m, 1H), 6.67 (s, 1H), 6.40 (m, 1H), 3.98 (m, 1H), 3.71 (m, 2 H), 3.58 (m, 1 H), 3.49 (m, 1 H), 2.59 (q, J=7.55 Hz, 2 H), 2.35 (s, 1 H), 2.11 (dd, J=11.96, 8.69 Hz, 1 H), 1.18 (t, J=7.55 Hz, 3 H), HPLC t$_R$=4.135 min. (YMC S5 Combiscreen ODS 4.6×50 mm, 10-90% aqueous methanol containing 0.2% H$_3$PO$_4$, 4 min gradient, monitored at 220 or 254 nm). m/z=392.4 (M+H).

Examples 172 to 200

The following examples in Table 7 have been synthesized utilizing the general procedure described in Example 171 and the given reaction times and temperatures. Starting materials were obtained as described in Example 1 from 2,4-dichloropyrrolo[1,2-f][1,2,4]triazine and the appropriate pyrazole (commercially available or from Table 1).

TABLE 7

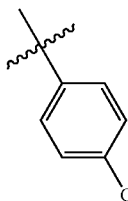

| Ex No. | R[1] | R[2] | Reaction Temp/Time (°C./minutes) | Compound Name | [M + H] | HPLC Ret Time (min)[a] |
|---|---|---|---|---|---|---|
| 172 | Me | 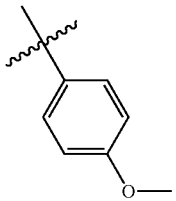 | 100/10 | 2-(3-(4-chlorophenyl) pyrrolidin-1-yl)-N-(3-methyl-1H-pyrazol-5-yl) pyrrolo[1,2-f][1,2,4] triazin-4-amine | 387.37 | 2.60 |
| 173 | Me | 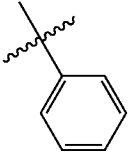 | 100/40 | 2-(3-(4-methoxyphenyl) pyrrolidin-1-yl)-N-(3-methyl-1H-pyrazol-5-yl)pyrrolo[1,2-f][1,2,4] triazin-4-amine | 390.3 | 3.80 |
| 174 | 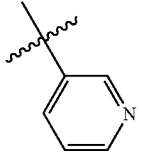 | 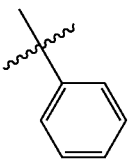 | 100/40 | N-(3-phenyl-1H-pyrazol-5-yl)-2-(3-(pyridin-3-yl) pyrrolidin-1-yl)pyrrolo[1,2-f][1,2,4]triazin-4-amine | 423.36 | 3.170 |
| 175 | 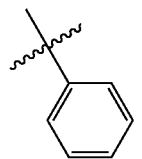 | 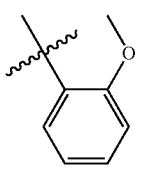 | 100/50 | N-(3-phenyl-1H-pyrazol-5-yl)-2-(3-phenylpyrrolidin-1-yl)pyrrolo[1,2-f][1,24] triazin-4-amine | 422.47 | 4.448 |
| 176 | Me | 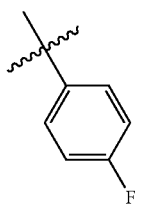 | 100/40 | 2-(3-(2-methoxyphenyl) pyrrolidin-1-yl)-N-(3-methyl-1H-pyrazol-5-yl) pylTolo[1,2-f][1,2,4] triazin-4-amine | 386.3 | 4.031 |
| 177 | Me |  | 100/10 | 2-(3-(4-fluorophenyl) pyrrolidin-1-yl)-N-(3-methyl-1H-pyrazol-5-yl) pyrrolo[1,2-f][1,2,4] triazin-4-amine | 378.42 | 3.940 |

TABLE 7-continued

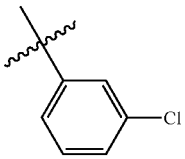

| Ex No. | R¹ | R² | Reaction Temp/Time (°C./minutes) | Compound Name | [M + H] | HPLC Ret Time (min)$^a$ |
|---|---|---|---|---|---|---|
| 178 | Me | 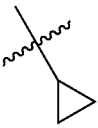 | 100/10 | 2-(3-(3-chlorophenyl) pyrrolidin-1-yl)-N-(3-methyl-1H-pyrazol-5-yl) pyrrolo[1,2-f][1,2,4] triazin-4-amine | 394.37 | 4.146 |
| 179 | 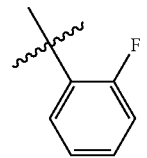 | 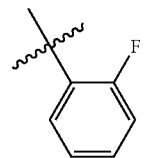 | 100/10 | N-(3-cyclopropyl-1H-pyrazol-5-yl)-2-(3-(2-fluorophenyl)pyrrolidin-1-yl)pyrrolo[1,2-f][1,2,4] triazin-4-amine | 404.44 | 4.17 |
| 180 | Me | 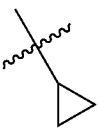 | 100/10 | 2-(3-(2-fluorophenyl) pyrrolidin-1-yl)-N-(3-methyl-1H-pyrazol-5-yl) pyrrolo[1,2-f][1,2,4]triazin-4-amine | 378.44 | 3.98 |
| 181 | 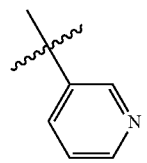 | 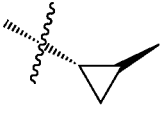 | 100/40 | N-(3-cyclopropyl-1H-pyrazol-5-yl)-2-(3-(pyridin-3-yl)pyrrolidin-1-yl)pyrrolo[1,2-f][1,2,4]triazin-4-amine | 387.37 | 2.600 |
| 182 | 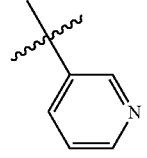 | 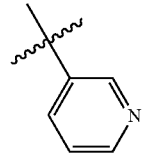 | 130/90 | N-(3-((1S,2S)-2-methylcyclopropyl)-1H-pyrazol-5-yl)-2-(3-(pyridin-3-yl)pyrrolidin-1-yl)pyrrolo[1,2-f][1,2,4]triazin-4-amine | 401.3 | 2.870 |
| 183 | Et | 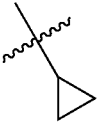 | 120/30 | N-(3-ethyl-1H-pyrazol-5-yl)-2-(3-(pyridin-3-yl) pyrrolidin-1-yl)pyrrolo[1,2-f][1,2,4]triazin-4-amine | 375.3 | 2.508 |
| 184 | 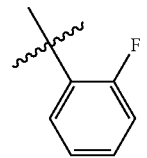 | 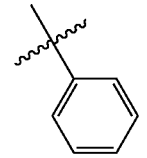 | 120/30 | N-(3-cyclopropyl-1H-pyrazol-5-yl)-2-(3-phenylpyrrolidin-1-yl) pyrrolo[1,2-f][1,2,4]triazin-4-amine | 386.3 | 4.031 |

TABLE 7-continued

| Ex No. | R¹ | R² | Reaction Temp/Time (°C./minutes) | Compound Name | [M + H] | HPLC Ret Time (min)[a] |
|---|---|---|---|---|---|---|
| 185 | Et | phenyl | 120/30 | N-(3-ethyl-1H-pyrazol-5-yl)-2-(3-phenylpyrrolidin-1-yl)pyrrolo[1,2-f][1,2,4]triazin-4-amine | 374.4 | 4.073 |
| 186 | Me | phenyl | 100/30 | N-(5-methyl-1H-pyrazol-3-yl)-2-(3-phenylpyrrolidin-1-yl)pyrrolo[1,2-f][1,2,4]triazin-4-amine | 360.4 | 3.806 |
| 187 | CH₂Ph | pyridin-3-yl | 110/90 | N-(3-benzyl-1H-pyrazol-5-yl)-2-(3-(pyridin-3-yl)pyrrolidin-1-yl)pyrrolo[1,2-f][1,2,4]triazin-4-amine | 437.3 | 3.053 |
| 188 | cyclobutyl | pyridin-3-yl | 130/90 | N-(3-cyclobutyl-1H-pyrazol-5-yl)-2-(3-(pyridin-3-yl)pyrrolidin-1-yl)pyrrolo[1,2-f][1,2,4]triazin-4-amine | 401.3 | 2.851 |
| 189 | Me | pyridin-3-yl | 100/70 | N-(5-methyl-1H-pyrazol-3-yl)-2-(3-(pyridin-3-yl)pyrrolidin-1-yl)pyrrolo[1,2-f][1,2,4]triazin-4-amine | 361.3 | 2.282 |
| 190 | isopropyl | pyridin-3-yl | 130/90 | N-(3-isopropyl-1H-pyrazol-5-yl)-2-(3-(pyridin-3-yl)pyrrolidin-1-yl)pyrrolo[1,2-f][1,2,4]triazin-4-amine | 389.3 | 2.710 |
| 191 | 1-methylcyclopropyl | pyridin-3-yl | 120/30 | 2-(4-amino-1-piperidinyl)-N-(3-isopropyl-1H-pyrazol-5-yl)pyrrolo[2,1-f][1,2,4]triazin-4-amine | 401.3 | 2.845 |

TABLE 7-continued

| Ex No. | R¹ | R² | Reaction Temp/Time (°C./minutes) | Compound Name | [M + H] | HPLC Ret Time (min)ᵃ |
|---|---|---|---|---|---|---|
| 192 | Me | 3-methoxyphenyl | 120/30 | 2-(3-(3-methoxyphenyl) pyrrolidin-1-yl)-N-(3-methyl-1H-pyrazol-5-yl) pyrrolo[1,2-f][1,2,4]triazin-4-amine | 390.37 | 3.840 |
| 193 | sec-butyl | pyridin-3-yl | 130/90 | N-(3-sec-butyl-1H-pyrazol-5-yl)-2-(3-(pyridin-3-yl) pyrrolidin-1-yl)pyrrolo[1,2-f][1,2,4]triazin-4-amine | 403.3 | 2.921 |
| 194 | isobutyl | pyridin-3-yl | 130/90 | N-(3-isobutyl-1H-pyrazol-5-yl)-2-(3-(pyridin-3-yl) pyrrolidin-1-yl)pyrrolo[1,2-f][1,2,4]triazin-4-amine | 403.3 | 2.955 |
| 195 | H | pyridin-3-yl | 130/90 | N-(1H-pyrazol-5-yl)-2-(3-(pyridin-3-yl)pyrrolidin-1-yl)pyrrolo[1,2-f][1,2,4]triazin-4-amine | 347.4 | 2.200 |
| 196 | Me | pyridin-2-yl | 220/180 | N-(5-methyl-1H-pyrazol-3-yl)-2-(3-(pyridin-2-yl) pyrrolidin-1-yl)pyrrolo[1,2-f][1,2,4]triazin-4-amine | 361.2 | 2.463 |
| 197 | (1S,2S)-2-phenylcyclopropyl | pyridin-3-yl | 130/90 | N-(3-((1S,2S)-2-phenylcyclopropyl)-1H-pyrazol-5-yl)-2-(3-(pyridin-3-yl)pyrrolidin-1-yl)pyrrolo[1,2-f][1,2,4]triazin-4-amine | 463.3 | 3.405 |
| 198 | tert-butyl | pyridin-3-yl | 120/30 | N-(3-tert-butyl-1H-pyrazol-5-yl)-2-(3-(pyridin-3-yl) pyrrolidin-1-yl)pyrrolo[1,2-f][1,2,4]triazin-4-amine | 403.3 | 2.891 |

TABLE 7-continued

| Ex. No. | R[1] | R[2] | Reaction Temp/Time (°C./minutes) | Compound Name | [M + H] | HPLC Ret Time (min)[a] |
|---|---|---|---|---|---|---|
| 199 | Me | CH$_2$CO$_2$H | 100/40 | 2-(1-(4-(3-methyl-1H-pyrazol-5-ylamino)pyrrolo[1,2-f][1,2,4]triazin-2-yl)pyrrolidin-3-yl)acetic acid | 342.26 | 2.888 |
| 200 | cyclopropyl-NH-C(O)-C(Me)$_2$- | 3-pyridyl | 130/90 | N-cyclopropyl-5-(2-(3-(pyridin-3-yl)pyrrolidin-1-yl)pyrrolo[1,2-f][1,2,4]triazin-4-ylamino)-1H-pyrazole-3-carboxamide | 430.3 | 2.740 |

[a]HPLC Conditions: YMC S5 Combiscreen ODS 4.6 × 50 mm, 10-90% aqueous methanol containing 0.2% H$_3$PO$_4$, 4 min gradient, monitored at 220 or 254 nm.

Examples 201 to 211

The following examples in Table 8 have been synthesized utilizing the general procedure described in Example 171 and the given reaction times and temperatures. Starting materials were obtained as described in Example 1 from 2,4-dichloro-pyrrolo[1,2-f][1,2,4]triazine and the appropriate pyrazole (commercially available or from Table 1).

TABLE 8

| Ex. No. | R | Reaction Temp/Time (°C./minutes) | Compound Name | [M + H] | HPLC Ret Time (min)[a] |
|---|---|---|---|---|---|
| 201 | isoindolin-2-yl | 120/30 | 2-(isoindolin-2-yl)-N-(3-methyl-1,2-f][1,2,4]triazin-4-amine | 332.3 | 3.988 |

TABLE 8-continued

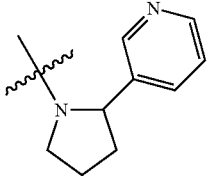

| Ex. No. | R | Reaction Temp/Time (°C./minutes) | Compound Name | [M + H] | HPLC Ret Time (min)[a] |
|---|---|---|---|---|---|
| 202 | 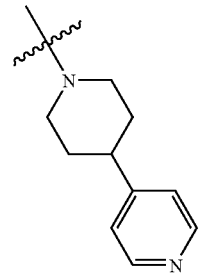 | 130/90 | N-(3-((1S,2S)-2-methylcyclopropyl)-1H-pyrazol-5-yl)-2-(3-(pyridin-3-yl)pyrrolidin-1-yl)pyrrolo[1,2-f][1,2,4]triazin-4-amine | 401.3 | 2.870 |
| 203 | 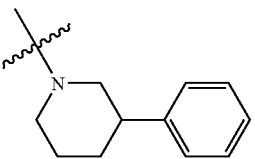 | 100/20 | N-(3-methyl-1H-pyrazol-5-yl)-2-(4-(pyridin-4-yl)piperidin-1-yl)pyrrolo[1,2-f][1,2,4]triazin-4-amine | 375.3 | 2.460 |
| 204 | 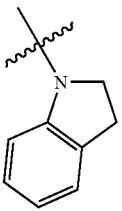 | 120/30 | N-(3-methyl-1H-pyrazol-5-yl)-2-(3-phenylpiperidin-1-yl)pyrrolo[1,2-f][1,2,4]triazin-4-amine | 374.3 | 4.268 |
| 205 | 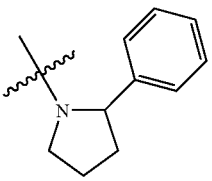 | 140/30 | 2-(indolin-1-yl)-N-(3-methyl-1H-pyrazol-5-yl)pyrrolo[1,2-f][1,2,4]triazin-4-amine | 332.3 | 4.218 |
| 206 | 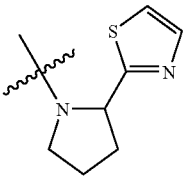 | 150/180 | N-(3-methyl-1H-pyrazol-5-yl)-2-(2-phenylpyrrolidin-1-yl)pyrrolo[1,2-f][1,2,4]triazin-4-amine | 360.3 | 3.735 |
| 207 |  | 130/120 | N-(3-methyl-1H-pyrazol-5-yl)-2-(2-(thiazol-2-yl)pyrrolidin-1-yl)pyrrolo[1,2-f][1,2,4]triazin-4-amine | 367.3 | 3.315 |

TABLE 8-continued

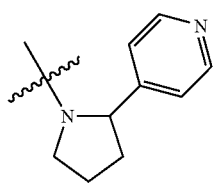

| Ex. No. | R | Reaction Temp/Time (°C./minutes) | Compound Name | [M + H] | HPLC Ret Time (min)[a] |
|---|---|---|---|---|---|
| 208 | 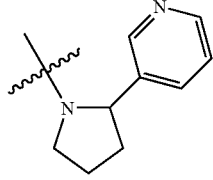 | 130/90 | N-(3-methyl-1H-pyrazol-5-yl)-2-(2-(pyridin-4-yl)pyrrolidin-1-yl)pyrrolo[1,2-f][1,2,4]triazin-4-amine | 361.3 | 2.473 |
| 209 | 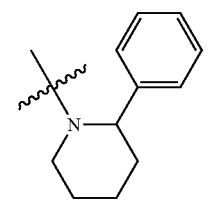 | 130/90 | N-(3-methyl-1H-pyrazol-5-yl)-2-(2-(pyridin-3-yl)pyrrolidin-1-yl)pyrrolo[1,2-f][1,2,4]triazin-4-amine | 361.3 | 2.453 |
| 210 | 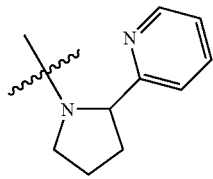 | 150/240 | N-(3-methyl-1H-pyrazol-5-yl)-2-(2-phenylpiperidin-1-yl)pyrrolo[1,2-f][1,2,4]triazin-4-amine | 374.2 | 4.145 |
| 211 | | 130/90 | N-(5-methyl-1H-pyrazol-3-yl)-2-(2-(pyridin-2-yl)pyrrolidin-1-yl)pyrrolo[1,2-f][1,2,4]triazin-4-amine | 361.2 | 2.467 |

[a]HPLC Conditions: YMC S5 Combiscreen ODS 4.6 × 50 mm, 10-90% aqueous methanol containing 0.2% $H_3PO_4$, 4 min gradient, monitored at 220 or 254 nm.

Example 212

(3-(6-Methoxypyridin-3-yl)pyrrolidin-1-yl)-N-(3-methyl-1H-pyrazol-5-yl)pyrrolo[1,2-f][1,2,4]triazin-4-amine

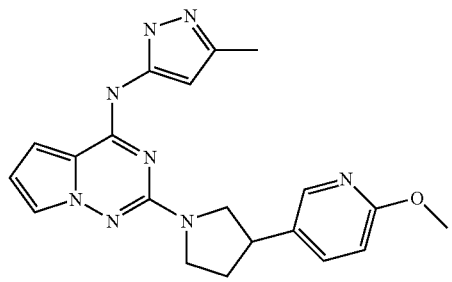

212A. Preparation of benzyl 4-(trifluoromethylsulfonyloxy)-2,3-dihydro-1H-pyrrole-1-carboxylate

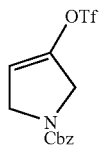

A solution of benzyl 3-oxopyrrolidine-1-carboxylate (300 mg, 1.4 mmol) in THF (10 mL) was treated with lithium bis(trimethylsilyl)amide (1.5 mL, 1 M in THF, 1.5 mmol) at −78° C. After stirring 15 minutes at −78° C., N-phenyltrifluoromethanesulfonimide (600 mg, 1.7 mmol) was added. The reaction mixture was then warmed to room temperature. The reaction was quenched with the addition of saturated aqueous NaHCO$_3$ (10 mL), and then extracted with ethyl ether (10 mL). The organic layer was washed with saturated aqueous NaCl solution (10 mL), and then dried over Na$_2$SO$_4$. The crude mixture was filtered, concentrated and purified by flash chromatography (SiO$_2$, 30% ethyl acetate/hexane) to afford the title compound (400 mg, 82%). $^1$HNMR (500 MHz, CDCl$_3$) δ 7.26 (m, 5H), 5.50 (s, 1H), 4.76 (s, 2H), 3.20 (m, 2H).

212B. Preparation of benzyl 4-(6-methoxypyridin-3-yl)-2,3-dihydro-1H-pyrrole-1-carboxylate

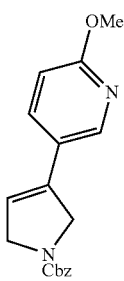

A solution of benzyl 4-(trifluoromethylsulfonyloxy)-2,3-dihydro-1H-pyrrole-1-carboxylate (200 mg, 0.57 mmol) in THF (10 mL) was purged with nitrogen for 10 minutes. The mixture was treated with K$_2$CO$_3$ (200 mg, 1.44 mmol), 6-methoxypyridin-3-ylboronic acid (100 mg, 0.66 mmol), tetrakis(triphenyl-phosphine)palladium (10 mg, 0.008 mmol), and water (100 μL). The reaction mixture was then heated to reflux for 16 hours. The reaction was treated with saturated aqueous NaHCO$_3$ (20 mL) and then extracted with ethyl ether (20 mL). The organic layer was washed with saturated aqueous NaCl (20 mL), and then dried over Na$_2$SO$_4$. The crude mixture was filtered, concentrated and purified by flash chromatography (SiO$_2$, 50% ethyl acetate/hexane) to afford the title compound (100 mg, 57%). $^1$HNMR (500 MHz, CDCl$_3$) δ 8.05 (m, 1H), 7.55 (m, 1H), 7.30 (m, 5H), 6.66 (m, 1H), 5.98 (m, 1H), 5.13 (m, 2H), 4.44 (m, 2H), 4.30 (m, 2H), 3.86 (s, 3H).

212C. Preparation of 2-methoxy-5-(pyrrolidin-3-yl)pyridine

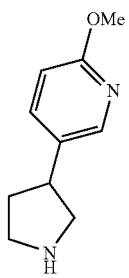

Benzyl 4-(6-methoxypyridin-3-yl)-2,3-dihydro-1H-pyrrole-1-carboxylate (100 mg, 0.33 mmol) was dissolved in methanol (10 mL). The solution was purged with nitrogen for 10 minutes and then treated with 5% Pd/C (10 mg). The reaction was stirred under a hydrogen atmosphere overnight. The catalyst was filtered off and the filtrate was concentrated to provide the title compound (60 mg, 95%). $^1$HNMR (500 MHz, CDCl$_3$) δ 8.03 (m, 1H), 7.50 (m, 1H), 6.66 (m, 1H), 3.86 (s, 3H), 3.22 (m, 2H), 3.01 (m, 2H), 2.67 (m, 1H), 2.32 (m, 1H), 1.70 (m, 1H).

212D. Preparation of 2-(3-(6-methoxypyridin-3-yl)pyrrolidin-1-yl)-N-(3-methyl-1H-pyrazol-5-yl)pyrrolo[1,2-f][1,2,4]triazin-4-amine

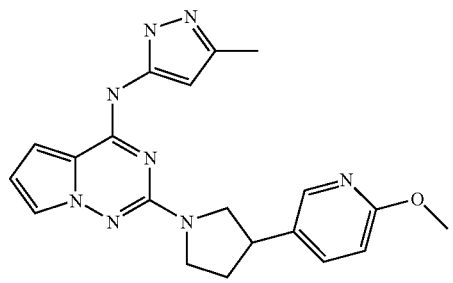

A solution of 2-chloro-N-(3-methyl-1H-pyrazol-5-yl)pyrrolo[1,2-f][1,2,4]triazin-4-amine (10 mg, 0.038 mmol) in NMP (1 mL) was treated with 2-methoxy-5-(pyrrolidin-3-yl)pyridine (60 mg, 0.32 mmol) in a microwave vial (CEM Corporation, 10 mL) The mixture was heated at 130° C. for 30 minutes using 300 W continuous power. The reaction mixture was then diluted with methanol (1 mL) and purified by preparative reversed-phase HPLC (YMC ODS-A 20×100 mm, 10-90% aqueous methanol containing 0.1% TFA, 20 min gradient, monitored at 220 nm) to give the title compound (2 mg, 14%). $^1$HNMR (500 MHz, CD$_3$OD) δ 8.02 (s, 1H), 7.67 (m, 1H), 7.55 (m, 1H), 7.17 (m, 1H), 6.76 (m, 1H), 6.62 (m, 1H), 6.08 (m, 1H), 3.97 (m, 1H), 3.82 (s, 3H), 3.80 (m, 1H), 3.62 (m, 1H), 3.49 (m, 2H), 2.38 (m, 1H), 2.24 (s, 3H), 2.17 (m, 1H). HPLC $t_R$=3.481 min. (YMC S5 Combiscreen ODS 4.6×50 mm, 10-90% aqueous methanol containing 0.2% H$_3$PO$_4$, 4 min gradient, monitored at 220 or 254 nm). m/z=391.3 (M+H).

The following amines were prepared according to the procedures described above (212B-212C) from 212A and the appropriate boronic acid.

TABLE 9

| Amine | Compound name | [M + H] | HPLC Ret Time (min)[a] |
|---|---|---|---|
| 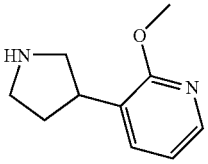 | 2-methoxy-3-(pyrrolidin-3-yl)pyridine | 179.2 | 1.052 |
| 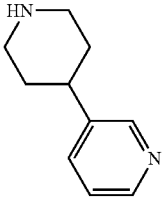 | 3-(piperidin-4-yl)pyridine | 163.2 | 0.253 |
| 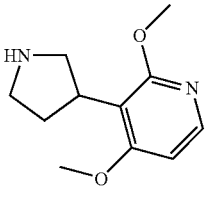 | 2,4-dimethoxy-3-(pyrrolidin-3-yl)pyridine | 209.2 | 1.888 |
| 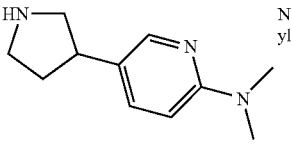 | N,N-dimethyl-5-(pyrrolidin-3-yl)pyridin-2-amine | 192.3 | 0.362 |
| 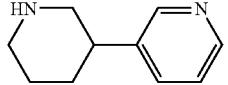 | 3-(piperidin-3-yl)pyridine | 163.2 | 0.245 |

[a]HPLC Conditions: YMC S5 Combiscreen ODS 4.6 × 50 mm, 10-90% aqueous methanol containing 0.2% $H_3PO_4$, 4 min gradient, monitored at 220 or 254 nm.

Examples 213 to 217

The following examples in Table 10 were prepared from the corresponding amine found in Table 9 in an analogous manner to Example 212 using the reaction time and temperature provided.

TABLE 10

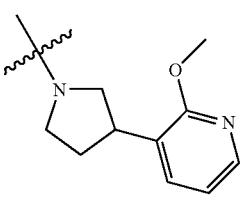

| Ex. No. | R | Reaction Time/Temp (°C./minutes) | Compound Name | [M + H] | HPLC Ret Time (min)[a] |
|---|---|---|---|---|---|
| 213 | 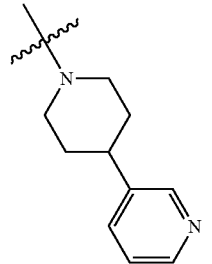 | 130/30 | 2-(3-(2-methoxypyridin-3-yl) pyrrolidin-1-yl)-N-(3-methyl-1H-pyrazol-5-yl)pyrrolo[1,2-f][1,2,4]triazin-4-amine | 391.3 | 3.693 |
| 214 | 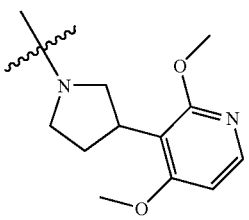 | 130/60 | N-(3-methyl-1H-pyrazol-5-yl)-2-(4-(pyridin-3-yl)piperidin-1-yl)pyrrolo[1,2-f][1,2,4]triazin-4-amine | 375.3 | 2.478 |
| 215 | 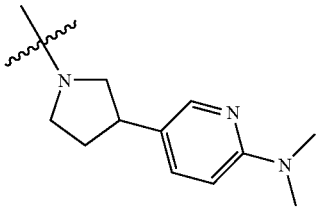 | 130/30 | 2-(3-(2,4-dimethoxypyridin-3-yl)pyrrolidin-1-yl)-N-(3-methyl-1H-pyrazol-5-yl) pyrrolo[1,2-f][1,2,4]triazin-4-amine | 421.3 | 4.058 |
| 216 | 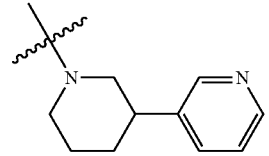 | 120/30 | 2-(3-(6-(dimethylamino) pyridin-3-yl)pyrrolidin-1-yl)-N-(3-methyl-1H-pyrazol-5-yl)pyrrolo[1,2-f][1,2,4]triazin-4-amine | 404.3 | 2.656 |
| 217 |  | 130/60 | N-(3-methyl-1H-pyrazol-5-yl)-2-(3-(pyridin-3-yl)piperidin-1-yl)pyrrolo[1,2-f][1,2,4]triazin-4-amine | 375.3 | 2.638 |

[a]HPLC Conditions: YMC S5 Combiscreen ODS 4.6 × 50 mm, 10-90% aqueous methanol containing 0.2% $H_3PO_4$, 4 min gradient, monitored at 220 or 254 nm.

Example 218

(R or S)-N-(3-Ethyl-1H-pyrazol-5-yl)-2-(3-(2-fluorophenyl)pyrrolidin-1-yl)pyrrolo[1,2-f][1,2,4]triazin-4-amine (Isomer 1)

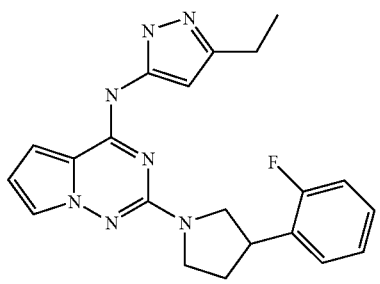

Racemic N-(3-ethyl-1H-pyrazol-5-yl)-2-(3-(2-fluorophenyl)pyrrolidin-1-yl)pyrrolo[1,2-f][1,2,4]triazin-4-amine trifluoroacetate (57 mg, 0.112 mmol) was separated into its enantiomer components by chiral supercritical fluid chromatography (AS-H 25×3 cm ID; 5 um; 35° C.; 120 mL/min; $CO_2$/EtOH (with 0.1% DEA): 67/33; 246 nm $t_R$=6.28 min.) to give the faster eluting enantiomer (7 mg, 16%). $^1$HNMR (DMSO-d6) δ 10.32 (s, 1H), 7.41 (s, 2H), 7.31 (m, 1H), 7.20 (m, 2H), 7.18 (m, 1H), 6.67 (s, 1H), 6.40 (m, 1H), 3.98 (m, 1H), 3.71 (m, 2H), 3.58 (m, 1H), 3.49 (m, 1H), 2.59 (q, J=7.55 Hz, 2H), 2.35 (s, 1H), 2.11 (dd, J=11.96, 8.69 Hz, 1H), 1.18 (t, J=7.55 Hz, 3H), HPLC $R_f$=4.135 min. (YMC S5 Combiscreen ODS 4.6×50 mm, 10-90% aqueous methanol containing 0.2% $H_3PO_4$, 4 min gradient, monitored at 220 or 254 nm). m/z=392.4 (M+H).

Examples 219 to 223

The compounds in Table 11 were obtained after subjecting the corresponding racemic mixtures to chiral separation according to the conditions given for Example 218.

TABLE 11

| Ex. No. | R$^1$ | R$^2$ | Compound name$^a$ | [M + H] | HPLC Ret Time (min)$^b$ | Chiral SFC Ret Time (min)$^c$ |
|---|---|---|---|---|---|---|
| 219 | Et | 2-fluorophenyl | (R or S)-N-(3-ethyl-1H-pyrazol-5-yl)-2-(3-(2-fluorophenyl)pyrrolidin-1-yl)pyrrolo[1,2-f][1,2,4]triazin-4-amine (Isomer 2) | 392.7 | 4.153 | 10.30 |
| 220 | Et | pyridin-3-yl | (R or S)-N-(3-ethyl-1H-pyrazol-5-yl)-2-(3-(pyridin-3-yl)pyrrolidin-1-yl)pyrrolo[1,2-f][1,2,4]triazin-4-amine (Isomer 1) | 375.3 | 2.611 | 9.68 |
| 221 | Et | pyridin-3-yl | (R or S)-N-(3-ethyl-1H-pyrazol-5-yl)-2-(3-(pyridin-3-yl)pyrrolidin-1-yl)pyrrolo[1,2-f][1,2,4]triazin-4-amine (Isomer 2) | 375.3 | 2.611 | 22.56 |
| 222 | Me | pyridin-3-yl | (R or S)-N-(3-methyl-1H-pyrazol-5-yl)-2-(3-(pyridin-3-yl)pyrrolidin-1-yl)pyrrolo[1,2-f][1,2,4]triazin-4-amine (Isomer 1) | 361.2 | 2.237 | 8.30 |

TABLE 11-continued

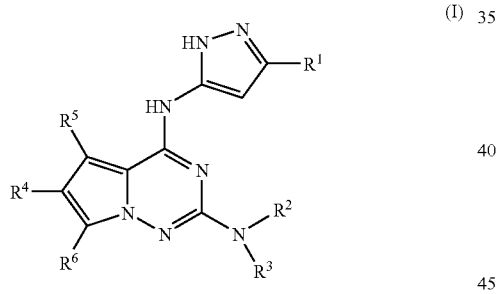

| Ex. No. | R¹ | R² | Compound name[a] | [M + H] | HPLC Ret Time (min)[b] | Chiral SFC Ret Time (min)[c] |
|---|---|---|---|---|---|---|
| 223 | Me | (pyridin-3-yl pyrrolidine) | (R or S)-N-(3-methyl-1H-pyrazol-5-yl)-2-(3-(pyridin-3-yl)pyrrolidin-1-yl) pyrrolo[1,2-f][1,2,4]triazin-4-amine (Isomer 2) | 361.2 | 2.237 | 19.54 |

[a] Isomer 1 refers to the fast eluting enantiomer under the separation conditions. Isomer 2 refers to the later eluting isomer.
[b] HPLC Conditions: YMC S5 Combiscreen ODS 4.6 × 50 mm, 10-90% aqueous methanol containing 0.2% $H_3PO_4$, 4 min gradient, monitored at 220 or 254 nm).
[c] Chiral Analytical SFC conditions: AS 250 × 4.6 mm ID; 10 um; 35° C.; 2.0 mL/min; $CO_2$/EtOH (with 0.1% DEA): 65/35.

The invention claimed is:

1. A compound of formula I (I)

wherein:
$R^1$ is hydrogen, alkyl, substituted alkyl, cycloalkyl, substituted cycloalkyl, aryl, substituted aryl, —OCH₂cycloalkyl, arylalkyl, —COOH or —CONR¹²R¹³;

$R^2$ and $R^3$ are independently hydrogen, alkyl, substituted alkyl, cycloalkyl, substituted cycloalkyl, aryl, substituted aryl, heteroaryl, substituted heteroaryl, heterocyclyl, substituted heterocyclyl, —CO alkyl, —CO substituted alkyl, —COaryl, —CO substituted aryl, —COarylalkyl, —CO substituted heteroaryl, —CO heterocyclyl alkyl, —CO(CH₂)ₙNR⁴R⁵, —CONR⁴R⁵, —CONHSO₂R⁵, —NHCONHR⁵, —(CH₂)ₙ-aryl, —(CH₂)ₙ-substituted aryl, —(CH₂)ₙ-substituted heteroaryl, —(CH₂)₂(CH₂)ₙ—OH, —(CH₂)₂(CH₂)ₙ—NH₂, —(CH₂)₂(CH₂)ₙ—S-alkyl, —SO₂alkyl or —COCF₃, two of which may be attached to the same ring carbon atom; or $R^2$ and $R^3$ are taken together with the nitrogen atom to which they are attached to form an optionally substituted 4-8 membered ring, said ring optionally containing one or more additional heteroatoms selected from —N—, —S— and —O—; said substituents on the rings are independently selected from the group consisting of hydrogen, —OH, alkyl, substituted alkyl, cycloalkyl, substituted cycloalkyl, alkoxy, substituted alkoxy, aryl, substituted aryl, arylalkyl, heteroaryl, substituted heteroaryl, heterocyclyl, substituted heterocyclyl, —CONR⁴R⁵, —OCONR⁴R⁵, —CONHSO₂R⁵, —NHCONR⁴R⁵, —NHCOalkyl, —NHCOsubstituted alkyl, —NHCOalkoxyalkyl, —NHCOalkylCOalkoxy, —NHCO(CH₂)ₙN R⁴R⁵, NHCO(CH₂)ₙbisphenyl, —NHCOaryl, —NHCOsubstituted aryl, —NHCO arylalkyl, —NHCOsubstituted arylalkyl, —NHCOheteroaryl, —NHCOsubstituted heteroaryl, —NHCOheteroarylalkyl, —NHCOsubstituted heteroarylalkyl, —NHCO(CH₂)ₙ CN, —NHCOaminosulfonylalkyl, —NHCO(CH₂)ₙNH₂, —NHCOCF₃, —NHSO₂R⁴, —CH₂OR⁴, —(CH₂)ₙ-aryl, —(CH₂)ₙ-substituted aryl, —(CH₂)ₙ-substituted heteroaryl, —(CH₂)ₙ—OH, —(CH₂)ₙNH₂, —(CH₂)ₙS-alkyl;

$R^4$ and $R^5$ are independently hydrogen, alkyl, substituted alkyl, cycloalkyl, substituted cycloalkyl, hydroxyalkyl, dihydroxyalkyl, alkoxy, substituted alkoxy, aryl, substituted aryl, heteroaryl, substituted heteroaryl, halogen, cyano, amino or substituted amino;

$R^6$ is H, $C_1$-$C_6$ alkyl, $C_1$-$C_6$ alkenyl, $C_1$-$C_6$ alkynyl, $C_3$-$C_8$ cycloalkyl, $C_1$-$C_5$ arylalkyl, aryl, substituted aryl, heteroarylalkyl, substituted heteroarylalkyl, heteroaryl, substituted heteroaryl or $C_4$-$C_8$ heterocyclyl with at least one atom on the ring selected from nitrogen or oxygen atom, and each of said $R^6$ groups optionally substituted with 1 to 3 groups selected from the group consisting of —OH, OR⁸, —COOR⁸, —NH₂, —NR⁸R⁹, —CONHR⁸, —OCONHR⁸, —CONHSO₂R⁸, —NHCONHR⁸, —SR⁸, —S(=O)R⁸, —SO₂R⁸ and —SO₂N R⁸R⁹;

R[8] is $C_1$-$C_6$ alkyl, $C_3$-$C_6$ cycloalkyl, aryl, substituted aryl, heteroaryl or substituted heteroaryl group; said substituents on the substituted aryl or substituted heteroaryl group are one or more hydrogen, halogen, alkyl, substituted alkyl, alkynyl, substituted alkynyl, alkoxy, substituted alkoxy, aryl, substituted aryl, arylalkyl, substituted arylalkyl, aryloxy or substituted aryloxy;

R[9] is hydrogen, $C_1$-$C_6$ alkyl or $C_3$-$C_6$ cycloalkyl;

R[12] and R[13] are independently hydrogen, alkyl, substituted alkyl, cycloalkyl, substituted cycloalkyl, hydroxyalkyl, dihydroxyalkyl, aryl, substituted aryl, heteroaryl, substituted heteroaryl, amino and substituted amino; or R[12] and R[13] are taken together with the nitrogen atom to which they are attached to form an optionally substituted 4-8 membered ring, said ring optionally containing one or more additional heteroatoms selected from —N—, —S— and —O—; said substituents on the ring are independently hydrogen, —OH, alkyl, substituted alkyl or hydroxyalkyl;

n is 0, 1, 2, 3 or 4;

or a pharmaceutically acceptable salt or stereoisomer thereof.

2. A compound according to claim 1 wherein:

R[2] and R[3] are taken together with the nitrogen atom to which they are attached to form an optionally substituted piperidinyl or pyrrolidinyl ring.

3. A compound of formula II

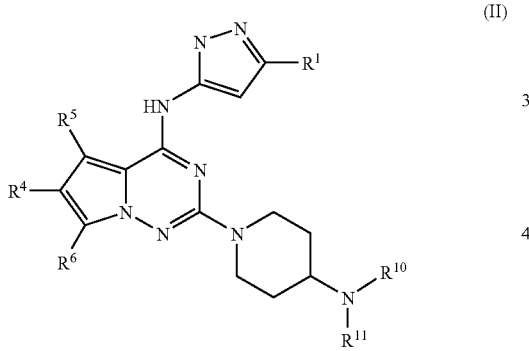

(II)

wherein:

R[1] is hydrogen, alkyl, substituted alkyl, cycloalkyl, substituted cycloalkyl, aryl, substituted aryl, —OCH$_2$cycloalkyl, arylalkyl, —COOH or —CONR[4]R[5];

R[10] and R[11] are independently hydrogen, —OH, alkyl, substituted alkyl, cycloalkyl, substituted cycloalkyl, alkoxy, substituted alkoxy, aryl, substituted aryl, arylalkyl, substituted arylalkyl, heteroaryl, substituted heteroaryl, heterocyclyl, substituted heterocyclyl, —CO alkyl, —CO substituted alkyl, —COaryl, —CO substituted aryl, —COarylalkyl, —CO substituted heteroaryl, —CO heterocyclyl alkyl, —COheteroaryl, —COsubstituted heteroaryl, —COheteroarylalkyl, —COsubstituted heteroarylalkyl, —CO(CH$_2$)$_n$NR[4]R[5], —CONR[4]R[5], —CONHSO$_2$R[5], —(CH$_2$)$_n$-aryl, —(CH$_2$)$_n$-substituted aryl, —(CH$_2$)$_n$-substituted heteroaryl, —(CH$_2$)$_2$(CH$_2$)$_n$—OH, —(CH$_2$)$_2$(CH$_2$)$_n$—NH$_2$, —(CH$_2$)$_2$(CH$_2$)$_n$—S-alkyl, —SO$_2$alkyl or —COCF$_3$, two of which may be attached to the same ring carbon atom;

R[4] and R[5] are independently hydrogen, alkyl, substituted alkyl, aryl, substituted aryl, halogen, cyano, amino or substituted amino;

R[6] is H, $C_1$-$C_6$ alkyl, $C_1$-$C_6$ alkenyl, $C_1$-$C_6$ alkynyl, $C_3$-$C_8$ cycloalkyl, $C_1$-$C_5$ arylalkyl or $C_4$-$C_8$ heterocyclyl with at least one atom on the ring selected from nitrogen or oxygen atom, and each of said R[6] groups, except H, optionally substituted with 1 to 3 groups selected from the group consisting of —OH, OR[8], —NH$_2$, —NR[8]R[9], —CONHR[8], —OCONHR[8], —CONHSO$_2$R[8], —NHCONHR[8], —SR[8], —S(=O)R[8], —SO$_2$R[8], —SO$_2$NR[8]R[9];

R[8] is $C_1$-$C_6$ alkyl, $C_3$-$C_6$ cycloalkyl, aryl, substituted aryl, heteroaryl or substituted heteroaryl group; said substituents on the substituted aryl or substituted heteroaryl group are one or more hydrogen, halogen, alkyl, substituted alkyl, alkynyl, substituted alkynyl, alkoxy, substituted alkoxy, aryl, substituted aryl, arylalkyl, substituted arylalkyl, aryloxy or substituted aryloxy;

R[9] is hydrogen, $C_1$-$C_6$ alkyl or $C_3$-$C_6$ cycloalkyl;

n is 0, 1, 2, 3 or 4;

or a pharmaceutically acceptable salt or stereoisomer thereof.

4. A compound according to claim 3 wherein:

R[1] is hydrogen, alkyl, substituted alkyl, cycloalkyl, substituted cycloalkyl, aryl or substituted aryl.

5. A compound of formula III

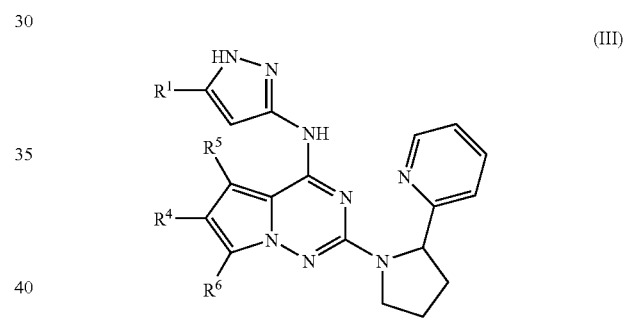

(III)

wherein:

R[1] is hydrogen, alkyl, substituted alkyl, cycloalkyl, substituted cycloalkyl, aryl, substituted aryl, —OCH$_2$cycloalkyl, arylalkyl, —COOH or —CONR[12]R[13];

R[4] and R[5] are independently hydrogen, alkyl, substituted alkyl, aryl, substituted aryl, halogen, cyano, amino or substituted amino;

R[6] is H, $C_1$-$C_6$ alkyl, $C_1$-$C_6$ alkenyl, $C_1$-$C_6$ alkynyl, $C_3$-$C_8$ cycloalkyl, $C_1$-$C_5$ arylalkyl, aryl, substituted aryl, heteroarylalkyl, substituted heteroarylalkyl, heteroaryl, substituted heteroaryl or $C_4$-$C_8$ heterocyclyl with at least one atom on the ring selected from nitrogen or oxygen atom, and each of said R[6] groups optionally substituted with 1 to 3 groups selected from the group consisting of —OH, OR[8], —COOR[8], —NH$_2$, —NR[8]R[9], —CONHR[8], —OCONHR[8], —CONHSO$_2$R[8], —NHCONHR[8], —SR[8], —S(=O)R[8], —SO$_2$R[8] and —SO$_2$NR[8]R[9];

R[8] is $C_1$-$C_6$ alkyl, $C_3$-$C_6$ cycloalkyl, aryl, substituted aryl, heteroaryl or substituted heteroaryl group; said substituents on the substituted aryl or substituted heteroaryl group are one or more hydrogen, halogen, alkyl, substituted alkyl, alkynyl, substituted alkynyl, alkoxy, substituted alkoxy, aryl, substituted aryl, arylalkyl, substituted arylalkyl, aryloxy or substituted aryloxy;

$R^9$ is hydrogen, $C_1$-$C_6$ alkyl or $C_3$-$C_6$ cycloalkyl;

$R^{12}$ and $R^{13}$ are independently hydrogen, alkyl, substituted alkyl, cycloalkyl, substituted cycloalkyl, hydroxyalkyl, dihydroxyalkyl, aryl, substituted aryl, heteroaryl, substituted heteroaryl, amino or substituted amino; or $R^{12}$ and $R^{13}$ are taken together with the nitrogen atom to which they are attached to form an optionally substituted 4-8 membered ring, said ring optionally containing one or more additional heteroatoms selected from —N—, —S— and —O—; said substituents on the ring are independently hydrogen, —OH, alkyl, substituted alkyl or hydroxyalkyl;

or a pharmaceutically acceptable salt or stereoisomer thereof.

6. A pharmaceutical composition comprising one or more compounds of claim 1 and a pharmaceutically acceptable carrier.

7. A pharmaceutical composition comprising one or more compounds of claim 3 and a pharmaceutically acceptable carrier.

8. A pharmaceutical composition comprising one or more compounds of claim 5 and a pharmaceutically acceptable carrier.

9. A pharmaceutical composition comprising one or more compounds according to claim 1 in combination with a pharmaceutically acceptable carrier and one or more other anti-cancer or cytotoxic agent.

10. A method for treating a proliferative disease selected from rheumatoid arthritis and breast cancer, comprising administering to a mammalian species in need thereof, a therapeutically effective amount of one or more compound according to claim 1.

* * * * *

UNITED STATES PATENT AND TRADEMARK OFFICE
CERTIFICATE OF CORRECTION

PATENT NO. : 7,531,539 B2  Page 1 of 1
APPLICATION NO. : 11/835456
DATED : May 5, 2009
INVENTOR(S) : Fink et al.

It is certified that error appears in the above-identified patent and that said Letters Patent is hereby corrected as shown below:

In Claim 1:
Column 124, Line 62 delete "said $R^6$" and insert -- said substituted $R^6$ --

In Claim 5:
Column 126, Line 57 delete "said $R^6$" and insert -- said substituted $R^6$ --

Signed and Sealed this

First Day of June, 2010

David J. Kappos
*Director of the United States Patent and Trademark Office*